US007538215B2

(12) United States Patent
Konradi et al.

(10) Patent No.: US 7,538,215 B2
(45) Date of Patent: May 26, 2009

(54) COMPOUNDS WHICH INHIBIT LEUKOCYTE ADHESION MEDIATED BY VLA-4

(75) Inventors: Andrei W. Konradi, San Francisco, CA (US); Michael A. Pleiss, Sunnyvale, CA (US); Eugene D. Thorsett, Half Moon Bay, CA (US); Christopher Semko, Fremont, CA (US); Christopher Joseph Soares, La Jolla, CA (US); Christine M. Tarby, Hockessin, DE (US)

(73) Assignees: Elan Pharmaceuticals, Inc., South San Francisco, CA (US); Wyeth, Madison, NJ (US)

( * ) Notice: Subject to any disclaimer, the term of this patent is extended or adjusted under 35 U.S.C. 154(b) by 238 days.

(21) Appl. No.: 11/145,489

(22) Filed: Jun. 2, 2005

(65) Prior Publication Data

US 2005/0261293 A1 Nov. 24, 2005

Related U.S. Application Data

(62) Division of application No. 10/218,445, filed on Aug. 15, 2002, now Pat. No. 6,903,088, which is a division of application No. 09/489,378, filed on Jan. 21, 2000, now Pat. No. 6,479,492.

(60) Provisional application No. 60/116,923, filed on Jan. 22, 1999, provisional application No. 60/160,999, filed on Oct. 21, 1999.

(51) Int. Cl.
*C07D 239/02* (2006.01)
*C07D 237/00* (2006.01)
*C07D 415/00* (2006.01)

(52) U.S. Cl. ....................... 544/330; 544/327; 544/328; 544/329; 544/332

(58) Field of Classification Search ....................... None
See application file for complete search history.

(56) References Cited

U.S. PATENT DOCUMENTS

| | | | |
|---|---|---|---|
| 4,018,913 | A | 4/1977 | Okamoto et al. |
| 4,018,915 | A | 4/1977 | Okamoto et al. |
| 4,036,955 | A | 7/1977 | Okamoto et al. |
| 4,041,156 | A | 8/1977 | Okamoto et al. |
| 4,046,876 | A | 9/1977 | Okamoto et al. |
| 4,055,636 | A | 10/1977 | Okamoto et al. |
| 4,055,651 | A | 10/1977 | Okamoto et al. |
| 4,070,457 | A | 1/1978 | Okamoto et al. |
| 4,073,914 | A | 2/1978 | Kikumoto et al. |
| 4,085,057 | A | 4/1978 | Masuda et al. |
| 4,096,255 | A | 6/1978 | Kikumoto et al. |
| 4,104,392 | A | 8/1978 | Okamoto et al. |
| 4,438,122 | A | 3/1984 | Holmwood et al. |
| 4,505,910 | A | 3/1985 | Bagli |
| 4,518,600 | A | 5/1985 | Holmwood et al. |
| 4,544,402 | A | 10/1985 | Schnurbusch et al. |
| 4,559,345 | A | 12/1985 | Gomarasca et al. |
| 4,672,065 | A | 6/1987 | Spatz |
| 4,908,368 | A | 3/1990 | Murase et al. |
| 4,959,364 | A | 9/1990 | Mueller et al. |
| 4,992,439 | A | 2/1991 | Meanwell |
| 5,030,644 | A | 7/1991 | Baldwin et al. |
| 5,120,734 | A | 6/1992 | Klausener et al. |
| 5,238,934 | A | 8/1993 | Knüppel et al. |
| 5,278,184 | A | 1/1994 | Artico et al. |
| 5,510,332 | A | 4/1996 | Kogan et al. |
| 5,580,868 | A | 12/1996 | Lunkenheimer et al. |
| 5,770,573 | A | 6/1998 | Arrhenius et al. |
| 5,814,643 | A | 9/1998 | Duggan et al. |
| 5,861,429 | A | 1/1999 | Sato et al. |
| 5,925,644 | A | 7/1999 | Jakobi et al. |
| 5,942,504 | A | 8/1999 | Grobelny |
| 5,955,491 | A | 9/1999 | Sohda et al. |
| 5,962,479 | A | 10/1999 | Chen |
| 5,972,946 | A | 10/1999 | Murata et al. |
| 6,005,117 | A | 12/1999 | Wehner et al. |
| 6,492,372 | B1 * | 12/2002 | Konradi et al. ......... 514/252.18 |
| 6,903,088 | B2 * | 6/2005 | Konradi et al. .............. 514/183 |
| 6,911,439 | B2 * | 6/2005 | Konradi et al. .............. 514/183 |
| 7,005,433 | B2 * | 2/2006 | Konradi et al. ......... 514/252.18 |

FOREIGN PATENT DOCUMENTS

| | | |
|---|---|---|
| CA | 2241149 | 7/1977 |

(Continued)

OTHER PUBLICATIONS

Hladon, Buguslaw et al., In Vitro cytostatic activity of some amino acid 4N-substituted cytosines, *Arch. Immunol. Ther. Exp.* (1992), 40(2), 145-50. (Abstract).

(Continued)

*Primary Examiner*—Kevin E Weddington
(74) *Attorney, Agent, or Firm*—Foley & Lardner LLP

(57) ABSTRACT

Disclosed are compounds which bind VLA-4. Certain of these compounds also inhibit leukocyte adhesion and, in particular, leukocyte adhesion mediated by VLA-4. Such compounds are useful in the treatment of inflammatory diseases in a mammalian patient, e.g., human, such as asthma, Alzheimer's disease, atherosclerosis, AIDS dementia, diabetes, inflammatory bowel disease, rheumatoid arthritis, tissue transplantation, tumor metastasis and myocardial ischemia. The compounds can also be administered for the treatment of inflammatory brain diseases such as multiple sclerosis.

4 Claims, No Drawings

FOREIGN PATENT DOCUMENTS

| | | | |
|---|---|---|---|
| CA | 2259224 | | 1/1978 |
| DE | 26 55 636 | | 6/1977 |
| DE | 19536891 | | 4/1997 |
| DE | 19548709 | A | 7/1997 |
| DE | 19654483 | A | 1/1998 |
| DE | 19713000 | | 10/1998 |
| EP | 0 288 176 | | 10/1988 |
| EP | 0 147 211 | | 7/1989 |
| EP | 0330506 | A2 | 8/1989 |
| EP | 0330506 | A3 | 8/1989 |
| EP | 0 526 348 | | 2/1993 |
| EP | 0 535 521 | | 4/1993 |
| WO | WO 92/16549 | | 10/1992 |
| WO | WO 93/12809 | | 7/1993 |
| WO | WO 96/01644 | | 1/1996 |
| WO | WO 96/22966 | | 8/1996 |
| WO | WO 97/23451 | | 7/1997 |
| WO | WO 98/00395 | | 1/1998 |
| WO | WO 98/33783 | | 8/1998 |
| WO | WO 98/53817 | | 12/1998 |
| WO | WO 99/06390 | | 2/1999 |
| WO | WO 99/06391 | | 2/1999 |
| WO | WO 99/06431 | | 2/1999 |
| WO | WO 99/06432 | | 2/1999 |
| WO | WO 99/06433 | | 2/1999 |
| WO | WO 99/10312 | | 3/1999 |
| WO | WO 99/10313 | | 3/1999 |
| WO | WO 99/37605 | | 7/1999 |
| WO | WO 99/37618 | | 7/1999 |
| WO | WO 99/52898 | | 10/1999 |

OTHER PUBLICATIONS

Hoffman, Seigfried; Schubert, Herman; Nitsche, Klaus, N-Pyrimidinylamino acids. III. N-(oxopyrimidinyl) derivatives of neutral amino acids,*Z. Chem.* (1972), 12(1) 21-2, Coden: Zeceal (Abstract).

Teranishi, Katsunori; Goto, Toshio, Synthesis and Chemiluminescense of Coelenterazine (Oplophorus Luciferin) analogs, *Bull. Chem. Soc. Jpn.* (1990), 63(11), 3132-40 , (Abstract).

Abraham, W.M., et al. "α4-Integrins Mediate Antigen -induced Late Bronchial Responses and Prolonged Airway Hyperresponsiveness in Sheep." *J. Clin. Invest.* 93: 776-787 (1994).

Bao, L., et al. "Correlation of VLA-4 integrin expression with metastatic potential in various human tumour cell lines." *Diff.* 52: 239-246 (1993).

Baron, J.L., et al. "Surface Expression ofα4 Integrin by CD4 T Cells in Required for Their Entry into Brain Parenchyma." *J. Exp. Med.* 177: 57-68 (1993).

Baron, J.L., et al. et al. "ThePathogenesis of Adeoptive Murine Autoimmune Diabetes Requires an Interaction between α4-Integrins and Vascular Cell Adhesion Molecule-1." *J. Clin. Invest.* 93: 1700-1708 (1994).

Burkly, L.C., et al. "Protection Against Adoptive Transfer of Autoimmune Diabetes Mediated Through Very Late Antigent-4 Integrin." *Diabetes.* 43: 529-534 (1994).

Cybulsky, M.I., et al. "Endothelial Expression of a Mononuclear Leukocyte Adhesion Molecule During Atherogenesis." *Science.* 251: 788-791 (1991).

Elices, M.J., et al. "Expression and Functional Significance of Alternatively Spliced CS1 Fibronecting in Rheumatoid Arthritis Microsvasculature." *J. Clin. Invest.* 93: 405-416 (1994).

Elices, M.J., et al. "VCAM-1 on Activated Endothelium Interacts with the Leukocyte Integrin VLA-4 at a Site Distinct from the CLA-4/Fibronectin Binding Site." *Cell.* 60: 577-584 (1990).

Hamann, A., et al. "Role of α4-Integrins in Lymphocute Homing to Mucosal Tissues in Vivo." *J. Immunology.* 152: 3283-3292 (1994).

Kawaguchi, S., et al. "VLA-4 Molecules on Tumor Cells Initiate an Adhesive Interaction with VCAM-1 Molecules on Endothelial Cell Surface." *Japanese J. Cancer Res.* 83: 1304-1316 (1992).

Lauri, D., et al. "Decreased adhesion to endothelial cells and matrix proteins of H-2K$^b$ gene transfected tumour cells." *British J. Cancer.* 68: 862-867 (1993).

Li, H., et al. "An Atherogenic Diet Rapidly Induces VCAM-1, a Cytokine-Regulatable Mononuclear Leeukocyte Adhesion Molecule, in Rabbit Aortic Endothelum." *Arterioscler. Thromb.* 13(2): 197-204 (1993).

Mulligan, M.S., et al. "Role ofβ1, β2 Integrins and ICAM-1 in Lung Injury after Deposition of IgG and IgA Immune Complexes."*J. Immunol.* 150(6): 2407-2417 (1993).

Okarhara, H., et al. "Involvement of Very Late Activation Antigen 4 (VLA-4) and Vascular Cell Adhesion Molecule 1(VCAM-1) in Tumor Necrosis Factor α Enhancement of Experimental Metastasis." *Can. Res.* 54: 3233-3236 (1994).

Osborn, L. "Leukocyte Adhesion to Endothelium in Inflammation." *Cell.* 62: 3-6 (1990).

Paavonen, T., et al. "In Vivo Evidence of the Role of $\alpha_4\beta_1$-VCAM-1 Interaction in Sarcoma, but not in Carcinoma Extravasation." *Int. J. Can.* 58: 298 (1994).

Paul, L.C.,et al. "Monoclonal Antibodies Against LFA-1 and VLA-4 Inhibit Graft Vasculitis in Rat Cardiac Allografts." *Transpl. Proceed.* 25(1): 813-814 (1993).

Postigo, A.A., et al. "Increased Binding of Synovial T Lumphocytes from Rheumatoid Arthritis to Endothelial-Leukocyte Adhesion Molecule-1 (ELAM-1) and Vascular Cell Adhesion Molecule-1 (VCAM-1)." *J. Clin. Invest.* 89: 1445-1452 (1991).

Pretolani, M., et al. "Antibody to Very Late Activation Antigen 4 Prevents Antigen-induced Bronchial Hyperreactivity and Cellular Infiltration in the Guinea Pig Arways." *J. Exp. Med.* 180: 795-805 (1994).

Sasseville, V.G., et al. "Monocyte Adhesion to Endothelium in Simian Immunodeficiency Virus-Induced AIDS Encephalitis is Mediated by Vascular Cell Adhesion Molecule-1/$\alpha_4\beta_1$ Integrin Interactions." *Am. J. Path.* 144(1): 27-40 (1994).

Schadendorf, D., et al. "Tumour Progression and Metastatic BehaviourIn Vivo Correlates with Integrin Expression on Melanocytic Tumours." *J. Path.* 170: 429-434 (1993).

Springer, T.A. "Adhesion receptors of the immune system." *Nature.* 346: 425-434 (1990).

Teranishi, K., et al. "Synthesis and Chemiluminescence of Coelenterazine (*Oplophorus* Luciferin) Analogues." *Bull. Chem. Soc. Jpn.* 63(11): 3132-3140 (1990).

Van Dinther-Janssen, A.C.H.M., et al. "Role of the CS1 adhesion motif of fibronectin in T cell adhesion to synovial membrane and peripheral lymph node endothelium." *Annals. Rheumatic Dis.* 52: 672-676 (1993).

Van Dinther-Janssen, A.C.H.M., et al. "The VLA-4/VCAM-1 Pathway is Involved in Lymphocyte Adhesion to Endothelium in Rheumatoid Synovium." *J. Immunology.* 147(12): 4207-4210 (1991).

Vedder, N.B., et al. "Role of neutrophils in generalized reperfusion injury associated with resuscitation from shock." *Surgery.* 106: 509-516 (1989).

Yang, C-D., et al. "Inhibition of insultitis and prevention of diabetes in nonobese diabetic mice by blocking L-selecting and very late antigen 4 adhesion receptors." *Proc. Natl. Acad. Sci.,* USA. 90: 10494-10498 (1993).

Yednock, T.A., et al. "Prevention of experimental autoimmune encephalomyelitis by antibodies against $\alpha_4\beta_1$ integrin." *Nature.* 356: 63 (1992).

Advani, S.B., et al. "Potential Antineoplastic Agents: N-(2-Benzoxazolyl)amino Acid Esters." *J. of Pharm. Sci.* 57(10): 1693-1696 (1968).

Gordeev, M.F. "Combinatorial Approaches to pharmacophoric Heterocycles: A Solid-Phase Synthesis of 3,1-Benzoxazine-4-ones." *Biotech. and Bioengineering.* 61(1): 13-16 (1998).

Henke, B.R., et al. "N-(2-Benzoylphenyl)-L-tyrosine :Aryl Agonists. 1. Discovery of a Novel Series of Potent Antihyperglycemic and Antihyperlpidemic Agents." *J. Med. Chem.* 41(25): 5020-5036 (1998).

Lazer, E.S., et al. "Benzoxazolamines and Benzothiazolamines: Potent, Enantioselective Inhibitors of Leukotriene Biosynthesis with a Novel Mechanism of Action." *J. Med. Chem.* 37(7): 913-923 (1994).

Ma, D., et al. "Accelerating Effect Induced by the Structure of aAmino Acid in the Copper Catalyzed Coupling Reaction of Aryl Halides with a-Amino Acids. Synthesis of Benzolactam-V8." *J. Am. Chem. Soc.* 120(48): 12459-12467 (1998).
Chem. Abstr. 125:89348, also cited as HCAPLUS, JP 08100141, "Hiroshi, et al.", Apr. 1996.
Kascheres et al. Chemical Abstract DN 85:177341, also cited as *J. Org. Chem.* 41/22, 3546-9 (1976).
Toniolo et al. Chemical Abstract DN 77:5775, also cited as *J. Chem. Soc.*, Perkin Transactinos, 1, Org. & Bio-Org Chem., 9/10, 1178-81 (1972).
Wyzsza et al. ChemicalAbstract DN 70:96568, also cited as Roczniki Chemii, 42/10, 1647-60 (1968).

* cited by examiner

COMPOUNDS WHICH INHIBIT LEUKOCYTE ADHESION MEDIATED BY VLA-4

CROSS-REFERENCE TO RELATED APPLICATIONS

This application is a Divisional of U.S. patent application Ser. No. 10/218,445, filed on Aug. 15, 2002, now U.S. Pat. No. 6,903,088, which is a Divisional of U.S. patent application Ser. No. 09/489,378, filed on Jan. 21, 2000, now U.S. Pat. No. 6,479,492, which claims the benefit of U.S. Provisional Application No. 60/116,923, filed Jan. 22, 1999, and U.S. Provisional Application No. 60/160,999, filed Oct. 21, 1999, the disclosures of which are incorporated herein by reference in their entireties.

BACKGROUND OF THE INVENTION

Field of the Invention

This invention relates to compounds which inhibit leukocyte adhesion and, in particular, leukocyte adhesion mediated by VLA-4.

REFERENCES

The following publications, patents and patent applications are cited in this application as superscript numbers:

[1] Hemler and Takada, European Patent Application Publication No. 330,506, published Aug. 30, 1989
[2] Elices, et al., *Cell,* 60:577-584 (1990)
[3] Springer, *Nature,* 346:425-434 (1990)
[4] Osborn, *Cell,* 62:3-6 (1990)
[5] Vedder, et al., *Surgery,* 106:509 (1989)
[6] Pretolani, et al., *J. Exp. Med.,* 180:795 (1994)
[7] Abraham, et al., *J. Clin. Invest.,* 93:776 (1994)
[8] Mulligan, et al., *J. Immunology,* 150:2407 (1993)
[9] Cybulsky, et al., *Science,* 251:788 (1991)
[10] Li, et al., *Arterioscler. Thromb.,* 13:197 (1993)
[11] Sasseville, et al., *Am. J. Path.,* 144:27 (1994)
[12] Yang, et al., *Proc. Nat. Acad. Science* (*USA*), 90:10494 (1993)
[13] Burkly, et al., *Diabetes,* 43:529 (1994)
[14] Baron, et al., *J. Clin. Invest.,* 93:1700 (1994)
[15] Hamann, et al., *J. Immunology,* 152:3238 (1994)
[16] Yednock, et al., *Nature,* 356:63 (1992)
[17] Baron, et al., *J. Exp. Med.,* 177:57 (1993)
[18] van Dinther-Janssen, et al., *J. Immunology,* 147:4207 (1991)
[19] van Dinther-Janssen, et al., *Annals. Rheumatic Dis.,* 52:672 (1993);
[20] Elices, et al., *J. Clin. Invest.,* 93:405 (1994)
[21] Postigo, et al., *J. Clin. Invest.,* 89:1445 (1991)
[22] Paul, et al., *Transpl. Proceed.,* 25:813 (1993)
[23] Okarhara, et al., *Can. Res.,* 54:3233 (1994)
[24] Paavonen, et al., *Int. J. Can.,* 58:298 (1994)
[25] Schadendorf, et al., *J. Path.,* 170:429 (1993)
[26] Bao, et al., *Diff.,* 52:239 (1993)
[27] Lauri, et al., *British J. Cancer,* 68:862 (1993)
[28] Kawaguchi, et al., *Japanese J. Cancer Res.,* 83:1304 (1992)
[29] Kogan, et al., U.S. Pat. No. 5,510,332, issued Apr. 23, 1996
[30] International Patent Appl. Publication No. WO 96/01644

All of the above publications, patents and patent applications are herein incorporated by reference in their entirety to the same extent as if each individual publication, patent or patent application was specifically and individually indicated to be incorporated by reference in its entirety.

State of the Art

VLA-4 (also referred to as $\alpha_4\beta_1$ integrin and CD49d/CD29), first identified by Hemler and Takada[1] is a member of the $\beta1$ integrin family of cell surface receptors, each of which comprises two subunits, an $\alpha$ chain and a $\beta$ chain. VLA-4 contains an $\alpha4$ chain and a $\beta1$ chain. There are at least nine $\beta1$ integrins, all sharing the same $\beta1$ chain and each having a distinct $\alpha$ chain. These nine receptors all bind a different complement of the various cell matrix molecules, such as fibronectin, laminin, and collagen. VLA-4, for example, binds to fibronectin. VLA-4 also binds non-matrix molecules that are expressed by endothelial and other cells. These non-matrix molecules include VCAM-1, which is expressed on cytokine-activated human umbilical vein endothelial cells in culture. Distinct epitopes of VLA-4 are responsible for the fibronectin and VCAM-1 binding activities and each activity has been shown to be inhibited independently.[2]

Intercellular adhesion mediated by VLA-4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn[4].

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult (Vedder et al.[5]). Other inflammatory conditions mediated by an adhesion mechanism include, by way of example, asthma[6-8], Alzheimer's disease, atherosclerosis[9-10], AIDS dementia[11], diabetes[12-14] (including acute juvenile onset diabetes), inflammatory bowel disease[15] (including ulcerative colitis and Crohn's disease), multiple sclerosis[16-17], rheumatoid arthritis[18-21], tissue transplantation[22], tumor metastasis[23-28], meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

In view of the above, assays for determining the VLA-4 level in a biological sample containing VLA-4 would be useful, for example, to diagnosis VLA-4 mediated conditions. Additionally, despite these advances in the understanding of leukocyte adhesion, the art has only recently addressed the use of inhibitors of adhesion in the treatment of inflammatory brain diseases and other inflammatory conditions[29, 30]. The present invention addresses these and other needs.

SUMMARY OF THE INVENTION

This invention provides compounds which bind to VLA-4. Such compounds can be used, for example, for treating diseases mediated by VLA-4, to assay for the presence of VLA-4 in a sample, and in pharmaceutical compositions to inhibit cellular adhesion mediated by VLA-4, for example, binding of VCAM-1 to VLA-4. The compounds of this invention have a binding affinity to VLA-4 as expressed by an $IC_{50}$ of about 15 µM or less (as measured using the procedures described in Example A below).

Accordingly, in one aspect, this invention is directed to a method for treating a disease mediated by VLA-4 in a patient, which method comprises administering to said patient a pharmaceutical composition comprising a pharmaceutically acceptable carrier and a therapeutically effective amount of a compound of formula Ia and/or Ib:

Ia

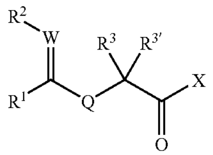

and

Ib

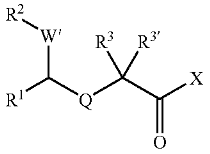

wherein, in formula Ia, $R^1$ and $R^2$, together with the carbon atom and W to which they are bound respectively, are joined to form an aryl, cycloalkenyl, heteroaryl or heterocyclic group having at least five atoms in the aryl, cycloalkenyl, heteroaryl or heterocyclic group and optionally containing or additionally containing in the case of heteroaryl and heterocyclic groups 1 to 3 heteroatoms selected from the group consisting of oxygen, nitrogen and sulfur, and wherein the heteroaryl or heterocyclic group is monocyclic;

in formula Ib, $R^1$ and $R^2$, together with the carbon atom and W' to which they are bound respectively, are joined to form a cycloalkyl, cycloalkenyl or heterocyclic group having at least five atoms in the cycloalkyl, cycloalkenyl or heterocyclic group and optionally containing or additionally containing in the case of the heterocyclic group 1 to 3 heteroatoms selected from the group consisting of oxygen, nitrogen and sulfur, and wherein the heterocyclic group is monocyclic;

and further wherein said aryl, cycloalkyl, cycloalkenyl, heteroaryl or heterocyclic group of formula Ia or Ib is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, $—OS(O)_2$-alkyl, $—OS(O)_2$-substituted alkyl, $—OS(O)_2$-aryl, $—OS(O)_2$-substituted aryl, $—OS(O)_2$-heteroaryl, $—OS(O)_2$-substituted heteroaryl, $—OS(O)_2$-heterocyclic, $—OS(O)_2$-substituted heterocyclic, $—OSO_2—NRR$ where each R is independently hydrogen or alkyl, $—NRS(O)_2$-alkyl, $—NRS(O)_2$-substituted alkyl, $—NRS(O)_2$-aryl, $—NRS(O)_2$-substituted aryl, $—NRS(O)_2$-heteroaryl, $—NRS(O)_2$-substituted heteroaryl, $—NRS(O)_2$-heterocyclic, $—NRS(O)_2$-substituted heterocyclic, $—NRS(O)_2—NR$-alkyl, $—NRS(O)_2—NR$-substituted alkyl, $—NRS(O)_2—NR$-aryl, $—NRS(O)_2—NR$-substituted aryl, $—NRS(O)_2—NR$-heteroaryl, $—NRS(O)_2—NR$-substituted heteroaryl, $—NRS(O)_2—NR$-heterocyclic, $—NRS(O)_2—NR$-substituted heterocyclic where R is hydrogen or alkyl, $—N[S(O)—R']_2$ and $—N[S(O)_2—NR']_2$ where each R' is independently selected from the group consisting of alkyl, substituted alkyl, aryl, substituted aryl, heteroaryl, substituted heteroaryl, heterocyclic and substituted heterocyclic;

$R^3$ and $R^{3'}$ are independently selected from the group consisting of hydrogen, isopropyl, $—CH_2Z$ where Z is selected from the group consisting of hydrogen, hydroxyl, acylamino, alkyl, alkoxy, aryloxy, aryl, aryloxyaryl, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted alkyl, substituted alkoxy, substituted aryl, substituted aryloxy, substituted aryloxyaryl, substituted cycloalkyl, heteroaryl, substituted heteroaryl, heterocyclic and substituted heterocyclic, and where $R^3$ and $R^{3'}$ are joined to form a substituent selected from the group consisting of $=CHZ$ where Z is defined above provided that Z is not hydroxyl or thiol, cycloalkyl, substituted cycloalkyl, cycloalkenyl, substituted cycloalkenyl, heterocyclic and substituted heterocyclic;

Q is selected from the group consisting of —O—, —S—, —S(O)—, $—S(O)_2$, and $—NR^4—$;

$R^4$ is selected from the group consisting of hydrogen, alkyl, substituted alkyl, alkenyl, substituted alkenyl, cycloalkyl, substituted cycloalkyl, cycloalkenyl, substituted cycloalkenyl, aryl, substituted aryl, heteroaryl, substituted heteroaryl, heterocyclic and substituted heterocyclic or, optionally, $R^4$ and $R^1$ or $R^4$ and $R^2$, together with the atoms to which they are bound, are joined to form a heteroaryl, a substituted heteroaryl, a heterocyclic or a substituted heterocyclic group;

W is selected from the group consisting of nitrogen and carbon; and

W' is selected from the group consisting of nitrogen, carbon, oxygen, sulfur, S(O), and $S(O)_2$;

X is selected from the group consisting of hydroxyl, alkoxy, substituted alkoxy, alkenoxy, substituted alkenoxy, cycloalkoxy, substituted cycloalkoxy, cycloalkenoxy, substituted cycloalkenoxy, aryloxy, substituted aryloxy, heteroaryloxy, substituted heteroaryloxy, heterocyclyloxy, substituted heterocyclyloxy and —NR"R" where each R" is independently selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic and substituted heterocyclic;

and enantiomers, diastereomers, and pharmaceutically acceptable salts thereof; provided that:

(i) the compound of formula Ia or Ib has a binding affinity to VLA-4 as expressed by an $IC_{50}$ of about 15 μM or less; and (ii) in formula Ia and Ib, $R^1$ and $R^2$, together with the carbon atom and W to which they are bound respectively, do not form a substituted or unsubstituted pyridazine ring.

Preferably, in the above method, $R^3$ is $—(CH_2)_x—Ar—R^9$, where Ar is aryl, substituted aryl, heteroaryl and substituted heteroaryl; $R^9$ is selected from the group consisting acyl, acylamino, acyloxy, aminoacyl, aminocarbonylamino, aminothiocarbonylamino, aminocarbonyloxy, oxycarbonylamino, thioamidino, thiocarbonylamino, aminosulfonylamino, aminosulfonyloxy, aminosulfonyl, oxysulfonylamino, and oxysulfonyl; x is an integer from 0 to 4; and $R^{3'}$ is hydrogen.

More preferably, $R^3$ is a group of the formula:

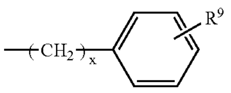

wherein $R^9$ is as defined herein. Preferably, $R^9$ is in the para position of the phenyl ring and x is an integer from 1 to 4, more preferably x is 1.

Preferably, $R^9$ is selected from $—O\text{-}Z\text{-}NR^{11}R^{11'}$ and $—O\text{-}Z\text{-}R^{12}$ wherein $R^{11}$ and $R^{11''}$ are independently selected from the group consisting of hydrogen, alkyl, substituted alkyl, cycloalkyl, substituted cycloalkyl, cycloalkenyl, substituted cycloalkenyl, heterocyclic, substituted heterocyclic, and where $R^{11}$ and $R^{11'}$ are joined to form a heterocycle or a substituted heterocycle, $R^{12}$ is selected from the group consisting of heterocycle and substituted heterocycle, and Z is selected from the group consisting of —C(O)— and $—SO_2—$, Z is preferably —C(O)—. In a more preferred embodiment, $R^9$ is $—OC(O)NR^{11}R^{11'}$, wherein $R^{11}$ and $R^{11'}$ are as defined herein, more preferably preferably $R^9$ is $—OC(O)N(CH_3)_2$.

In the above method, Q is preferably $—NR^4—$ wherein $R^4$ is as defined above, more preferably $R^4$ is hydrogen or alkyl, even more preferably $R^4$ is hydrogen.

In another preferred embodiment, $R^1$ and $R^2$, together with the carbon atom and W to which they are bound respectively, are joined to form a substituted or unsubstituted monocyclic heteroaryl or heterocyclic group wherein the heteroaryl group has 1 to 4 heteroatoms selected from the group consisting of N. O, or S and the heterocyclic group contains 1 to 3 heteroatoms selected from the group consisting of N, O, or S(O)n wherein n is 0 to 2.

More preferably, the above method employs a compound of formula IIa, IIb, or IIc:

IIa

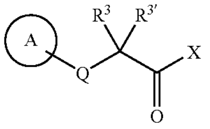

IIb

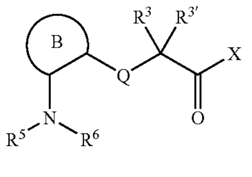

-continued

IIc

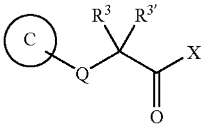

wherein:

ring A is selected from the group consisting of pyrrole, pyrazole, imidazole, pyrimidine, 1,2,3-triazole, 1,2,4-triazole, tetrazole, and thiophene wherein each of said pyrrole, pyrazole, imidazole, and thiophene ring is substituted with 1 to 3 substituent(s), and each of said pyrimidine, 1,2,3-triazole, 1,2,4-triazole, and tetrazole ring is substituted with 1 to 2 substituent(s), independently selected from the group consisting of alkyl, alkoxy, halogen, nitro, amino, substituted amino, aryl, substituted aryl, heteroaryl, substituted heteroaryl, heterocyle, substitued heterocycle, and $—SO_2R^a$ (wherein $R^a$ is alkyl, aryl, or substituted aryl);

ring B forms a 1-oxo-1,2,5-thiadiazole or a 1,1-dioxo-1,2,5-thiadiazole ring;

ring C is pyridine or 1,3,5-triazine ring wherein each of said ring is substituted with 1 to 2 substituent(s) independently selected from the group consisting of alkyl, substituted alkyl, alkoxy, halogen, hydroxy, amino, substituted amino, aryl, substituted aryl, heteroaryl, substituted heteroaryl, heterocyle, and substitued heterocycle;

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and $—SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl;

or optionally, one of, $R^4$ and ring B, $R^4$ and $R^5$, $R^4$ and $R^6$, or $R^5$ and $R^6$, together with the atoms to which they are bound, can be joined to form a heterocyclic or substituted heterocyclic ring; and $R^3$, $R^{3'}$, Q and X are as defined herein; and enantiomers, diastereomers, pharmaceutically acceptable salts thereof.

Within the above preferred and more preferred groups, an even more preferred group of compounds is represented by formula IIa', IIb', or IIc':

IIa'

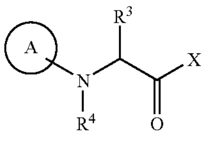

-continued

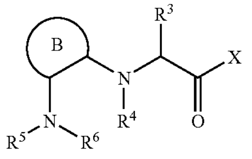

IIb′

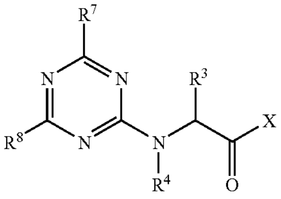

IIc′ wherein:

$R^4$ is hydrogen or alkyl; preferably hydrogen or methyl; more preferably hydrogen;

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl cycloalkyl, substituted cycloalkyl, cycloalkenyl, substituted cycloalkenyl, heterocyclic, substituted heterocyclic, aryl, substituted aryl, heteroaryl, substituted heteroaryl, and —$SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl;

$R^7$ is selected from the group consisting of hydrogen, halogen, hydroxy, substituted amino, heterocycle, and substituted heterocyle;

$R^8$ is selected from the group consisting of substituted amino, heterocycle, and substituted heterocycle;

b is 1 or 2; and

A, B, $R^3$, $R^5$, and $R^6$ are as defined above; and enantiomers, diastereomers, pharmaceutically acceptable salts thereof.

Within these preferred groups, an even preferred group of compounds is represented by formula IIa" IIb", IIc", or IId":

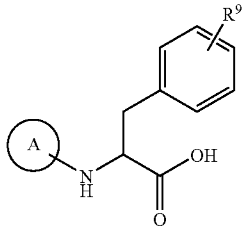

IIa″

-continued

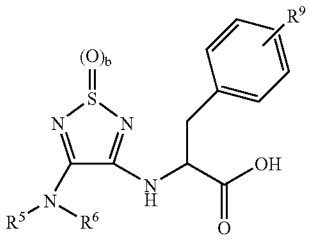

IIb″

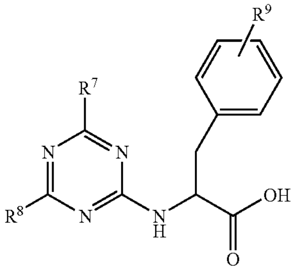

IIc″

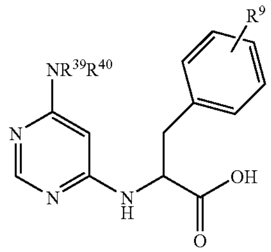

IId″ wherein:

A is 3-nitrothiophen-2-yl, 1-phenyltetrazol-5-yl, 1,5-dimethyl-4-nitropyazol-3-yl, 1-ethylpyrazol-5-yl, 4-phenylsulfonylthiophen-3-yl, 1,4-diphenylpyrazol-5-yl, 1-phenylimidazol-2-yl, or 5-benzoylmethylsulfinyl-4-(3-trifluoromethylphenyl) 1,2,4-triazol-3-yl;

$R^7$ is selected from the group consisting of hydrogen, hydroxy, chloro, and —$NR^{30}R^{31}$ wherein $R^{30}$ is hydrogen, alkyl, substituted alkyl, or alkenyl; and $R^{31}$ is alkyl, substituted alkyl, aryl, substituted aryl, heteroaryl, substituted heteroaryl, cycloalkyl, or —$SO_2R^{32}$ (wherein $R^{32'}$ is aryl or substituted aryl); or $R^{30}$ and $R^{31}$ together with the nitrogen atom to which they are attached form a heterocycle or substituted heterocycle, preferably $R^7$ is hydrogen, hydroxy, chloro, N-(2-methylpropyl)amino, N-(phenyl)amino, N-(benzyl)amino, N-(2-(4-methylphenyl)ethyl)amino, N-(2-(4-methoxyphenyl)ethyl)amino, N-(1-phenylethyl)amino, N-(4-chlorobenzyl)amino, N-(cyclopentyl)amino, N-(cyclohexyl)amino, N-(2-methylpropyl)amino, N-(5-methylisoxazol-3-yl)amino, N-(furan-2-ylmethyl)amino, N-(cyclohexylmethyl)amino, N-(4-aminosulfonyl-benzyl)amino, N-(3,4-methylenedioxy-benzyl)amino, N-(2-methyoxy-ethyl)-amino, N,N-bis-(2-methoxyethyl)amino, N-(2-propyl)-N-benzylamino, N-methyl-N-(2-phenylethyl)amino, N-methyl-N-[2-(3,4-dimethoxyphenyl)-ethyl]amino, N-ethyl-N-(pyridin-4-ylmethyl)-amino, N-methyl-N-(pyridin-3-ylmethyl)amino, N-ethyl-N-[2-(4-methoxyphenyl)-1-methylethyl-]amino, N-(4-aminosulfonylbenzyl)amino, N-methyl-N-(3-dimethylaminopropyl)amino, N,N-bis-benzylamino, N-methyl-N-[2-(pyridin-2-yl)ethyl]amino, N-methyl-N-benzylamino, N-[2-(1-methylpyrrolidin-2-yl)ethyl]

amino, N-furan-2-ylmethylamino, N,N-bis-propylamino, N-benzyl-N-(2-dimethylaminoethyl)-amino, N-(6-nitrobenzothiazol-2-yl)amino, piperidin-1-yl, N-(4-aminosulfonylbenzyl)amino, N-methyl-N-(4-methylphenylsulfonyl)-amino, or N-(2-(4-aminosulfonylphenyl)ethyl)amino;

$R^8$ is —$NR^{33}R^{34}$ wherein $R^{33}$ is hydrogen, alkyl, substituted alkyl, or aryl; and $R^{34}$ is alkyl, cycloalkyl, substituted alkyl, aryl, substituted aryl, heteroaryl, substituted heteroaryl, heterocycle substituted heterocycle, or —$SO_2R^{35}$ (wherein $R^{35}$ is substituted alkyl, aryl, substituted aryl, heteroaryl, substituted heteroaryl, heterocycle, or substituted heterocycle); or $R^{33}$ and $R^{34}$ together with the nitrogen atom to which they are attached form a heterocycle or substituted heterocycle; preferably $R^8$ is N-(5-methylisoxazol-3-yl) amino, N-(2-(1-methylpyrrolidin-2-yl)ethylamino, N-methyl-N-(2-pyridin-2-ylethyl)amino, N,N-bis-(2-methoxyethyl)amino, N-methyl-N-(2-pyridin-2-ylethyl)amino, N-methyl-N-(2-phenylethyl)amino, N-methyl-N-(2-(3,4-dimethoxyphenyl)ethyl)amino, N-(2-(4-methoxyphenyl) ethyl)amino, N-(2-methoxyethyl)amino, N-(furan-2-ylmethyl)amino, N-(4-aminosulfonylbenzyl)amino, N-(2-piperidin-1-ylethyl)amino, N-(2-(4-methylphenyl)-ethyl) amino, N-(1-phenylethyl)amino, N-(4-chlorobenzyl)amino, N-(2-propyl)-N-(benzyl)amino, N-methyl-N-(2-phenylethyl)amino, N-methyl-N-(2-(3,4-dimethoxyphenyl)ethyl) amino, N-ethyl-N-(pyridin-4-ylmethyl)amino, N-(benzyl)-N-(1-phenylethyl)amino, N-allyl-N-(cyclohexyl)amino, N-ethyl-N-(2-(4-methoxyphenyl)-1-methylethyl)amino, N-propyl-N-(4-nitronenzyl)-amino, N-methyl-N-(2-pyridin-2-ylethyl)amino, N,N-bis-(benzyl)amino, N-benzyl-N-(2-cyanoethyl)amino, N-benzyl-N-(2-dimethylaminoethyl) amino, N-ethyl-N-(3,4-dichlorobenzyl)amino, N-ethyl-N-(pyridin-4-ylmethyl)amino, N-methyl-N-(pyridin-3-ylmethyl)amino, N,N-bis-(pyridin-3-ylmethyl)amino, N,N-bis-benzylamino, N-benzyl-N-(2-cyanoethyl)amino, N-phenyl-N-(pyridin-2-yl)amino, N-methyl-N-(4-methylphenylsulfonyl)amino, N,N-bis-(cyclohexyl)amino, N-(2-phenyl-1-aminocarbonylethyl)amino, N-(2-phenyl-1,1-dimethylethyl)amino, N-(2-phenylethyl)amino, N-(2-(2-methoxyphenyl)-ethyl)amino, N-(2-(3,4-dimethoxyphenyl) ethyl)amino, N-(2-(4-fluorophenyl)-1,1-dimethylethyl) amino, N-(1-phenyl-2-(4-methylphenyl)ethyl)-amino, N-methyl-N-(2-(3,4-dimethoxyphenyl)ethyl)amino, N-methyl-N-(2-phenylethyl)amino, N-ethyl-N-(1-methyl-2-(4-methoxyphenyl)-ethyl)amino, N-benzyl-N-(1-phenyl)ethyl) amino, N-(pyridin-4-ylmethyl)-amino, N-(pyridin-3-ylmethyl)amino, N-(pyridin-2-ylmethyl)amino, N-2-(4-benzylpiperizin-1-yl)ethylamino, N-2-ethylhexyl-N-(pyridin-2-ylmethyl)-amino, N-(3,3-diphenylpropyl)amino, N-(2-pyridin-2-ylethyl)amino, N-(4-ethoxy-3-methoxyphenyl)ethylamino, N-(2-phenylpropyl)amino, N-(4-(piperazin-3,5-dione-1-sulfonylphenyl)amino, N,N-bis-methyl, N-(2-pyrrolidin-1-ylethyl)-amino, N-(phenyl-1-aminocarbonylethyl)amino, N-(2-phenyl-1,1-dimethylethyl)amino, N-(2-(4-fluorophenyl)-1,1-dimethylethyl)-amino, N-(1-phenyl-2-(2-methylphenyl)ethyl)amino, N-(3-imidazol-1-ylpropyl)amino, N-(2-morpholin-4-ylethyl) amino, N-(2-piperidin-1-ylethyl)amino, N-(2-pyrrolidin-1-ylethyl)amino, N-(1-ethoxycarbonyl-piperidin-4-yl)amino, N-(2-phenoxyethyl)amino, N-(3-pyrrolidin-1-ylpropyl) amino, N-(5-chloro-1,3-dimethylpyrazol-4-ylsulfonyl) amino, N-(benzylsulfonyl)amino, N-(2-carboxy-1-phenylethyl)amino, N-(1-phenyl-1-ethoxycarbonylmethyl)amino, N-benzyl-N-(1-carboxy-2-phenylethyl)amino, N-2-(4-benzylpiperazin-1-yl)ethylamino, N-(1-carboxy-3-phenylpropyl)-amino, 4-phenylpiperazin-1-yl, 4-acetylpiperazin-1-yl, piperidin-1-yl, 4-benzylpiperidin-1-yl, 2,5-dimethylpiperidin-1-yl, 4-cyclohexylpiperazin-1-yl, 4-(3,4-methylenedioxyphenylmethyl)-piperazin-1-yl, 4-(diphenylmethyl)-piperazin-1-yl, 3-methylpiperidin-1-yl, 2,6-dimethylmorpholin-4-yl, 2-(4-benzylpiperazin-1-yl)ethylamino, 4-(2-propylaminocarbonylmethyl)-piperazin-1-yl, 4-(1-phenylethyl)piperazin-1-yl, 4-(2-phenylethyl)piperazin-1-yl, 4-(furan-2-ylcarbonyl)piperazin-1-yl, 4-(1-phenylpropen-1-yl)piperazin-1-yl, 4-(2-morpholin-4-ylethyl)piperazin-1-yl, 1,2,3,4-tetrahydroisoquinolin-2-yl, 4-(ethoxycarbonylmethyl)piperazin-1-yl, piperazin-1-yl, 4-(2-methoxyethyl)piperazin-1-yl, 2-ethoxycarbonylpiperidin-1-yl, 2-ethoxycarbonylmethyl-3-oxopiperazin-1-yl, 3-(S)-ethoxycarbonyl-1,2,3,4-tetrahydroisoquinolin-2-yl, or 3-carboxy-1,2,3,4-tetrahydroisoquinolin-2-yl; $R^{39}$ is selected from the group consisting of hydrogen and alkyl; preferably hydrogen, methyl, or hexyl;

$R^{40}$ is selected from the group consisting of alkyl and substituted alkyl; or $R^{39}$ and $R^{40}$ together with the nitrogen atom to which they are attached form a heterocyclic or substituted heterocyclic ring; preferably methyl, hexyl, or 2-(3-methylphenylureido)ethyl; and $R^9$ selected from the group consisting of —O-Z-$NR^{11}R^{11'}$ and —O-Z-$R^{12}$ wherein Z is —C(O)— or —$SO_2$—; $R^{11}$ and $R^{11'}$ are independently selected from the group consisting of hydrogen, alkyl, substituted alkyl, cycloalkyl, substituted cycloalkyl, cycloalkenyl, substituted cycloalkenyl, heterocyclic, substituted heterocyclic and where $R^{11}$ and $R^{11'}$ are joined together to form a heterocyclic or substituted heterocyclic ring; and $R^{12}$ is selected from the group consisting of heterocycle and substituted heterocycle; preferably $R^9$ is —$OCON(CH_3)_2$ and is located at the 4-position of the phenyl, and $R^5$ and $R^6$ are as defined above; enantiomers, diastereomers, and pharmaceutically acceptable salts thereof.

Within above more preferred groups, particularly preferred compounds are those selected from compounds of formulae IIb" or IIc".

In another of its method aspects, this invention is directed to a method for treating a disease mediated by VLA-4 in a patient, which method comprises administering a pharmaceutical composition comprising a pharmaceutically acceptable carrier and a therapeutically effective amount of a compound of formula IVa and/or IVb:

IVa

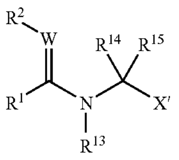

and

IVb

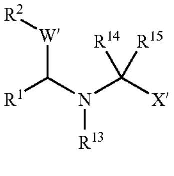

wherein, in formula IVa, $R^1$ and $R^2$, together with the carbon atom and W to which they are bound respectively, are joined to form an aryl, cycloalkenyl, heteroaryl or heterocyclic group having at least five atoms in the aryl, cycloalkenyl, heteroaryl or heterocyclic group and optionally containing or additionally containing in the case of heteroaryl and heterocyclic groups 1 to 3 heteroatoms selected from the group consisting of oxygen, nitrogen and sulfur, and wherein the heteroaryl or heterocyclic group is mono-cyclic;

in formula IVb, $R^1$ and $R^2$, together with the carbon atom and W' to which they are bound respectively, are joined to form a cycloalkyl, cycloalkenyl or heterocyclic group having at least five atoms in the cycloalkyl, cycloalkenyl or heterocyclic group and optionally containing or additionally containing in the case the heterocyclic group 1 to 3 heteroatoms selected from the group consisting of oxygen, nitrogen and sulfur, and wherein the heterocyclic group is mono-cyclic;

and further wherein said aryl, cycloalkyl, cycloalkenyl, heteroaryl or heterocyclic group of formula IVa or IVb is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where each R is independently hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, —$N[S(O)_2—R']_2$ and —$N[S(O)_2—NR']_2$ where each R' is independently selected from the group consisting of alkyl, substituted alkyl, aryl, substituted aryl, heteroaryl, substituted heteroaryl, heterocyclic and substituted heterocyclic;

$R^{13}$ is selected from the group consisting of hydrogen, $C_{1-10}$ alkyl, Cy, and Cy-$C_{1-10}$ alkyl, wherein alkyl is optionally substituted with one to four substituents independently selected from $R^a$; and Cy is optionally substituted with one to four substituents independently selected from $R^b$;

$R^{14}$ is selected from the group consisting of hydrogen, $C_{1-10}$ alkyl, $C_{2-10}$ alkenyl, $C_{2-10}$ alkynyl, Cy, Cy-$C_{1-10}$ alkyl Cy-$C_{2-10}$ alkenyl and Cy-$C_{2-10}$ alkynyl, wherein alkyl, alkenyl, and alkynyl are optionally substituted with one to four substituents selected from phenyl and $R^x$, and Cy is optionally substituted with one to four substituents independently selected from $R^y$;

or $R^{13}$, $R^{14}$ and the atoms to which they are attached together form a mono- or bicyclic ring containing 0-2 additional heteratoms selected from N, O and S;

$R^{15}$ is selected from the group consisting of $C_{1-10}$ alkyl, $C_{2-10}$ alkenyl, $C_{2-10}$ alkynyl, aryl, aryl-$C_{1-10}$ alkyl, heteroaryl, heteroaryl-$C_{1-10}$ alkyl, wherein alkyl, alkenyl and alkynyl are optionally substituted with one to four substituents selected from $R^x$, and aryl and heteroaryl are optionally substituted with one to four substituents independently selected from $R^y$;

or $R^{14}$, $R^{15}$ and the carbon to which they are attached form a 3-7 membered mono- or bicyclic ring containing 0-2 heteroatoms selected from N, O and S;

$R^a$ is selected from the group consisting of Cy and a group selected from $R^x$, wherein Cy is optionally substituted with one to four substituents independently selected from $R^c$:

$R^b$ is selected from the group consisting of $R^a$, $C_{1-10}$ alkyl, $C_{2-10}$ alkenyl, $C_{2-10}$ alkynyl, aryl $C_{1-10}$alkyl, heteroaryl $C_{1-10}$ alkyl, wherein alkyl, alkenyl, alkynyl, aryl, heteroaryl are optionally substituted with a group independently selected from $R^c$;

$R^c$ is selected from the group consisting of halogen, $NO_2$, $C(O)OR^f$, $C_{1-4}$ alkyl, $C_{1-4}$ alkoxy, aryl, aryl $C_{1-4}$ alkyl, aryloxy, heteroaryl, $NR^fR^g$, $R^fC(O)R^g$, $NR^fC(O)NR^fR^g$, and CN;

$R^d$ and $R^e$ are independently selected from hydrogen, $C_{1-10}$ alkyl, $C_{2-10}$ alkenyl, $C_{2-10}$ alkynyl, Cy and Cy $C_{1-10}$alkyl, wherein alkyl, alkenyl, alkynyl and Cy are optionally substituted with one to four substituents independently selected from $R^c$;

or $R^d$ and $R^e$ together with the atoms to which they are attached form a heterocyclic ring of 5 to 7 members containing 0-2 additional heteroatoms independently selected from oxygen, sulfur and nitrogen;

$R^f$ and $R^g$ are independently selected from hydrogen, $C_{1-10}$ alkyl, Cy and Cy-$C_{1-10}$ alkyl wherein Cy is optionally substituted with $C_{1-10}$ alkyl; or $R^f$ and $R^g$ together with the carbon to which they are attached form a ring of 5 to 7 members containing 0-2 heteroatoms independently selected from oxygen, sulfur and nitrogen;

$R^h$ is selected from the group consisting of hydrogen, $C_{1-10}$ alkyl, $C_{2-10}$ alkenyl, $C_{2-10}$ alkynyl, cyano, aryl, aryl $C_{1-10}$ alkyl, heteroaryl, heteroaryl $C_{1-10}$ alkyl, and —$SO_2R^1$; wherein alkyl, alkenyl, and alkynl are optionally substituted with one to four substitutents independently selected from $R^a$; and aryl and heteroaryl are each optionally substituted with one to four substituents independently selected from $R^b$;

$R^i$ is selected from the group consisting of $C_{1-10}$ alkyl, $C_{2-10}$ alkenyl, $C_{2-10}$ alkynyl, and aryl; wherein alkyl, alkenyl, alkynyl and aryl are each optionally substituted with one to four substituents independently selected from $R^c$;

$R^x$ is selected from the group consisting of —$OR^d$, —$NO_2$, halogen, —$S(O)_mR^d$, —$SR^d$, —$S(O)_2OR^d$, —$S(O)_mNR^dR^e$, —$NR^dR^e$, —$O(CR^fR^g)_nNR^dR^e$, $C(O)R^d$, —$CO_2R^d$, —$CO_2(CR^fR^g)_nCONR^dR^e$, —$OC(O)R^d$, —CN, —$C(O)NR^dR^e$, —$NR^dC(O)R^e$, —$OC(O)NR^dR^e$, —$NR^dC(O)OR^e$, —$NR^dC(O)NR^dR^e$, —$CR^d(N—OR^e)$, $CF_3$, oxo, $NR^dC(O)NR^dSO_2R^i$, $NR^dS(O)_mR^e$, —$OS(O)_2OR^d$, and —$OP(O)(OR^d)_2$;

$R^y$ is selected from the group consisting of $R^x$, $C_{1-10}$ alkyl, $C_{2-10}$ alkenyl, $C_{2-10}$ alkynyl, aryl $C_{1-10}$alkyl, heteroaryl $C_{1-10}$ alky, cycloalkyl, heterocyclyl; wherein alkyl, alkenyl, alkynyl and aryl are each optionally substituted with one to four substitutents independently selected from $R^x$;

Cy is cycloalkyl, heterocyclyl, aryl, or heteroaryl;

m is an integer from 1 to 2;

n is an integer from 1 to 10;

W is selected from the group consisting of carbon and nitrogen;

W' is selected from the group consisting of carbon, nitrogen, oxygen, sulfur, S(O) and $S(O)_2$;

X' is selected from the group consisting of —$C(O)OR^d$, —$P(O)(OR^d)(OR^e)$, —$P(O)(R^d)(OR^e)$, —$S(O)_mOR^d$, —$C(O)NR^dR^h$, and -5-tetrazolyl;

and enantiomers, diastereomers and pharmaceutically acceptable salts thereof; provided that:

(i) the compound of formula IVa or IVb has a binding affinity to VLA-4 as expressed by an $IC_{50}$ of about 15 μM or less; and (ii) in formula IVa and IVb, $R^1$ and $R^2$, together with the carbon atom and W to which they are bound respectively, do not form a substituted or unsubstituted pyridazine ring.

Preferably, in the above method, $R^1$ and $R^2$, together with the carbon atom and W to which they are bound respectively, are joined to form a substituted or unsubstituted monocyclic heteroaryl or heterocyclic ring wherein the heteroaryl ring contains 1 to 4 heteroatoms selected from N, O or S and the heterocyclic ring contains 1 to 3 heteroatoms selected from N, O, or S(O)n wherein n is 0 to 2, preferably $R^1$ and $R^2$, together with the carbon atom and W to which they are bound respectively, are joined to form substituted or unsubstituted pyrrole, pyrazole, imidazole, 1,2,3-triazole, 1,2,4-triazole, tetrazole, thiophene, pyridine, pyrimidine, 1,3,5-triazine, 1-oxo-1,2,5-thiadiazole or 1,1-dioxo-1,2,5-thiadiazole ring; more preferably, substituted 1,3,5-triazine, or 1,1-dioxo-1,2,5-thiadiazole ring.

Preferably, X' is —$C(O)OR^d$.

In a preferred embodiment, the above method employs a compound of formula Va, Vb, or Vc:

Va

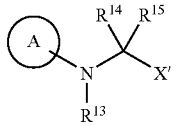

Vb

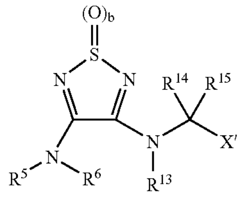

Vc

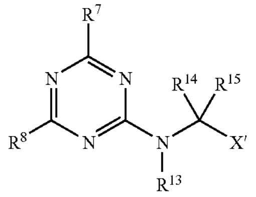

wherein:

ring A is selected from the group consisting of pyrrole, pyrazole, imidazole, pyrimidine, 1,2,3-triazole, 1,2,4-triazole, tetrazole, and thiophene wherein each of said pyrrole, pyrazole, imidazole, and thiophene ring is substituted with 1 to 3 substituent(s), and each of said pyrimidine, 1,2,3-triazole, 1,2,4-triazole, and tetrazole ring is substituted with 1 to 2 substituent(s), independently selected from the group consisting of alkyl, alkoxy, halogen, nitro, amino, substituted amino, aryl, substituted aryl, heteroaryl, substituted heteroaryl, heterocyle, substitued heterocycle, and —$SO_2R^5$ (wherein $R^5$ is alkyl, aryl, or substituted aryl);

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted-heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —$SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, and substituted heteroaryl;

$R^7$ is selected from the group consisting of hydrogen, halogen, hydroxy, substituted amino, heterocycle, and substituted heterocyle;

$R^8$ is selected from the group consisting of substituted amino, heterocycle, and substituted heterocycle;

b is 1 or 2; and $R^3$, $R^{14}$, $R^{15}$, and X' are as defined above.

In yet another of its method aspects, this invention is directed to a method for treating a disease mediated by VLA-4 in a patient, which method comprises administering a pharmaceutical composition comprising a pharmaceutically acceptable carrier and a therapeutically effective amount of a compound of formula VIa and/or VIb:

VIa

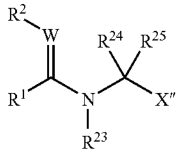

and

VIb

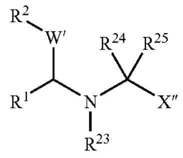

wherein, in formula VIa, $R^1$ and $R^2$, together with the carbon atom and W to which they are bound respectively, are joined to form an aryl, cycloalkenyl, heteroaryl or heterocyclic group having at least five atoms in the aryl, cycloalkenyl, heteroaryl or heterocyclic group and optionally containing or additionally containing in the case of heteroaryl and heterocyclic groups 1 to 3 heteroatoms selected from the group consisting of oxygen, nitrogen and sulfur, and wherein the heteroaryl or heterocyclic group is mono-cyclic;

in formula VIb, $R^1$ and $R^2$, together with the carbon atom and W' to which they are bound respectively, are joined to form a cycloalkyl, cycloalkenyl or heterocyclic group having at least five atoms in the cycloalkyl, cycloalkenyl or heterocyclic group and optionally containing or additionally containing in the case of the heterocyclic group 1 to 3 heteroatoms selected from the group consisting of oxygen, nitrogen and sulfur, and wherein the heterocyclic group is mono-cyclic;

and further wherein said aryl, cycloalkyl, cycloalkenyl, heteroaryl or heterocyclic group of formula VIa or VIb is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where each R is independently hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, —$N[S(O)_2—R']_2$ and —$N[S(O)_2—NR']_2$ where each R' is independently selected from the group consisting of alkyl, substituted alkyl, aryl, substituted aryl, heteroaryl, substituted heteroaryl, heterocyclic and substituted heterocyclic;

$R^{23}$ is selected from the group consisting of hydrogen, $C_{1-10}$ alkyl optionally substituted with one to four substituents independently selected from $R^{a'}$ and Cy optionally substituted with one to four substituents independently selected from $R^{b'}$;

$R^{24}$ is selected from the group consisting of $Ar^1—Ar^2—C_{1-10}$, alkyl, $Ar^1—Ar^2—C_{2-10}$ alkenyl, $Ar^1—Ar^2—C_{2-10}$ alkynyl, wherein $Ar^1$ and $Ar^2$ are independently aryl or heteroaryl each of which is optionally substituted with one to four substituents independently selected from $R^{b'}$; alkyl, alkenyl and alkynyl are optionally substituted with one to four substituents independently selected from $R^{a'}$;

$R^{25}$ is selected from the group consisting of hydrogen, $C_{1-10}$ alkyl, $C_{2-10}$ alkenyl, $C_{2-10}$ alkynyl, aryl, aryl $C_{1-10}$alkyl, heteroaryl, and heteroaryl $C_{1-10}$ alkyl, wherein alkyl, alkenyl and alkynyl are optionally substituted with one to four substituents selected from $R^{a'}$, and aryl and heteroaryl are optionally substituted with one to four substituents independently selected from $R^{b'}$;

$R^{a'}$ is selected from the group consisting of Cy, $OR^{d'}$, —$NO_2$, halogen $S(O)_mR^{d'}$, $SR^{d'}$, —$S(O)_2OR^{d'}$, —$S(O)_m$ $NR^{d'}R^{e'}$, —$NR^{d'}R^{e'}$, —$O(CR^{f'}R^{g'})_nNR^{d'}R^{e'}$, $C(O)R^{d'}$, $CO_2R^{d'}$, —$CO_2(CR^{f'}R^{g'})_nCONR^{d'}R^{e'}$, —$OC(O)R^{d'}$, —CN, —$C(O)NR^{d'}R^{e'}$, —$NR^{d'}C(O)R^{e'}$, —$OC(O)NR^{d'}R^{e'}$, —$NR^{d'}C(O)OR^{e'}$, —$NR^{d'}C(O)NR^{d'}R^{e'}$, —$CR^{d'}(N—OR^{e'})$, $CF_3$, and —$OCF_3$;

wherein Cy is optionally substituted with one to four substituents independently selected from $R^{c'}$;

$R^{b'}$ is selected from the group consisting of $R^{a'}$, $C_{1-10}$ alkyl, $C_{2-10}$ alkenyl, $C_{2-10}$ alkynyl, aryl $C_{1-10}$ alkyl, heteroaryl $C_{1-10}$alkyl, wherein alkyl, alkenyl, aryl, heteroaryl are optionally substituted with a group independently selected from $R^{c'}$;

$R^{c'}$ is selected from the group consisting of halogen, amino, carboxy, $C_{1-4}$ alkyl, $C_{1-4}$ alkoxy, aryl, aryl $C_{1-4}$alkyl, hydroxy, $CF_3$, and aryloxy;

$R^{d'}$ and $R^{e'}$ are independently selected from hydrogen, $C_{1-10}$ alkyl, $C_{2-10}$ alkenyl, $C_{2-10}$ alkynyl, Cy and Cy $C_{1-10}$alkyl, wherein alkyl, alkenyl, alkynyl and Cy are optionally substituted with one to four substituents independently selected from $R^{c'}$; or $R^{d'}$ and $R^{e'}$ together with the atoms to which they are attached form a heterocyclic ring of 5 to 7 members containing 0-2 additional heteroatoms independently selected from oxygen, sulfur and nitrogen;

$R^{f'}$ and $R^{g'}$ are independently selected from hydrogen, $C_{1-10}$ alkyl, Cy and Cy-$C_{1-10}$ alkyl; or $R^{f'}$ and $R^{g'}$ together with the carbon to which they are attached form a ring of 5 to 7 members containing 0-2 heteroatoms independently selected from oxygen, sulfur and nitrogen;

$R^{h'}$ is selected from the group consisting of hydrogen, $C_{1-10}$ alkyl, $C_{2-10}$ alkenyl, $C_{2-10}$ alkynyl, cyano, aryl, aryl $C_{1-10}$ alkyl, heteroaryl, heteroaryl $C_{1-10}$ alkyl, or —$SO_2R^{i'}$;

wherein alkyl, alkenyl, and alkynyl are optionally substituted with one to four substitutents independently selected from $R^{a'}$; and aryl and heteroaryl are each optionally substituted with one to four substituents independently selected from $R^{b'}$;

$R^{i'}$ is selected from the group consisting of $C_{1-10}$ alkyl, $C_{2-10}$ alkenyl, $C_{2-10}$ alkynyl, and aryl;

wherein alkyl, alkenyl, alkynyl and aryl are each optionally substituted with one to four substituents independently selected from $R^{c'}$;

Cy is cycloalkyl, heterocyclyl, aryl, or heteroaryl;

X" is selected from the group consisting of —$C(O)OR^{d'}$, —$P(O)(OR^{d'})(OR^{e'})$, —$P(O)(R^{d'})(OR^{e'})$, —$S(O)_mOR^{d'}$, —$C(O)NR^{d'}R^{h'}$, and -5-tetrazolyl;

m is an integer from 1 to 2;

n is an integer from 1 to 10;

and enantiomers, diastereomers and pharmaceutically acceptable salts thereof; provided that:

(i) the compound of formula VIa or VIb has a binding affinity to VLA-4 as expressed by an $IC_{50}$ of about 15 μM or less; and (ii) in formula VIa and VIb, $R^1$ and $R^2$, together with the carbon atom and W to which they are bound respectively, do not form a substituted or unsubstituted pyridazine ring.

Preferably, in the above method, X" is —$C(O)OR^{d'}$.

Preferably, $R^1$ and $R^2$, together with the carbon atom and W to which they are bound respectively, are joined to form a substituted or unsubstituted monocyclic heteroaryl or heterocyclic group wherein the heteroaryl aryl group has 1 to 4 heteroatoms selected from the group consisting of N, O, or S and the heterocyclic group contains 1 to 3 heteroatoms selected from the group consisting of N, O, or S(O)n wherein n is 0 to 2.

Preferably, $R^{24}$ is —$CH_2$—$Ar^2$—$Ar^1$ and $R^{25}$ is hydrogen.

In a preferred embodiment, the above method employs a compound of formula VIIa, VIIb, or VIIc:

VIIa

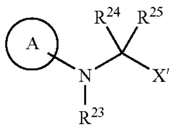

VIIb

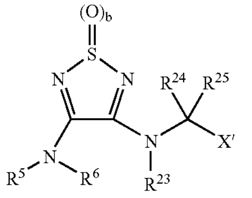

VIIc

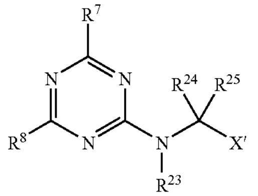

wherein:

ring A is selected from the group consisting of pyrrole, pyrazole, imidazole, pyrimidine, 1,2,3-triazole, 1,2,4-triazole, tetrazole, and thiophene wherein each of said pyrrole, pyrazole, imidazole, and thiophene ring is substituted with 1 to 3 substituent(s), and each of said pyrimidine, 1,2,3-triazole, 1,2,4-triazole, and tetrazole ring is substituted with 1 to 2 substituent(s), independently selected from the group consisting of alkyl, alkoxy, halogen, nitro, amino, substituted amino, aryl, substituted aryl, heteroaryl, substituted heteroaryl, heterocyle, substitued heterocycle, and —$SO_2R^a$ (wherein $R^a$ is alkyl, aryl, or substituted aryl);

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —$SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, and substituted heteroaryl;

$R^7$ is selected from the group consisting of hydrogen, halogen, hydroxy, substituted amino, heterocycle, and substituted heterocyle;

$R^8$ is selected from the group consisting of substituted amino, heterocycle, and substituted heterocycle;

b is 1 or 2; and $R^{23}$, $R^{24}$, $R^{25}$, and X' are as defined above.

The compounds and pharmaceutical compositions of this invention are useful for treating VLA-4 mediated disease conditions. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Other disease conditions include, but are not limited to, inflammatory conditions such as erythema nodosum, allergic conjunctivitis, optic neuritis, uveitis, allergic rhinitis, Ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

In a preferred embodiment, the disease mediated by VLA-4 is an inflammatory disease.

The present invention is also directed to novel compounds useful for treating a disease mediated by VLA-4. Accordingly, in one of its composition aspects, this invention is directed to a compound of formula Ia and Ib:

Ia

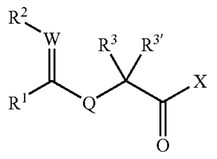

and

Ib

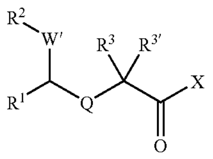

wherein, in formula Ia, $R^1$ and $R^2$, together with the carbon atom and W to which they are bound respectively, are joined to form an aryl, cycloalkenyl, heteroaryl or heterocyclic group having at least five atoms in the aryl, cycloalkenyl, heteroaryl or heterocyclic group and optionally containing or additionally containing in the case of heteroaryl and heterocyclic groups 1 to 3 heteroatoms selected from the group consisting of oxygen, nitrogen and sulfur, and wherein the heteroaryl or heterocyclic group is mono-cyclic;

in formula Ib, $R^1$ and $R^2$, together with the carbon atom and W' to which they are bound respectively, are joined to form a cycloalkyl, cycloalkenyl or heterocyclic group having at least five atoms in the cycloalkyl, cycloalkenyl or heterocyclic group and optionally containing or additionally containing in the case of the heterocyclic group 1 to 3 heteroatoms selected from the group consisting of oxygen, nitrogen and sulfur, and wherein the heterocyclic group is mono-cyclic;

and further wherein said aryl, cycloalkyl, cycloalkenyl, heteroaryl or heterocyclic group of formula Ia or Ib is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where each R is independently hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, —$N[S(O)^2$—$R']_2$ and —$N[S(O)_2$—$NR']_2$ where each R' is independently selected from the group consisting of alkyl, substituted alkyl, aryl, substituted aryl, heteroaryl, substituted heteroaryl, heterocyclic and substituted heterocyclic;

$R^3$ is —$(CH_2)_x$—Ar—$R^9$, where Ar is aryl, substituted aryl, heteroaryl and substituted heteroaryl; $R^9$ is selected from the group consisting of acyl, acylamino, acyloxy, aminoacyl, aminocarbonylamino, aminothiocarbonylamino, aminocarbonyloxy, oxycarbonylamino, oxythiocarbonylamino, thioamidino, thiocarbonylamino, aminosulfonylamino, aminosulfonyloxy, aminosulfonyl, oxysulfonylamino and oxysulfonyl, x is an integer from 0 to 4;

$R^{3'}$ is selected from the group consisting of hydrogen, isopropyl, —$CH_2Z$ wherein Z is hydrogen, hydroxy, acylamino, alkyl, alkoxy, aryloxy, aryl, arloxyaryl, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted alkyl, substituted alkoxy, substituted aryl, substituted aryloxy, substituted aryloxyaryl, substituted cycloalkyl, heteroaryl, substituted heteroaryl, heterocyclic, or substituted heterocyclic;

Q is selected from the group consisting of —O—, —S—, —S(O)—, —$S(O)_2$, and —$NR^4$—;

$R^4$ is selected from the group consisting of hydrogen, alkyl, substituted alkyl, alkenyl, substituted alkenyl, cycloalkyl, substituted cycloalkyl, cycloalkenyl, substituted cycloalkenyl, aryl, substituted aryl, heteroaryl, substituted heteroaryl, heterocyclic and substituted heterocyclic or, optionally, $R^4$ and $R^1$ or $R^4$ and $R^2$, together with the atoms to which they are bound, are joined to form a heteroaryl, a substituted heteroaryl, a heterocyclic or a substituted heterocyclic group;

W is selected from the group consisting of nitrogen and carbon; and

W' is selected from the group consisting of nitrogen, carbon, oxygen, sulfur, S(O), and $S(O)_2$;

X is selected from the group consisting of hydroxyl, alkoxy, substituted alkoxy, alkenoxy, substituted alkenoxy, cycloalkoxy, substituted cycloalkoxy, cycloalkenoxy, substituted cycloalkenoxy, aryloxy, substituted aryloxy, heteroaryloxy, substituted heteroaryloxy, heterocyclyloxy, substituted heterocyclyloxy and —NR"R" where each R" is independently selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic and substituted heterocyclic;

and enantiomers, diasteromers and pharmaceutically acceptable salts thereof; provided that:

(i) the compound of formula Ia or Ib has a binding affinity to VLA-4 as expressed by an $IC_{50}$ of about 15 μM or less; and (ii) in formula Ia and Ib, $R^1$ and $R^2$, together with the carbon atom and W to which they are bound respectively, do not form a substituted or unsubstituted pyridazine ring.

Preferably, in the above compounds, $R^3$ is a group of the formula:

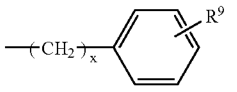

wherein $R^9$ and x are as defined herein. Preferably, $R^9$ is in the para position of the phenyl ring; and x is an integer from 1 to 4, more preferably x is 1.

Preferably, $R^9$ is selected from the group consisting of —O-Z-$NR^{11}R^{11'}$ and —O-Z-$R^{12}$ wherein $R^{11}$ and $R^{11'}$ are independently selected from the group consisting of hydrogen, alkyl, substituted alkyl, cycloalkyl, substituted cycloalkyl, cycloalkenyl, substituted cycloalkenyl, heterocyclic, substituted heterocyclic, and where $R^{11}$ and $R^{11'}$ are joined to form a heterocycle or a substituted heterocycle, $R^{12}$ is selected from the group consisting of heterocycle and substituted heterocycle, and Z is selected from the group consisting of —C(O)— and —$SO_2$—, preferably Z is —C(O)—. More preferably, $R^9$ is —$OC(O)NR^{11}R^{11'}$, wherein $R^{11}$ and $R^{11'}$ are as defined herein, even more preferably $R^9$ is —$OC(O)N(CH_3)_2$.

Preferably, in the above compounds, Q is —$NR^4$— wherein $R^4$ is hydrogen or alkyl, preferably hydrogen.

In another preferred embodiment, this invention is directed to compounds of formula IIa, IIb, or IIc:

IIa

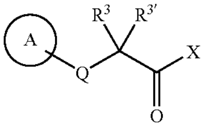

-continued

IIb

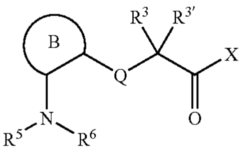

IIc

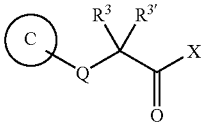

wherein:

ring A is a substituted or unsubstituted monocyclic heteroaryl ring containing 1 to 4 heteroatoms selected from the group consisting of N, O, or S, preferably ring A is selected from the group consisting of pyrrole, pyrazole, imidazole, pyrimidine, 1,2,3-triazole, 1,2,4-triazole, tetrazole, and thiophene wherein each of said pyrrole, pyrazole, imidazole, and thiophene ring is substituted with 1 to 3 substituent(s), and each of said pyrimidine, 1,2,3-triazole, 1,2,4-triazole, and tetrazole ring is substituted with 1 to 2 substituent(s), independently selected from the group consisting of alkyl, alkoxy, halogen, nitro, amino, substituted amino, aryl, substituted aryl, heteroaryl, substituted heteroaryl, heterocyle, substitued heterocycle, and —$SO_2R^5$ (wherein $R^5$ is alkyl, aryl, or substituted aryl);

ring B forms a 1-oxo-1,2,5-thiadiazole or a 1,1-dioxo-1,2,5-thiadiazole ring;

ring C is a substituted or unsubstituted monocyclic heteroaryl ring containing 1 to 3 heteroatoms selected from the group consisting of N, O, or S, preferably ring C is pyridine or 1,3,5-triazine ring wherein each of said ring is substituted with 1 or 2 substituent(s) independently selected from the group consisting of alkyl, substituted alkyl, alkoxy, halogen, hydroxy, amino, substituted amino, aryl, substituted aryl, heteroaryl, substituted heteroaryl, heterocyle, and substitued heterocycle;

$R^3$ is —$(CH_2)_x$—Ar—$R^9$, where Ar is aryl, substituted aryl, heteroaryl and substituted heteroaryl; $R^9$ is selected from the group consisting of acyl, acylamino, acyloxy, aminoacyl, aminocarbonylamino, aminothiocarbonylamino, aminocarbonyloxy, oxycarbonylamino, oxythiocarbonylamino, thioamidino, thiocarbonylamino, aminosulfonylamino, aminosulfonyloxy, aminosulfonyl, oxysulfonylamino and oxysulfonyl; x is an integer from 0 to 4;

$R^{3'}$ is selected from the group consisting of hydrogen, isopropyl, —$CH_2Z$ wherein Z is hydrogen, hydroxy, acylamino, alkyl, alkoxy, aryloxy, aryl, arloxyaryl, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted alkyl, substituted alkoxy, substituted aryl, substituted aryloxy, substituted aryloxyaryl, substituted cycloalkyl, heteroaryl, substituted heteroaryl, heterocyclic, or substituted heterocyclic;

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —$SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl;

or optionally, one of, $R^4$ and ring B, $R^4$ and $R^5$, $R^4$ and $R^6$, or $R^5$ and $R^6$, together with the atoms to which they are bound, can be joined to form a heterocyclic or substituted heterocyclic ring; and Q and X are as defined above.

Within the above preferred group, a more preferred group of compounds is represented by formula IIa', IIb', or IIc':

IIa'

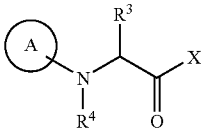

IIb'

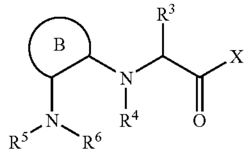

IIc'

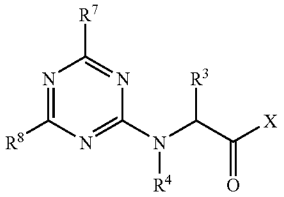

wherein:

$R^4$ is hydrogen or alkyl;

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —$SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl;

$R^7$ is selected from the group consisting of hydrogen, halogen, hydroxy, substituted amino, heterocycle, and substituted heterocyle;

$R^8$ is selected from the group consisting of substituted amino, heterocycle, and substituted heterocycle;

b is 1 or 2; and

A, B, $R^3$, and X are as defined above.

Within this more preferred group, an even more preferred group of compounds is represented by formula IIa", IIb", IIc", or IId":

IIa"

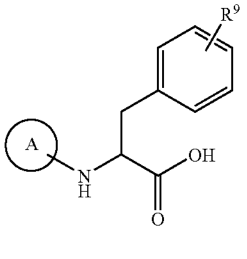

IIb"

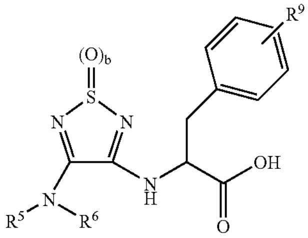

IIc"

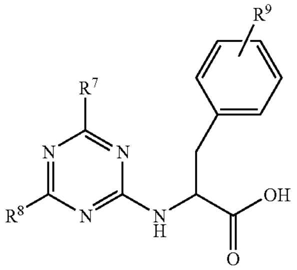

IId"

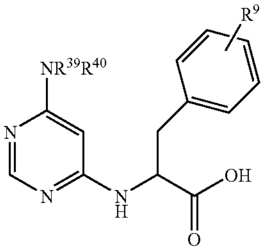

wherein:

A is 3-nitrothiophen-2-yl, 1-phenyltetrazol-5-yl, 1,5-dimethyl-4-nitropyazol-3-yl, 1-ethylpyrazol-5-yl, 4-phenylsulfonylthiophen-3-yl, 1,4-diphenylpyrazol-5-yl, 1-phenylimidazol-2-yl, or 5-benzoylmethylsulfinyl-4-(3-trifluoromethylphenyl)-1,2,4-triazol-3-yl;

$R^7$ is selected from the group consisting of hydrogen, hydroxy, chloro, and —$NR^{30}R^{31}$ wherein $R^{30}$ is hydrogen, alkyl, substituted alkyl, or alkenyl; and $R^{31}$ is alkyl, substituted alkyl, aryl, substituted aryl, heteroaryl, substituted heteroaryl, cycloalkyl, or —$SO_2R^{32}$ (wherein $R^{32}$ is aryl or substituted aryl); or $R^{30}$ and $R^{31}$ together with the nitrogen atom to which they are attached form a heterocycle or substituted heterocycle; preferably $R^7$ is hydrogen, hydroxy, chloro, N-(2-methylpropyl)amino, N-(phenyl)amino, N-(benzyl)amino, N-(2-(4-methylphenyl)ethyl)amino, N-(2-(4-methoxyphenyl)ethyl)amino, N-(1-phenylethyl)amino, N-(4-chlorobenzyl)-amino, N-(cyclopentyl)amino, N-(cyclohexyl)amino, N-(2-methylpropyl)-amino, N-(5-methylisoxazol-3-yl)amino, N-(furan-2-ylmethyl)amino, N-(cyclohexylmethyl)amino, N-(4-aminosulfonyl-benzyl)amino, N-(3,4-methylenedioxybenzyl)amino, N-(2-methyoxyethyl)-amino, N,N-bis-(2-methoxyethyl)amino, N-(2-propyl)-N-benzylamino, N-methyl-N-(2-phenylethyl)amino, N-methyl-N-[2-(3,4-dimethoxyphenyl)-ethyl]amino, N-ethyl-N-(pyridin-4-ylmethyl)amino, N-methyl-N-(pyridin-3-ylmethyl)amino, N-ethyl-N-[2-(4-methoxyphenyl)-1-methylethyl]amino, N-(4-aminosulfonylbenzyl)amino, N-methyl-N-(3-dimethylaminopropyl)amino, N,N-bis-benzylamino, N-methyl-N-[2-(pyridin-2-yl)ethyl]amino, N-methyl-N-benzylamino, N-[2-(1-methylpyrrolidin-2-yl)ethyl]amino, N-furan-2-ylmethylamino, N,N-bis-propylamino, N-benzyl-N-(2-dimethylamino-ethyl)-amino, N-(6-nitrobenzothiazol-2-yl)amino, piperidin-1-yl, N-(4-aminosulfonylbenzyl)amino, N-methyl-N-(4-methylphenylsulfonyl)-amino, or N-(2-(4-aminosulfonylphenyl)ethyl)amino;

$R^8$ is —$NR^{33}R^{34}$ wherein $R^{33}$ is hydrogen, alkyl, substituted alkyl, or aryl; and $R^{34}$ is alkyl, cycloalkyl, substituted alkyl, aryl, substituted aryl, heteroaryl, substituted heteroaryl, heterocycle substituted heterocycle, or —$SO_2R^{35}$ (wherein $R^{35}$ is substituted alkyl, aryl, substituted aryl, heteroaryl, substituted heteroaryl, heterocycle, or substituted heterocycle); or $R^{33}$ and $R^{34}$ together with the nitrogen atom to which they are attached form a heterocycle or substituted heterocycle; preferably $R^8$ is N-(5-methylisoxazol-3-yl)amino, N-(2-(1-methylpyrrolidin-2-yl)ethylamino, N-methyl-N-(2-pyridin-2-ylethyl)amino, N,N-bis-(2-methoxyethyl)amino, N-methyl-N-(2-pyridin-2-ylethyl)amino, N-methyl-N-(2-phenylethyl)amino, N-methyl-N-(2-(3,4-dimethoxyphenyl)ethyl)amino, N-(2-(4-methoxyphenyl)ethyl)amino, N-(2-methoxyethyl)amino, N-(furan-2-ylmethyl)amino, N-(4-aminosulfonyl-benzyl)amino, N-(2-piperidin-1-ylethyl)amino, N-(2-(4-methylphenyl)ethyl)-amino, N-(1-phenylethyl)amino, N-(4-chlorobenzyl)amino, N-(2-propyl)-N-(benzyl)amino, N-methyl-N-(2-phenylethyl)amino, N-methyl-N-(2-(3,4-dimethoxyphenyl)ethyl)amino, N-ethyl-N-(pyridin-4-ylmethyl)amino, N-(benzyl)-N-(1-phenylethyl)amino, N-allyl-N-(cyclohexyl)amino, N-ethyl-N-(2-(4-methoxyphenyl)-1-methylethyl)amino, N-propyl-N-(4-nitronenzyl)-amino, N-methyl-N-(2-pyridin-2-ylethyl)amino, N,N-bis-(benzyl)amino, N-benzyl-N-(2-cyanoethyl)amino, N-benzyl-N-(2-dimethylaminoethyl)amino, N-ethyl-N-(3,4-dichlorobenzyl)amino, N-ethyl-N-(pyridin-4-ylmethyl)amino, N-methyl-N-(pyridin-3-ylmethyl)amino, N,N-bis-(pyridin-3-ylmethyl)amino, N,N-bis-benzylamino, N-benzyl-N-(2-cyanoethyl)amino, N-phenyl-N-(pyridin-2-yl)amino, N-methyl-N-(4-methylphenylsulfonyl)amino, N,N-bis-(cyclohexyl)amino, N-(2-phenyl-1-aminocarbonylethyl)amino, N-(2-phenyl-1,1-dimethylethyl)amino, N-(2-phenylethyl)amino, N-(2-(2-methoxyphenyl)-ethyl)amino, N-(2-(3,4-dimethoxyphenyl)ethyl)amino, N-(2-(4-fluorophenyl)-1,1-dimethylethyl)amino, N-(1-phenyl-2-(4-methylphenyl)-ethyl)amino, N-methyl-N-(2-(3,4-dimethoxyphenyl)ethyl)amino, N-methyl-N-(2-phenylethyl)amino, N-ethyl-N-(1-methyl-2-(4- methoxyphenyl)-ethyl)amino, N-benzyl-N-(1-phenyl) ethyl)amino, N-(pyridin-4-ylmethyl)-amino, N-(pyridin-3-ylmethyl)amino, N-(pyridin-2-ylmethyl) amino, N-2-(4-benzylpiperizin-1-yl)ethylamino, N-2-ethylhexyl-N-(pyridin-2-ylmethyl)-amino, N-(3,3-diphenylpropyl)amino, N-(2-pyridin-2-ylethyl)amino, N-(4-ethoxy-3-methoxyphenyl)ethylamino, N-(2-phenylpropyl)amino, N-(4-(piperazin-3,5-dione-1-sulfonylphenyl)amino, N,N-bis-methyl, N-(2-pyrrolidin-1-ylethyl)amino, N-(phenyl-1-aminocarbonylethyl) amino, N-(2-phenyl-1,1-dimethylethyl)amino, N-(2-(4-fluorophenyl)-1,1-dimethylethyl)-amino, N-(1-phenyl-2-(2-methylphenyl)ethyl)amino, N-(3-imidazol-1-ylpropyl)amino, N-(2-morpholin-4-ylethyl)amino, N-(2-piperidin-1-ylethyl)-amino, N-(2-pyrrolidin-1-yl-ethyl)amino, N-(1-ethoxycarbonyl-piperidin-4-yl) amino, N-(2-phenoxyethyl)amino, N-(3-pyrrolidin-1-ylpropyl)-amino, N-(5-chloro-1,3-dimethylpyrazol-4-ylsulfonyl)amino, N-(benzylsulfonyl)amino, N-(2-carboxy-1-phenylethyl)amino, N-(1-phenyl-1-ethoxycarbonylmethyl)-amino, N-benzyl-N-(1-carboxy-2-phenylethyl)amino, N-2-(4-benzylpiperazin-1-yl)ethylamino, N-(1-carboxy-3-phenylpropyl)-amino, 4-phenylpiperazin-1-yl, 4-acetylpiperazin-1-yl, piperidin-1-yl, 4-benzylpiperidin-1-yl, 2,5-dimethylpiperidin-1-yl, 4-cyclohexylpiperazin-1-yl, 4-(3,4-methylenedioxy-phenylmethyl)piperazin-1-yl, 4-(diphenylmethyl)-piperazin-1-yl, 3-methyl-piperidin-1-yl, 2,6-dimethylmorpholin-4-yl, 2-(4-benzylpiperazin-1-yl)-ethylamino, 4-(2-propylaminocarbonylmethyl)-piperazin-1-yl, 4-(1-phenylethyl)piperazin-1-yl, 4-(2-phenylethyl)piperazin-1-yl, 4-(furan-2-ylcarbonyl)-piperazin-1-yl, 4-(1-phenylpropen-1-yl)piperazin-1-yl, 4-(2-morpholin-4-ylethyl)piperazin-1-yl, 1,2,3,4-tetrahydroisoquinolin-2-yl, 4-(ethoxy-carbonylmethyl)piperazin-1-yl, piperazin-1-yl, 4-(2-methoxyethyl)piperazin-1-yl, 2-ethoxycarbonylpiperidin-1-yl, 2-ethoxycarbonylmethyl-3-oxo-piperazin-1-yl, 3-(S)-ethoxycarbonyl-1,2,3,4-tetrahydroisoquinolin-2-yl, or 3-carboxy-1,2,3,4-tetrahydroisoquinolin-2-yl; $R^{39}$ is selected from the group consisting of hydrogen and alkyl;

$R^{40}$ is selected from the group consisting of alkyl and substituted alkyl; or $R^{39}$ and $R^{40}$ together with the nitrogen atom to which they are attached form a heterocyclic or substituted heterocyclic ring; and $R^9$ selected from the group consisting of —O-Z-$NR^{11}R^{11'}$ and —O-Z-$R^{12}$ wherein Z is —C(O)— or —$SO_2$—; $R^{11}$ and $R^{11'}$ are independently selected from the group consisting of hydrogen, alkyl, substituted alkyl, cycloalkyl, substituted cycloalkyl, cycloalkenyl, substituted cycloalkenyl, heterocyclic, substituted heterocyclic and where $R^{11}$ and $R^{11'}$ are joined together to form a heterocyclic or substituted heterocyclic ring; and $R^{12}$ is selected from the group consisting of heterocycle and substituted heterocycle; preferably $R^9$ is —OCON$(CH_3)_2$ and is located at the 4-position of the phenyl, and $R^5$ and $R^6$ are as defined above; enantiomers, diastereomers, pharmaceutically acceptable salts thereof.

In another of its composition aspects, this invention is directed to a compound of formula IVa:

IVa

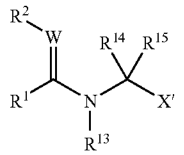

wherein $R^1$ and $R^2$, together with the carbon atom and W to which they are bound respectively, are joined to form a monocyclic heteroaryl ring having 1 to 4 heteroatoms in the ring selected from the group nitrogen or sulfur; or a monocyclic heterocyclic ring having 1 to 3 hetereoatoms in the ring selected from the group consisting of nitrogen, oxygen, or S(O)n (wherein n is o to 2);

and further wherein said heteroaryl or heterocyclic ring is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where each R is independently hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, —$N[S(O)_2—R']_2$ and —$N[S(O)_2—NR']_2$ where each R' is independently selected from the group consisting of alkyl, substituted alkyl, aryl, substituted aryl, heteroaryl, substituted heteroaryl, heterocyclic and substituted heterocyclic;

$R^{13}$ is selected from the group consisting of hydrogen, $C_{1-10}$ alkyl, Cy, and Cy-$C_{1-10}$ alkyl, wherein alkyl is optionally substituted with one to four substituents independently selected from $R^a$; and Cy is optionally substituted with one to four substituents independently selected from $R^b$;

$R^{14}$ is selected from the group consisting of hydrogen, $C_{1-10}$ alkyl, $C_{2-10}$ alkenyl, $C_{2-10}$ alkynyl, Cy, Cy-$C_{1-10}$ alkyl, Cy-$C_{1-10}$ alkenyl and Cy-$C_{2-10}$ alkynyl, wherein alkyl, alkenyl, and alkynyl are optionally substituted with one to four substituents selected from phenyl and $R^x$, and Cy is optionally substituted with one to four substituents independently selected from $R^y$;

or $R^{13}$, $R^{14}$ and the atoms to which they are attached together form a mono- or bicyclic ring containing 0-2 additional heteratoms selected from N, O and S;

$R^{15}$ is selected from the group consisting of $C_{1-10}$ alkyl, $C_{2-10}$ alkenyl, $C_{2-10}$ alkynyl, aryl, aryl-$C_{1-10}$ alkyl, heteroaryl, heteroaryl-$C_{1-10}$ alkyl, wherein alkyl, alkenyl and alkynyl are optionally substituted with one to four substituents selected from $R^x$, and aryl and heteroaryl are optionally substituted with one to four substituents independently selected from $R^y$;

or $R^{14}$, $R^{15}$ and the carbon to which they are attached form a 3-7 membered mono- or bicyclic ring containing 0-2 heteroatoms selected from N, O and S;

$R^a$ is selected from the group consisting of Cy and a group selected from $R^x$, wherein Cy is optionally substituted with one to four substituents independently selected from $R^c$:

$R^b$ is selected from the group consisting of $R^a$, $C_{1-10}$ alkyl, $C_{2-10}$ alkenyl, $C_{2-10}$ alkynyl, aryl $C_{1-10}$alkyl, heteroaryl $C_{1-10}$ alkyl, wherein alkyl, alkenyl, alkynyl, aryl, heteroaryl are optionally substituted with a group independently selected from $R^c$;

$R^c$ is selected from the group consisting of halogen, $NO_2$, $C(O)OR^f$, $C_{1-4}$ alkyl, $C_{1-4}$ alkoxy, aryl, aryl $C_{1-4}$alkyl, aryloxy, heteroaryl, $NR^fR^g$, $R^fC(O)R^g$, $NR^fC(O)NR^fR^g$, and CN;

$R^d$ and $R^e$ are independently selected from hydrogen, $C_{1-10}$ alkyl, $C_{2-0}$ alkenyl, $C_{2-10}$ alkynyl, Cy and Cy $C_{1-10}$alkyl, wherein alkyl, alkenyl, alkynyl and Cy are optionally substituted with one to four substituents independently selected from $R^c$;

or $R^d$ and $R^e$ together with the atoms to which they are attached form a heterocyclic ring of 5 to 7 members containing 0-2 additional heteroatoms independently selected from oxygen, sulfur and nitrogen;

$R^f$ and $R^g$ are independently selected from hydrogen, $C_{1-10}$ alkyl, Cy and Cy-$C_{1-10}$ alkyl wherein Cy is optionally substituted with $C_{1-10}$ alkyl; or $R^f$ and $R^g$ together with the carbon to which they are attached form a ring of 5 to 7 members containing 0-2 heteroatoms independently selected from oxygen, sulfur and nitrogen;

$R^h$ is selected from the group consisting of hydrogen, $C_{1-10}$ alkyl, $C_{2-10}$ alkenyl, $C_{2-10}$ alkynyl, cyano, aryl, aryl $C_{1-10}$ alkyl, heteroaryl, heteroaryl $C_{1-10}$ alkyl, and $—SO_2R^i$; wherein alkyl, alkenyl, and alkynl are optionally substituted with one to four substitutents independently selected from $R^a$; and aryl and heteroaryl are each optionally substituted with one to four substituents independently selected from $R^b$;

$R^i$ is selected from the group consisting of $C_{1-10}$ alkyl, $C_{2-10}$ alkenyl, $C_{2-10}$ alkynyl, and aryl; wherein alkyl, alkenyl, alkynyl and aryl are each optionally substituted with one to four substituents independently selected from $R^c$;

$R^x$ is selected from the group consisting of $—OR^d$, $—NO_2$, halogen, $—S(O)_mR^d$, $—SR^d$, $—S(O)_2OR^d$, $—S(O)_mNR^dR^e$, $—NR^dR^e$, $—O(CR^fR^g)_nNR^dR^e$, $—C(O)R^d$, $—CO_2R^d$, $—CO_2(CR^fR^g)_nCONR^dR^e$, $—OC(O)R^d$, —CN, $—C(O)NR^dR^e$, $—NR^dC(O)R^e$, $—OC(O)NR^dR^e$, $—NR^dC(O)OR^e$, $—NR^dC(O)NR^dR^e$, $—CR^d(N—OR^e)$, $CF_3$, oxo, $NR^dC(O)NR^dSO_2R^i$, $NR^dS(O)_mR^e$, $—OS(O)_2OR^d$, and $—OP(O)(OR^d)_2$;

$R^y$ is selected from the group consisting of $R^x$, $C_{1-10}$ alkyl, $C_{2-10}$ alkenyl, $C_{2-10}$ alkynyl, aryl $C_{1-10}$alkyl, heteroaryl $C_{1-10}$ alkyl, cycloalkyl, heterocyclyl; wherein alkyl alkenyl, alkynyl and aryl are each optionally substituted with one to four substitutents independently selected from $R^x$;

Cy is cycloalkyl, heterocyclyl, aryl, or heteroaryl;

m is an integer from 1 to 2;

n is an integer from 1 to 10;

W is selected from the group consisting of carbon and nitrogen;

W' is selected from the group consisting of carbon, nitrogen, oxygen, sulfur, S(O) and $S(O)_2$;

X' is selected from the group consisting of $—C(O)OR^d$, $—P(O)(OR^d)(OR^e)$, $—P(O)(R^d)(OR^e)$, $—S(O)_mOR^d$, $—C(O)NR^dR^h$, and -5-tetrazolyl;

and enatiomers, diastereomers and pharmaceutically acceptable salts thereof; provided that:

(i) the compound of formula Va has a binding affinity to VLA-4 as expressed by an $IC_{50}$ of about 15 μM or less; and (ii) when $R^1$ and $R^2$, together with the carbon atom and W to which they are bound respectively, are joined to form a 2-arylpyrimidin-4-yl group and $R^{14}$ is hydrogen, then $R^{15}$ is not alkyl of from 1 to 6 carbon atoms optionally substituted with hydroxyl; and (iii) when $R^1$ and $R^2$, together with the carbon atom and W to which they are attached respectively, are joined to form a 5-arylpyrazin-2-yl group and $R^{14}$ is hydrogen, then $R^{15}$ is not 4-hydroxybenzyl.

Preferably, in the above compounds, $R^1$ and $R^7$, together with the carbon atom and W to which they are attached respectively, are joined to form substituted or unsubstituted pyrrole, pyrazole, imidazole, pyrimidine, 1,2,3-triazole, 1,2,4-triazole, tetrazole, thiophene, pyrimidine, 1,2,3-triazole, 1,2,4-triazole, tetrazole rings, 1-oxo-1,2,5-thiadiazole, 1,1-dioxo-1,2,5-thiadiazole, pyridine or 1,3,5-triazine ring and X is $—C(O)OR^d$.

In a more preferred embodiment, this invention is directed to compounds of formula Va, Vb, or Vc:

Va

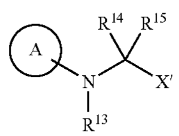

Vb

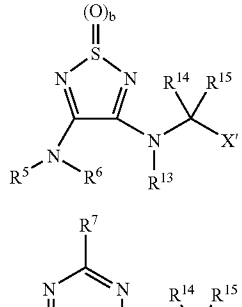

Vc

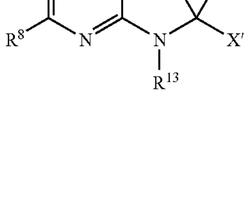

wherein:

ring A is selected from the group consisting of pyrrole, pyrazole, imidazole, pyrimidine, 1,2,3-triazole, 1,2,4-triazole, tetrazole, and thiophene wherein each of said pyrrole, pyrazole, imidazole, and thiophene ring is substituted with 1 to 3 substituent(s), and each of said pyrimidine, 1,2,3-triazole, 1,2,4-triazole, and tetrazole ring is substituted with 1 to 2 substituent(s), independently selected from the group consisting of alkyl, alkoxy, halogen, nitro, amino, substituted amino, aryl, substituted aryl, heteroaryl, substituted heteroaryl, heterocyle, substitued heterocycle, and —$SO_2R^a$ (wherein $R^a$ is alkyl, aryl, or substituted aryl);

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —$SO_2R^{10}$ where $R^{10}$ is selected from the group consisting of alkyl, substituted alkyl cycloalkyl, substituted cycloalkyl, cycloalkenyl, substituted cycloalkenyl, heterocyclic, substituted heterocyclic, aryl, substituted aryl, heteroaryl, and substituted heteroaryl;

$R^7$ is selected from the group consisting of hydrogen, halogen, hydroxy, substituted amino, heterocycle, and substituted heterocyle;

$R^8$ is selected from the group consisting of substituted amino, heterocycle, and substituted heterocycle;

b is 1 or 2; and $R^{13}$, $R^{14}$, $R^{15}$, and X' are as defined above.

In yet another of its composition aspects, this invention is directed to a compound of formula VIa and VIb:

VIa

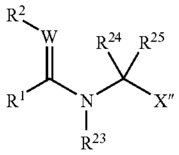

and

VIb

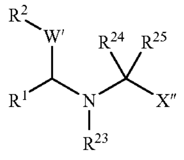

wherein, in formula VIa, $R^1$ and $R^2$, together with the carbon atom and W to which they are bound respectively, are joined to form an aryl, cycloalkenyl, heteroaryl or heterocyclic group having at least five atoms in the aryl, cycloalkenyl, heteroaryl or heterocyclic group and optionally containing or additionally containing in the case of heteroaryl and heterocyclic groups 1 to 3 heteroatoms selected from the group consisting of oxygen, nitrogen and sulfur, and wherein the heteroaryl or heterocyclic group is mono-cyclic;

in formula VIb, $R^1$ and $R^2$, together with the carbon atom and W' to which they are bound respectively, are joined to form a cycloalkyl, cycloalkenyl or heterocyclic group having at least five atoms in the cycloalkyl, cycloalkenyl or heterocyclic group and optionally containing or additionally containing in the case of the heterocyclic group 1 to 3 heteroatoms selected from the group consisting of oxygen, nitrogen and sulfur, and wherein the heterocyclic group is mono-cyclic;

and further wherein said aryl, cycloalkyl, cycloalkenyl, heteroaryl or heterocyclic group of formula VIa or VIb is optionally substituted, or any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where each R is independently hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, —$N[S(O)_2—R']_2$ and —$N[S(O)_2—NR']_2$ where each R' is independently selected from the group consisting of alkyl, substituted alkyl, aryl, substituted aryl, heteroaryl, substituted heteroaryl, heterocyclic and substituted heterocyclic;

$R^{23}$ is selected from the group consisting of hydrogen, $C_{1-10}$ alkyl optionally substituted with one to four substituents independently selected from $R^{a'}$ and Cy optionally substituted with one to four substituents independently selected from $R^{b'}$;

$R^{24}$ is selected from the group consisting of $Ar^1$—$Ar^2$—$C_{1-10}$ alkyl, $Ar^1$—$Ar^2$—$C_{2-10}$ alkenyl, $Ar^1$—$Ar^2$—$C_{2-10}$ alkynyl, wherein $Ar^1$ and $Ar^2$ are independently aryl or heteroaryl each of which is optionally substituted with one to four substituents independently selected from $R^{b'}$; alkyl, alkenyl and alkynyl are optionally substituted with one to four substituents independently selected from $R^{a'}$;

$R^{25}$ is selected from the group consisting of hydrogen, $C_{1-10}$ alkyl, $C_{2-10}$ alkenyl, $C_{2-10}$ alkynyl, aryl, aryl $C_{1-10}$alkyl, heteroaryl, and heteroaryl $C_{1-10}$ alkyl, wherein alkyl, alkenyl and alkynyl are optionally substituted with one to four substituents selected from $R^{a'}$, and aryl and heteroaryl are optionally substituted with one to four substituents independently selected from $R^{b'}$;

$R^{a'}$ is selected from the group consisting of Cy, —$OR^{d'}$, —$NO_2$, halogen —$S(O)_mR^{d'}$, —$SR^{d'}$, —$S(O)_2OR^{d'}$, $-S(O)_mNR^{d'}R^{e'}$, $-NR^{d'}R^{e'}$, $-O(CR^{f'}R^{g'})_nNR^{d'}R^{e'}$, $-C(O)R^{d'}$, $-CO_2R^{d'}$, $-CO_2(CR^{f'}R^{g'})_nCONR^{d'}R^{e'}$, $-OC(O)R^{d'}$, $-CN$, $-C(O)NR^{d'}R^{e'}$, $-NR^{d'C(O)Re'}$, $-OC(O)NR^{d'}R^{e'}$, $-NR^{d'}C(O)OR^{e'}$, $-Nr^{d'}C(O)NR^{d'}R^{e'}$, $-CR^{d'}(N-OR^{e'})$, $CF_3$, and $-OCF_3$;

wherein Cy is optionally substituted with one to four substituents independently selected from $R^{c'}$;

$R^{b'}$ is selected from the group consisting of $R^{a'}$, $C_{1-10}$ alkyl, $C_{2-10}$ alkenyl, $C_{2-10}$ alkynyl, aryl $C_{1-10}$ alkyl, heteroaryl $C_{1-10}$alkyl, wherein alkyl, alkenyl, aryl, heteroaryl are optionally substituted with a group independently selected from $R^{c'}$;

$R^{c'}$ is selected from the group consisting of halogen, amino, carboxy, $C_{1-4}$ alkyl, $C_{1-4}$ alkoxy, aryl, aryl $C_{1-4}$alkyl, hydroxy, $CF_3$, and aryloxy;

$R^{d'}$ and $R^{e'}$ are independently selected from hydrogen, $C_{1-10}$ alkyl, $C_{2-10}$ alkenyl, $C_{2-10}$ alkynyl, Cy and Cy $C_{1-10}$alkyl, wherein alkyl, alkenyl, alkynyl and Cy are optionally substituted with one to four substituents independently selected from $R^{c'}$; or $R^{d'}$ and $R^{e'}$ together with the atoms to which they are attached form a heterocyclic ring of 5 to 7 members containing 0-2 additional heteroatoms independently selected from oxygen, sulfur and nitrogen;

$R^{f'}$ and $R^{g'}$ are independently selected from hydrogen, $C_{1-10}$ alkyl, Cy and Cy-$C_{1-10}$ alkyl; or $R^{f'}$ and $R^{g'}$ together with the carbon to which they are attached form a ring of 5 to 7 members containing 0-2 heteroatoms independently selected from oxygen, sulfur and nitrogen;

$R^{h'}$ is selected from the group consisting of hydrogen, $C_{1-10}$ alkyl, $C_{2-10}$ alkenyl, $C_{1-10}$ alkynyl, cyano, aryl, aryl $C_{1-10}$ alkyl, heteroaryl, heteroaryl $C_{1-10}$ alkyl, or $-SO_2R^{i'}$;

wherein alkyl, alkenyl, and alkynyl are optionally substituted with one to four substitutents independently selected from $R^{a'}$; and aryl and heteroaryl are each optionally substituted with one to four substituents independently selected from $R^{b'}$;

$R^{i'}$ is selected from the group consisting of $C_{1-10}$ alkyl, $C_{2-10}$ alkenyl, $C_{2-10}$ alkynyl, and aryl;

wherein alkyl, alkenyl, alkynyl and aryl are each optionally substituted with one to four substituents independently selected from $R^{c'}$;

Cy is cycloalkyl, heterocyclyl, aryl, or heteroaryl;

X" is selected from the group consisting of $-C(O)OR^{d'}$, $-P(O)(OR^{d'})(OR^{e'})$, $P(O)(R^{d'})(OR^{e'})$, $S(O)_mOR^{d'}$, $-C(O)NR^{d'}R^{h'}$, and -5-tetrazolyl;

m is an integer from 1 to 2;

n is an integer from 1 to 10;

and enantiomers, diastereomers and pharmaceutically acceptable salts thereof; provided that:

(i) the compound of formula VIa or VIb has a binding affinity to VLA-4 as expressed by an $IC_{50}$ of about 15 μM or less; and (ii) in formula VIa and VIb, $R^1$ and $R^2$, together with the carbon atom and W to which they are bound respectively, do not form a substituted or unsubstituted pyridazine ring.

In the above embodiment, $R^1$ and $R^2$, together with the carbon atom and W to which they are bound respectively, are joined to form a substituted or unsubstituted monocyclic heteroaryl or heterocyclic ring wherein the heteroaryl ring contains 1 to 4 heteroatoms selected from N, O or S and the heterocyclic ring contains 1 to 3 heteroatoms selected from N, O, or S(O)n wherein n is 0 to 2, preferably $R^1$ and $R^2$, together with the carbon atom and W to which they are bound respectively, are joined to form substituted or unsubstituted pyrrole, pyrazole, imidazole, 1,2,3-triazole, 1,2,4-triazole, tetrazole, thiophene, pyridine, pyrimidine, 1,3,5-triazine, 1-oxo-1,2,5-thiadiazole or 1,1-dioxo-1,2,5-thiadiazole ring; more preferably, substituted 1,3,5-triazine, or 1,1-dioxo-1,2,5-thiadiazole ring.

Preferably, X" is $-C(O)OR^{d'}$.

In the above compounds, $R^{24}$ is preferably $-CH_2-Ar^2-Ar^1$ and $R^{25}$ is preferably hydrogen.

In a more preferred embodiment, this invention is directed to compounds of formula VIIa, VIIb, or VIIc:

VIIa

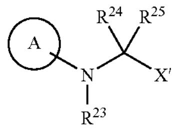

VIIb

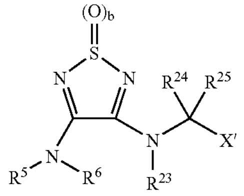

VIIc

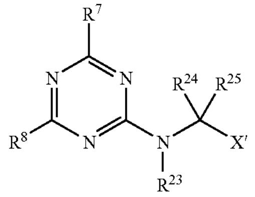

wherein:

ring A is selected from the group consisting of pyrrole, pyrazole, imidazole, pyrimidine, 1,2,3-triazole, 1,2,4-triazole, tetrazole, and thiophene wherein each of said pyrrole, pyrazole, imidazole, and thiophene ring is substituted with 1 to 3 substituent(s), and the pyrimidine, 1,2,3-triazole, 1,2,4-triazole, and tetrazole rings are substituted with 1 to 2 substituent(s), independently selected from the group consisting of alkyl, alkoxy, halogen, nitro, amino, substituted amino, aryl, substituted aryl, heteroaryl, substituted heteroaryl, heterocyle, substitued heterocycle, and $-SO_2R^a$ (wherein $R^a$ is alkyl, aryl, or substituted aryl);

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and $-SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, and substituted heteroaryl;

$R^7$ is selected from the group consisting of hydrogen, halogen, hydroxy, substituted amino, heterocycle, and substituted heterocycle;

$R^8$ is selected from the group consisting of substituted amino, heterocycle, and substituted heterocycle;

b is 1 ro 2; and $R^{23}$, $R^{24}$, $R^{25}$, and X" are as defined above.

This invention also provides pharmaceutical compositions comprising a pharmaceutically acceptable carrier and a therapeutically effective amount of the compounds defined above.

In the above compounds, when X is other than —OH or pharmaceutical salts thereof, X is a substituent which will convert (e.g., hydrolyze, metabolize, etc.) in vivo to a compound where X is —OH or a salt thereof. Accordingly, suitable X groups are any art recognized pharmaceutically acceptable groups which will hydrolyze or otherwise convert in vivo to a hydroxyl group or a salt thereof including, by way of example, esters (X is alkoxy, substituted alkoxy, cycloalkoxy, substituted cycloalkoxy, alkenoxy, substituted alkenoxy, cycloalkenoxy, substituted cycloalkenoxy, aryloxy, substituted aryloxy, heteroaryloxy, substituted heteroaryloxy, heterocyclooxy, substituted heterocyclooxy, and the like).

In the compounds of formula Ia-b, IVa-b, VIa-b above, $R^1$ and $R^2$ are preferably joined to form a substituted 1,3,5-triazine group.

Unless otherwise defined, $R^3$ and $R^{15}$ in the above compounds are preferably selected from all possible isomers arising by substitution with the following groups:

4-methylbenzyl,
4-hydroxybenzyl,
4-methoxybenzyl,
4-t-butoxybenzyl,
4-benzyloxybenzyl,
4-[ϕ-$CH(CH_3)O$-]benzyl,
4-[ϕ-CH(COOH)O-]benzyl,
4-[$BocNHCH_2C(O)NH$-]benzyl,
4-chlorobenzyl,
4-[$NH_2CH_2C(O)NH$-]benzyl,
4-carboxybenzyl,
4-[$CbzNHCH_2CH_2NH$-]benzyl,
3-hydroxy-4-(ϕ-OC(O)NH-)benzyl,
4-[$HOOCCH_2CH_2C(O)NH$-]benzyl, benzyl,
4-[2'-carboxylphenoxy-]benzyl,
4-[ϕ-C(O)NH-]benzyl,
3-carboxybenzyl,
4-iodobenzyl,
4-hydroxy-3,5-diiodobenzyl,
4-hydroxy-3-iodobenzyl,
4-[2'-carboxyphenyl-]benzyl,
—$CH_2CH_2$—,
4-nitrobenzyl,
2-carboxybenzyl,
4-[dibenzylamino]-benzyl,
4-[(1'-cyclopropylpiperidin-4'-yl)C(O)NH-]benzyl,
4-[-$NHC(O)CH_2NHBoc$]benzyl,
4-carboxybenzyl,
4-hydroxy-3-nitrobenzyl,
4-[-$NHC(O)CH(CH_3)NHBoc$]benzyl,
4-[-$NHC(O)CH(CH_2$ϕ$)NHBoc$]benzyl,
isobutyl,
methyl,
4-[$CH_3C(O)NH$-]benzyl,
—$CH_2$-(3-indolyl),
n-butyl,
t-butyl-$OC(O)CH_2$—,
t-butyl-$OC(O)CH_2CH_2$—,
$H_2NC(O)CH_2$—,
$H_2NC(O)CH_2CH_2$—,
BocNH—$(CH_2)_4$—, t-butyl-OC(O)—$(CH_2)_2$—,
$HOOCCH_2$—,
$HOOC(CH_2)_2$—;
$H_2N(CH_2)_4$—,
isopropyl,
(1-naphthyl)-$CH_2$—,
(2-naphthyl)-$CH_2$—,
(2-thiophenyl)-$CH_2$—,
(ϕ-$CH_2$—OC(O)NH—$(CH_2)_4$—.
cyclohexyl-$CH_2$—,
benzyloxy-$CH_2$—,
$HOCH_2$—,
5-(3-N-benzyl)imidazolyl-$CH_2$—,
2-pyridyl-$CH_2$—,
3-pyridyl-$CH_2$—,
4-pyridyl-$CH_2$—,
5-(3-N-methyl)imidazolyl-$CH_2$—,
N-benzylpiperid-4-yl-$CH_2$—,
N-Boc-piperidin-4-yl-$CH_2$—,
N-(phenyl-carbonyl)piperidin-4-yl-$CH_2$—,
$H_3CSCH_2CH_2$—,
1-N-benzylimidazol-4-yl-$CH_2$—,
iso-propyl-C(O)NH—$(CH_2)_4$—,
iso-butyl-C(O)NH—$(CH_2)_4$—,
phenyl-C(O)NH—$(CH_2)_4$—,
benzyl-C(O)NH—$(CH_2)_4$—,
allyl-C(O)NH—$(CH_2)_4$—,
4-(3-N-methylimidazolyl)-$CH_2$—,
4-imidazolyl,
4-[$(CH_3)_2NCH_2CH_2CH_2$—O-]benzyl,
4-[$(benzyl)_2N$-]-benzyl,
4-aminobenzyl,
allyloxy-$C(O)NH(CH_2)_4$—,
allyloxy-$C(O)NH(CH_2)_3$—,
allyloxy-$C(O)NH(CH_2)_2$—,
$NH_2C(O)CH_2$—,
ϕ-CH═,
2-pyridyl-C(O)NH—$(CH_2)_4$—,
4-methylpyrid-3-yl-C(O)NH—$(CH_2)_4$—,
3-methylthien-2-yl-C(O)NH—$(CH_2)_4$—,
2-pyrrolyl-C(O)NH—$(CH_2)_4$—,
2-furanyl-C(O)NH—$(CH_2)_4$—,
4-methylphenyl-$SO_2$—$N(CH_3)CH_2C(O)NH(CH_2)_4$—,
4-[cyclopentylacetylenyl]-benzyl,
4-[-NHC(O)—(N-Boc)-pyrrolidin-2-yl)]-benzyl-,
1-N-methylimidazol-4-yl-$CH_2$—,
1-N-methylimidazol-5-yl-$CH_2$—,
imidazol-5-yl-$CH_2$—,
6-methylpyrid-3-yl-C(O)NH—$(CH_2)_4$—,
4-[2'-carboxymethylphenyl]-benzyl,
4-[-$NHC(O)NHCH_2CH_2CH_2$-ϕ]-benzyl,
4-[-$NHC(O)NHCH_2CH_2$-ϕ]-benzyl,
—$CH_2C(O)NH(CH_2)_4$ϕ,
4-[ϕ$(CH_2)_4O$-]-benzyl,
4-[-C≡C-ϕ-4'ϕ)-]-benzyl,
4-[-C≡C—$CH_2$—O—$S(O)_2$-4'-$CH_3$-ϕ]-benzyl,
4-[-C≡C—$CH_2NHC(O)NH_2$]-benzyl,
4-[-C≡C—$CH_2$—O-4'-$COOCH_2CH_3$-ϕ]-benzyl,
4-[-C≡C—$CH(NH_2)$-cyclohexyl]-benzyl,
—$(CH_2)_4NHC(O)CH_2$-3-indolyl,
—$(CH_2)_4NHC(O)CH_2CH_2$-3-indolyl,
—$(CH_2)_4NHC(O)$-3-(5-methoxyindolyl),
—$(CH_2)_4NHC(O)$-3-(1-methylindolyl),
—$(CH_2)_4NHC(O)$-4-(-$SO_2(CH_3)$-ϕ),
—$(CH_2)_4NHC(O)$-4-$(C(O)CH_3)$-phenyl,
—$(CH_2)_4NHC(O)$-4-fluorophenyl,
—$(CH_2)_4NHC(O)CH_2O$-4-fluorophenyl,
4-[-C≡C-(2-pyridyl)]benzyl,
4-[-C≡C—$CH_2$—O-phenyl]benzyl, 4-[-C≡C—$CH_2OCH_3$]benzyl,
4-[-C≡C-(3-hydroxyphenyl)]benzyl,
4-[-C≡C—$CH_2$—O-4'-(—C(O)$OC_2H_5$)phenyl]benzyl,
4-[(—C≡C—$CH_2CH(C(O)OCH_3)_2$]benzyl,
4-[-C≡C—$CH_2$NH-(4,5-dihydro-4-oxo-5-phenyl-oxazol-2-yl),
3-aminobenzyl,
4-[-C≡C—$CH_2CH(NHC(O)CH_3)C(O)OH$]-benzyl,
—$CH_2C(O)NHCH(CH_3)$ϕ,
—$CH_2C(O)NHCH_2$-(4-dimethylamino)-ϕ,
—$CH_2C(O)NHCH_2$-4-nitrophenyl,
—$CH_2CH_2C(O)N(CH_3)CH_2$-ϕ,
—$CH_2CH_2C(O)NHCH_2CH_2$-(N-methyl)-2-pyrrolyl,
—$CH_2CH_2C(O)NHCH_2CH_2CH_2CH_3$,
—$CH_2CH_2C(O)NHCH_2CH_2$-3-indolyl,
—$CH_2C(O)N(CH_3)CH_2$phenyl,
—$CH_2C(O)NH(CH_2)_2$—(N-methyl)-2-pyrrolyl,
—$CH_2C(O)NHCH_2CH_2CH_2CH_3$,
—$CH_2C(O)NHCH_2CH_2$-3-indolyl,
—$(CH_2)_2C(O)NHCH(CH_3)$ϕ,
—$(CH_2)_2C(O)NHCH_2$-4-dimethylaminophenyl,
—$(CH_2)_2C(O)NHCH_2$-4-nitrophenyl,
—$CH_2C(O)NH$-4-[-NHC(O)$CH_3$-phenyl],
—$CH_2C(O)NH$-4-pyridyl,
—$CH_2C(O)NH$-4-[dimethylaminophenyl],
—$CH_2C(O)NH$-3-methoxyphenyl,
—$CH_2CH_2C(O)NH$-4-chlorophenyl,
—$CH_2CH_2C(O)NH$-2-pyridyl,
—$CH_2CH_2C(O)NH$-4-methoxyphenyl,
—$CH_2CH_2C(O)NH$-3-pyridyl,
4-[$(CH_3)_2NCH_2CH_2O$-]benzyl,
—$(CH_2)_3NHC(NH)NH$—$SO_2$-4-methylphenyl,
4-[$(CH_3)_2NCH_2CH_2O$-]benzyl,
—$(CH_2)_4NHC(O)NHCH_2CH_3$,
—$(CH_2)_4NHC(O)NH$-phenyl,
—$(CH_2)_4NHC(O)NH$-4-methoxyphenyl,
4-[4'-pyridyl-C(O)NH-]benzyl,
4-[3'-pyridyl-C(O)NH-]benzyl,
4-[-NHC(O)NH-3'-methylphenyl]benzyl,
4-[-NHC(O)$CH_2$NHC(O)NH-3'-methylphenyl]benzyl,
4-[-NHC(O)-(2',3'-dihydroindol-2-yl)]benzyl,
4-[-NHC(O)-(2',3'-dihydro-N-Boc-indol-2-yl)]benzyl,
p-[-$OCH_2CH_2$-1'-(4'-pyrimidinyl)-piperazinyl]benzyl,
4-[-$OCH_2CH_2$-(1'-piperidinyl]benzyl,
4-[-$OCH_2CH_2$-(1'-pyrrolidinyl)]benzyl,
4-[-$OCH_2CH_2CH_2$-(1'-piperidinyl)]benzyl-,
—$CH_2$-3-(1,2,4-triazolyl),
4-[-$OCH_2CH_2CH_2$-4-(3'-chlorophenyl)-piperazin-1-yl]benzyl,
4-[-$OCH_2CH_2N$(ϕ)$CH_2CH_3$]benzyl,
4-[-$OCH_2$-3'-(N-Boc)-piperidinyl]benzyl,
4-[di-n-pentylamino]benzyl,
4-[n-pentylamino]benzyl,
4-[di-iso-propylamino-$CH_2CH_2O$-]benzyl,
4-[-$OCH_2CH_2$-(N-morpholinyl)]benzyl,
4-[-O-(3'-(N-Boc)-piperidinyl]benzyl,
4-[-$OCH_2CH(NHBoc)CH_2$cyclohexyl]benzyl,
p-[$OCH_2CH_2$-(N-piperidinyl]benzyl,
4-[-$OCH_2CH_2CH_2$-(4-m-chlorophenyl)-piperazin-1-yl]benzyl,
4-[-$OCH_2CH_2$-(N-homopiperidinyl)benzyl,
4-[-NHC(O)-3'-(N-Boc)-piperidinyl]benzyl,
4-[-$OCH_2CH_2N(benzyl)_2$]benzyl,
—$CH_2$-2-thiazolyl,
3-hydroxybenzyl,
4-[-$OCH_2CH_2CH_2N(CH_3)_2$]benzyl,
4-[-NHC(S)$NHCH_2CH_2$-(N-morpholino)]benzyl,
4-[-$OCH_2CH_2N(C_2H_5)_2$]benzyl,
4-[-$OCH_2CH_2CH_2N(C_2H_5)_2$]benzyl,
4-[$CH_3(CH_2)_4NH$-]benzyl,
4-[N-n-butyl,N-n-pentylamino-]benzyl,
4-[-NHC(O)-4'-piperidinyl]benzyl,
4-[-NHC(O)CH(NHBoc)$(CH_2)_4$NHCbz]benzyl,
4-[-NHC(O)-(1',2',3',4'-tetrahydro-N-Boc-isoquinolin-1'-yl] benzyl,
p-[-$OCH_2CH_2CH_2$-1'-(4'-methyl)-piperazinyl]benzyl,
—$(CH_2)_4$NH-Boc,
3-[-$OCH_2CH_2CH_2N(CH_3)$]benzyl,
4-[-$OCH_2CH_2CH_2N(CH_3)_2$]benzyl,
3-[-$OCH_2CH_2$-(1'-pyrrolidinyl)]benzyl,
4-[-$OCH_2CH_2CH_2N(CH_3)$benzyl]benzyl,
4-[-NHC(S)$NHCH_2CH_2CH_2$-(N-morpholino)]benzyl,
4-[-$OCH_2CH_2$-(N-morpholino)]benzyl,
4-[-$NHCH_2$-(4'-chlorophenyl)]benzyl,
4-[-NHC(O)NH-(4'-cyanophenyl)]benzyl, 4-[-$OCH_2COOH$]benzyl,
4-[-$OCH_2COO$-t-butyl]benzyl,
4-[-NHC(O)-5-fluoroindol-2-yl]benzyl,
4-[-NHC(S)NH$(CH_2)_2$-1-piperidinyl]benzyl,
4-[-N($SO_2CH_3$)$(CH_2)_3$—$N(CH_3)_2$]benzyl,
4-[-NHC(O)$CH_2CH(C(O)OCH_2$ϕ)-NHCbz]benzyl,
4-[-NHS$(O)_2CF_3$]benzyl,
3-[-O-(N-methylpiperidin-4'-yl]benzyl,
4-[-C(=NH)$NH_2$]benzyl,
4-[-$NHSO_2$—$CH_2Cl$]benzyl,
4-[-NHC(O)-(1',2',3',4'-tetrahydroisoquinolin-2'-yl]benzyl,
4-[-NHC(S)NH$(CH_2)_3$—N-morpholino]benzyl,
4-[-NHC(O)CH($CH_2CH_2CH_2CH_2NH_2$)NHBoc]benzyl,
4-[-C(O)$NH_2$]benzyl,
4-[-NHC(O)NH-3'-methoxyphenyl]benzyl,
4-[-$OCH_2CH_2$-indol-3'-yl]benzyl,
4-[-$OCH_2C(O)NH$-benzyl]benzyl,
4-[-$OCH_2C(O)O$-benzyl]benzyl,
4-[-$OCH_2C(O)OH$]benzyl,
4-[-$OCH_2$-2'-(4',5'-dihydro)imidazolyl]benzyl,
—$CH_2C(O)NHCH_2$-(4-dimethylamino)phenyl,
—$CH_2C(O)NHCH_2$-(4-dimethylamino)phenyl,
4-[NHC(O)-L-2'-pyrrolidinyl-N—$SO_2$-4'-methylphenyl] benzyl,
4-[-NHC(O)$NHCH_2CH_2CH_3$]benzyl,
4-aminobenzyl]benzyl,
4-[-$OCH_2CH_2$-1-(4-hydroxy-4-(3-methoxypyrrol-2-yl)-piperazinyl]benzyl,
4-[-O-(N-methylpiperidin-4'-yl)]benzyl,
3-methoxybenzyl,
4-[-NHC(O)-piperidin-3'-yl]benzyl, 4-[-NHC(O)-pyridin-2'-yl]benzyl,
4-[-$NHCH_2$-(4'-chlorophenyl)]benzyl,
4-[-NHC(O)—(N-(4'-CH3-ϕ-$SO_2$)-L-pyrrolidin-2'-yl)]benzyl,
4-[-NHC(O)$NHCH_2CH_2$-ϕ]benzyl,
4-[-$OCH_2C(O)NH_2$]benzyl,
4-[-$OCH_2C(O)NH$-t-butyl]benzyl,
4-[-$OCH_2CH_2$-1-(4-hydroxy-4-phenyl)-piperidinyl]benzyl,
4-[-$NHSO_2$—CH=$CH_2$]benzyl,
4-[-$NHSO_2$—$CH_2CH_2Cl$]benzyl,
—$CH_2C(O)NHCH_2CH_2N(CH_3)_2$,
4-[(1'-Cbz-piperidin-4'-yl)C(O)NH-]benzyl,
4-[(1'-Boc-piperidin-4'-yl)C(O)NH-]benzyl,
4-[(2'-bromophenyl)C(O)NH-]benzyl,
4-[-NHC(O)-pyridin-4'-yl]benzyl,
4-[(4'-$(CH_3)_2NC(O)O$—)phenyl)-C(O)NH-]benzyl,
4-[-NHC(O)-1'-methylpiperidin-4'-yl-]benzyl,
4-(dimethylamino)benzyl, 4-[-NHC(O)-(1'-N-Boc)-piperidin-2'-yl]benzyl,
3-[-NHC(O)-pyridin-4'-yl]benzyl, 4-[(tert-butyl-O(O)CCH$_2$—O-benzyl)-NH-]benzyl,
[BocNHCH$_2$C(O)NH-]butyl,
4-benzylbenzyl,
2-hydroxyethyl,
4-[(Et)$_2$NCH$_2$CH$_2$CH$_2$NHC(S)NH-]benzyl,
4-[(1'-Boc-4'-hydroxypyrrolidin-2'-yl)C(O)NH-]benzyl,
4-[4CH$_2$CH$_2$CH$_2$NHC(S)NH-]benzyl,
4-[(perhydroindolin-2'-yl)C(O)NH-]benzyl,
2-[4-hydroxy-4-(3-methoxythien-2-yl)piperidin-1-yl]ethyl,
4-[(1'-Boc-perhydroindolin-2'-yl)-C(O)NH-]benzyl,
4-[N-3-methylbutyl-N-trifluoromethanesulfonyl)amino]benzyl,
4-[N-vinylsulfonyl)amino]benzyl,
4-[2-(2-azabicyclo[3.2.2]octan-2-yl)ethyl-O-]benzyl,
4-[4'-hydroxypyrrolidin-2'-yl)C(O)NH-]benzyl,
4-(ϕNHC(S)NH)benzyl,
4-(EtNHC(S)NH)benzyl,
4-(ϕCH$_2$NHC(S)NH)benzyl,
3-[(1'-Boc-piperidin-2'-yl)C(O)NH-]benzyl,
3-[piperidin-2'-yl-C(O)NH-]benzyl,
4-[(3'-Boc-thiazolidin-4'-yl)C(O)NH-]benzyl,
4-(pyridin-3'-yl-NHC(S)NH)benzyl,
4-(CH$_3$—NHC(S)NH)benzyl,
4-(H$_2$NCH$_2$CH$_2$CH$_2$C(O)NH)benzyl,
4-(BocHNCH$_2$CH$_2$CH$_2$C(O)NH)benzyl,
4-(pyridin-4'-yl-CH$_2$NH)benzyl,
4-[(N,N-di(4-N,N-dimethylamino)benzyl)amino]benzyl,
4-[(1-Cbz-piperidin-4-yl)C(O)NH-]butyl,
4-[4CH$_2$OCH$_2$(BocHN)CHC(O)NH]benzyl,
4-[(piperidin-4'-yl)C(O)NH-]benzyl, 4-[(pyrrolidin-2'-yl)C(O)NH-]benzyl,
4-(pyridin-3'-yl-C(O)NH)butyl,
4-(pyridin-4'-yl-C(O)NH)butyl,
4-(pyridin-3'-yl-C(O)NH)benzyl,
4-[CH$_3$NHCH$_2$CH$_2$CH$_2$C(O)NH-]benzyl,
4-[CH$_3$N(Boc)CH$_2$CH$_2$CH$_2$C(O)NH-]benzyl,
4-(aminomethyl)benzyl,
4-[ϕCH$_2$OCH$_2$(H$_2$N)CHC(O)NH]benzyl,
4-[(1',4'-di(Boc)piperazin-2'-yl)-C(O)NH-]benzyl,
4-[(piperazin-2'-yl)-C(O)NH-]benzyl,
4-[(N-toluenesulfonylpyrrolidin-2'-yl)C(O)NH-]butyl,
4-[-NHC(O)-4'-piperidinyl]butyl,
4-[-NHC(O)-1'-N-Boc-piperidin-2'-yl]benzyl,
4-[-NHC(O)-piperidin-2'-yl]benzyl,
4-[(1'-N-Boc-2',3'-dihydroindolin-2'-yl)-C(O)NH]benzyl,
4-(pyridin-3'-yl-CH$_2$NH)benzyl,
4-[(piperidin-1'-yl)C(O)CH$_2$—O-]benzyl,
4-[(CH$_3$)$_2$CH)$_2$NC(O)CH$_2$—O-]benzyl,
4-[HO(O)C(Cbz-NH)CHCH$_2$CH$_2$—C(O)NH-]benzyl,
4-[ϕCH$_2$O(O)C(Cbz-NH)CHCH$_2$CH$_2$—C(O)NH-]benzyl,
4-[-NHC(O)-2'-methoxyphenyl]benzyl,
4-[(pyrazin-2'-yl)C(O)NH-]benzyl,
4-[HO(O)C(NH$_2$)CHCH$_2$CH$_2$—C(O)NH-]benzyl,
4-(2'-formyl-1',2',3',4'-tetrahydroisoquinolin-3'-yl-CH$_2$NH—)benzyl,
N-Cbz-NHCH$_2$—,
4-[(4'-methylpiperazin-1'-yl)C(O)O-]benzyl,
4-[CH$_3$(N-Boc)NCH$_2$C(O)NH-]benzyl,
4-[-NHC(O)-(1',2', 3',4'-tetrahydro-N-Boc-isoquinolin-3'-yl]-benzyl,
4-[CH$_3$NHCH$_2$C(O)NH-]benzyl, (CH$_3$)$_2$NC(O)CH$_2$—,
4-(N-methylacetamido)benzyl;
4-(1',2',3',4'-tetrahydroisoquinolin-3'-yl-CH$_2$NH-)benzyl,
4-[(CH$_3$)$_2$NHCH$_2$C(O)NH-]benzyl, (1-toluenesulfonylimidizol-4-yl)methyl,
4-[(1'-Boc-piperidin-4'-yl)C(O)NH-]benzyl,
4-trifluoromethylbenzyl,
4-[(2'-bromophenyl)C(O)NH-]benzyl,
4-[(CH$_3$)$_2$NC(O)NH-]benzyl,
4-[CH$_3$OC(O)NH-]benzyl,
4-[(CH$_3$)$_2$NC(O)O-]benzyl,
4-[(CH$_3$)$_2$NC(O)N(CH$_3$)-]benzyl,
4-[CH$_3$OC(O)N(CH$_3$)-]benzyl,
4-(N-methyltrifluoroacetamido)benzyl,
4-[(1'-methoxycarbonylpiperidin-4'-yl)C(O)NH-]benzyl,
4-[(4'-phenylpiperidin-4'-yl)C(O)NH-]benzyl,
4-[(4'-phenyl-1'-Boc-piperidin-4'-yl)-C(O)NH-]benzyl,
4-[(piperidin-4'-yl)C(O)O-]benzyl, 4-[(1'-methylpiperidin-4'-yl)-O-]benzyl,
4-[(1'-methylpiperidin-4'-yl)C(O)O-]benzyl,
4-[(4'-methylpiperazin-1'-yl)C(O)NH-]benzyl,
3-[(CH$_3$)$_2$NC(O)O-]benzyl,
4-[(4'-phenyl-1'-Boc-piperidin-4'-yl)-C(O)O-]benzyl,
4-(N-toluenesulfonylamino)benzyl,
4-[(CH$_3$)$_3$CC(O)NH-]benzyl,
4-[(morpholin-4'-yl)C(O)NH-]benzyl,
4-[(CH$_3$CH$_2$)$_2$NC(O)NH-]benzyl,
4-[-C(O)NH-(4'-piperidinyl)]benzyl,
4-[(2'-trifluoromethylphenyl)C(O)NH-]benzyl,
4-[(2'-methylphenyl)C(O)NH-]benzyl,
4-[(CH$_3$)$_2$NS(O)$_2$O-]benzyl,
4-[(pyrrolidin-2'-yl)C(O)NH-]benzyl,
4-[-NHC(O)-piperidin-1'-yl]benzyl,
4-[(thiomorpholin-4'-yl)C(O)NH-]benzyl,
4-[(thiomorpholin-4'-yl sulfone)-C(O)NH-]benzyl,
4-[(morpholin-4'-yl)C(O)O-]benzyl,
3-nitro-4-(CH$_3$OC(O)CH$_2$O-)benzyl,
(2-benzoxazolinon-6-yl)methyl-,
(2H-1,4-benzoxazin-3 (4H)-one-7-yl)methyl-, 4-[(CH$_3$)$_2$NS(O)$_2$NH-]benzyl,
4-[(CH$_3$)$_2$NS(O)$_2$N(CH$_3$)-]benzyl,
4-[(thiomorpholin-4'-yl)C(O)O-]benzyl,
4-[(thiomorpholin-4'-yl sulfone)-C(O)O-]benzyl,
4-[(piperidin-1'-yl)C(O)O-]benzyl,
4-[(pyrrolidin-1'-yl)C(O)O-]benzyl,
4-[(4'-methylpiperazin-1'-yl)C(O)O-]benzyl,
4-[(2'-methylpyrrolidin-1'-yl)-,
(pyridin-4-yl)methyl-,
4-[(piperazin-4'-yl)-C(O)O-]benzyl,
4-[(1'-Boc-piperazin-4'-yl)-C(O)O-]benzyl,
4-[(4'-acetylpiperazin-1'-yl)C(O)O-]benzyl,
p-[(4'-methanesulfonylpiperazin-1'-yl)-benzyl,
3-nitro-4-[(morpholin-4'-yl)-C(O)O-]benzyl,
4-{[(CH$_3$)$_2$NC(S)]$_2$N-}benzyl,
N-Boc-2-aminoethyl-,
4-[(1,1-dioxothiomorpholin-4-yl)-C(O)O-]benzyl,
4-[(CH$_3$)$_2$NS(O)$_2$-]benzyl,
4-(imidazolid-2'-one-1'-yl)benzyl,
4-[(piperidin-1'-yl)C(O)O-]benzyl,
1-N-benzyl-imidazol-4-yl-CH$_2$—,
3,4-dioxyethylenebenzyl (i.e., 3,4-ethylenedioxybenzyl),
3,4-dioxymethylenebenzyl (i.e., 3,4-methylenedioxybenzyl), 4-[-$N(SO_2)(CH_3)CH_2CH_2CH_2N(CH_3)_2$]benzyl, 4-(3'-formylimidazolid-2'-one-1'-yl)benzyl, 4-[$NHC(O)CH(CH_2CH_2CH_2CH_2NH_2)NHBoc$]benzyl,

[2'-[4"-hydroxy-4"-(3'"-methoxythien-2'"-yl)piperidin-2"-yl]ethoxy]benzyl, and p-[$(CH_3)_2NCH_2CH_2N(CH_3)C(O)O$-]benzyl.

Preferably, in the compounds of formula I-VII above, $R^{3'}$ is preferably hydrogen.

Preferably, in the compounds of formula I-VII above, $R^4$ is preferably hydrogen and X is preferably hydroxyl or alkoxy.

In the compounds of formula IVa-b and V, preferred $R^{13}$, $R^{14}$ and $R^{15}$ groups correspond to the $R^3$, $R^4$ and $R^5$ groups, respectively, disclosed in International Patent Application Publication No. WO 98/53814 which application is incorporated herein by reference in its entirety.

In the compounds of formula VIa-b, preferred $R^{23}$, $R^{24}$ and $R^{25}$ groups correspond to the $R^5$, $R^6$ and $R^7$ groups, respectively, found in International Patent Application Publication No. WO 98/53817 which application is incorporated herein by reference in its entirety. In a preferred embodiment, in compounds of formula IVa-b and VII, $R^{24}$ is —$CH_2$—$Ar^2$—$Ar^1$ and $R^{25}$ is hydrogen.

This invention also provides methods for binding VLA-4 in a biological sample which method comprises contacting the biological sample with a compound of formula I-VII above under conditions wherein said compound binds to VLA-4.

Certain of the compounds of formula I-VII above are also useful in reducing VLA-4 mediated inflammation in vivo.

This invention also provides pharmaceutical compositions comprising a pharmaceutically acceptable carrier and a therapeutically effective amount of one or more of the compounds of formula I-VII above. Preferably, $R^3$ and $R^3$ are derived from L-amino acids or other similarly configured starting materials. Alternatively, racemic mixtures can be used.

The pharmaceutical compositions may be used to treat VLA-4 mediated disease conditions. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Other disease conditions include, but are not limited to, inflammatory conditions such as erythema nodosum, allergic conjunctivitis, optic neuritis, uveitis, allergic rhinitis, Ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

Accordingly, this invention also provides methods for the treatment of an inflammatory disease in a patient mediated by VLA-4 which methods comprise administering to the patient the pharmaceutical compositions described above.

Representative compounds of this invention are set forth in Tables I-V below:

I.

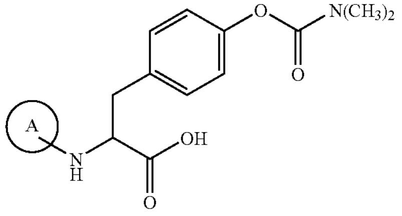

| Cpd # | A |
|---|---|
| 1 | 3-nitrothiophen-2-yl |
| 2 | 1-phenyltetrazol-5-yl |
| 3 | 1,3-dimethyl-4-nitropyrazol-5-yl |
| 4 | 1-ethylpyrazol-5-yl |
| 5 | 4-phenylsulfonylthiophen-3-yl |
| 6 | 1,4-diphenyl-1,2,3-triazol-5-yl |
| 7 | 1-phenylimidazol-2-yl |
| 8 | 5-[5-phenylcarbonylmethylthio-4-(3-trifluoromethylphenyl)-1,2,4-triazol-3-yl]pyridin-2-yl |
| 9 | 6-bromopyridin-2-yl |
| 10 | 6-naphth-1-ylpyridin-2-yl |
| 11 | 3-[N-methyl-N-(4-methylphenylsulfonyl)amino]pyridin-2-yl |
| 12 | 3-[N-methyl-N-(4-methylphenylsulfonyl)amino]pyridin-4-yl |
| 13 | 5-trifluoromethylpyridin-2-yl |
| 14 | 4-methyl-3-nitropyridin-2-yl |
| 15 | 3,5-di-nitropyridin-2-yl |
| 15 | 3-[N-methyl-N-(4-methylphenylsulfonyl)amino]-4-methylpyridin-4-yl |

II.

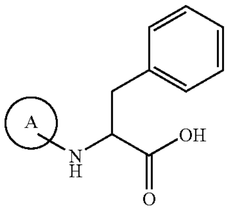

| Cpd # | A |
|---|---|
| 1 | 3-[N-methyl-N-(4-methylphenylsulfonyl)amino]pyridin-2-yl |
| 2 | 3-[N-methyl-N-(4-methylphenylsulfonyl)amino]pyridin-4-yl |

III.

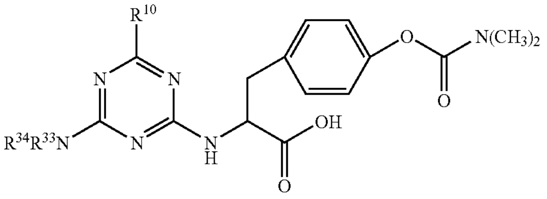

| Cpd # | $R^{10}$ | $R^{33}$ | $R^{34}$ |
|---|---|---|---|
| 1 | 2-methylpropylamino | H | 5-methylisoxazol-3-yl |
| 2 | phenylamino | H | 5-methylisoxazo-3-yl |
| 3 | benzylamino | H | 5-methylisoxazol-3-yl |
| 4 | [2-(4-methylphenyl)ethyl]amino | H | 2-(1-methylpyrrolidin-2-yl)ethyl |
| 5 | [2-(4-methoxyphenyl)ethyl]amino | H | 2-(1-methylpyrrolidin-2-yl)ethyl |
| 6 | (1-phenylethyl)amino | H | 2-(1-methylpyrrolidin-2-yl)ethyl |
| 7 | (4-chlorobenzyl)amino | H | 2-(1-methylpyrrolidin-2-yl)ethyl |
| 8 | cyclohexylamino | H | 5-methylisoxazol-3-yl |
| 9 | 2-methylpropylamino | methyl | 2-(pyridin-2-yl)ethyl |
| 10 | 2-methylpropylamino | 2-methoxyethyl | 2-methoxyethyl |
| 11 | 2-methylpropylamino | methyl | 2-(pyridin-2-yl)ethyl |
| 12 | 2-methylpropylamino | methyl | 2-(phenyl)ethyl |
| 13 | benzylamino | methyl | 2-(3,4-dimethoxyphenyl)ethyl |
| 14 | cyclohexylamino | H | 2-(4-methoxyphenyl)ethyl |
| 15 | 5-methylisoxazol-3-ylamino | H | 2-methoxyethyl |
| 16 | furan-2-ylmethylamino | H | 2-methoxyethyl |
| 17 | 1-(phenyl)ethylamino | H | 2-methoxyethyl |
| 18 | 4-chlorobenzylamino | H | 2-methoxyethyl |
| 19 | cyclohexylmethylamino | H | 5-methylisoxazol-3-yl |
| 20 | 2-methylpropylamino | H | 2-(4-methoxyphenyl)ethyl |
| 21 | 2-methylpropylamino | H | furan-2-ylmethyl |
| 22 | 2-methylpropylamino | H | 1-(phenyl)ethyl |
| 23 | 2-methylpropylamino | H | 4-aminosulfonylbenzyl |
| 24 | phenylamino | H | furan-2-ylmethyl |
| 25 | phenylamino | H | 4-aminosulfonylbenzyl |
| 26 | 4-chlorobenzylamino | H | 2-piperidin-1-ylethyl |
| 27 | 2-(4-methoxyphenyl)ethylamino | H | 2-(4-methylphenyl)ethyl |
| 28 | 4-chlorobenzylamino | H | 2-(4-methylphenyl)ethyl |
| 29 | 4-aminosulfonylbenzylamino | H | 2-(4-methylphenyl)ethyl |
| 30 | benzylamino | H | 2-(4-methoxyphenyl)ethyl |
| 31 | benzylamino | H | 1-phenylethyl |
| 22 | cyclopentylamino | H | 1-phenylethyl |
| 33 | cyclohexylamino | H | 4-aminosulfonylbenzyl |
| 34 | 3,4-methylenedioxybenzylamino | H | 2-(4-methoxyphenyl)ethyl |
| 35 | 3,4-methylenedioxybenzylamino | H | furan-2-ylmethyl |
| 36 | 3,4-methylenedioxybenzylamino | H | 4-chlorobenzyl |
| 37 | 3,4-methylenedioxybenzylamino | H | 4-aminosulfonylbenzyl |
| 38 | cyclohexylmethylamino | H | furan-2-ylmethyl |
| 39 | chloro | 2-propyl | benzyl |
| 40 | chloro | methyl | 2-phenylethyl |
| 41 | chloro | methyl | 2-(3,4-dimethoxyphenyl)ethyl |
| 42 | chloro | ethyl | pyridin-4-ylmethyl |
| 43 | chloro | benzyl | 1 -phenylethyl |
| 44 | chloro | allyl | cyclopentyl |
| 45 | chloro | ethyl | 1-(4-methoxybenzyl)ethyl |
| 46 | chloro | n-propyl | 4-nitrobenzyl |
| 47 | chloro | methyl | 2-pyridin-2-ylethyl |
| 48 | chloro | benzyl | benzyl |
| 49 | chloro | benzyl | 2-cyanoethyl |
| 50 | chloro | benzyl | 2-N,N-dimethylaminoethyl |
| 51 | 2-methylpropylamino | ethyl | 3,4-dichlorobenzyl |
| 52 | benzylamino | ethyl | pyridin-4-ylmethyl |
| 53 | benzylamino | methyl | pyridin-3-ylmethyl |
| 54 | 2-methoxyethylamino | pyridin-3-ylmethyl | pyridin-3-ylmethyl |
| 55 | 2-methoxyethylamino | benzyl | benzyl |
| 56 | 2-methoxyethylamino | benzyl | 2-cyanoethyl |
| 57 | cyclopentylamino | phenyl | pyridin-2-yl |
| 58 | N,N-bis-(2-methoxyethyl)amino | methyl | 4-methylphenylsulfonyl |
| 59 | N-2-propyl-N-benzylamino | methyl | 4-methylphenylsulfonyl |
| 60 | N-methyl-N-[2-(phenyl)ethyl]-amino | methyl | 4-methylphenylsulfonyl |
| 61 | N-methyl-N-[2-(3,4-dimethoxy-phenyl)-ethyl]amino | methyl | 4-methylphenylsulfonyl |
| 62 | N-ethyl-N-pyridin-4-ylmethylamino | methyl | 4-methylphenylsulfonyl |
| 63 | N-methyl-N-pyridin-3-ylmethylamino | methyl | 4-methylphenylsulfonyl |
| 64 | N-ethyl-N-[1(4-methoxybenzyl)ethyl]amino | methyl | 4-methylphenylsulfonyl |
| 65 | N-propyl-N-(4-nitrobenzyl)amino | methyl | 4-methylphenylsulfonyl |

-continued

III.

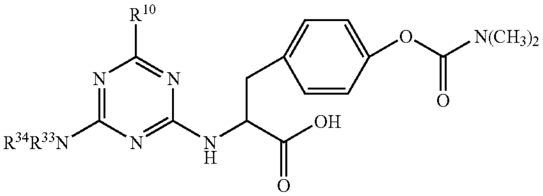

| Cpd # | $R^{10}$ | $R^{33}$ | $R^{34}$ |
|---|---|---|---|
| 66 | N-(4-aminosulfonylbenzyl)amino | methyl | 4-methylphenylsulfonyl |
| 67 | N-methyl-N-(3-dimethylaminopropyl)amino | methyl | 4-methylphenylsulfonyl |
| 68 | N,N-bis-benzylamino | methyl | 4-methylphenylsulfonyl |
| 69 | N-methyl-N-[2-(pyridin-2-yl)ethyl]amino | methyl | 4-methylphenylsulfonyl |
| 70 | N-methyl-N-benzylamino | methyl | 4-methylphenylsulfonyl |
| 71 | N-2-methylpropylamino | methyl | 4-methylphenylsulfonyl |
| 72 | N-benzylamino | methyl | 4-methylphenylsulfonyl |
| 73 | N-[2-(1-methylpyrrolidin-2-yl)ethyl]amino | methyl | 4-methylphenylsulfonyl |
| 74 | N-furan-2-ylmethylamino | methyl | 4-methylphenylsulfonyl |
| 75 | N-(1-phenylethyl)amino | methyl | 4-methylphenylsulfonyl |
| 76 | N,N-bis-propylamino | methyl | 4-methylphenylsulfonyl |
| 77 | N-methyl-N-[2-(pyridin-2-yl)ethyl]amino | methyl | 4-methylphenylsulfonyl |
| 78 | N-benzyl-N-(2-dimethylaminoethyl)amino | methyl | 4-methylphenylsulfonyl |
| 79 | chloro | cyclohexyl | cyclohexyl |
| 80 | chloro | methyl | pyridin-3-ylmethyl |
| 81 | 5-methylisoxazol-3-ylamino | ethyl | 1-(4-methoxybenzyl)ethyl |
| 82 | chloro | methyl | 4-methylphenylsulfonyl |
| 83 | hydrogen | 2-methylpropyl | 4-methylphenylsulfonyl |
| 84 | hydrogen | methyl | 4-methylphenylsulfonyl |
| 85 | hydrogen | hydrogen | 2-phenyl-1-carboxamidoethyl |
| 86 | hydrogen | hydrogen | (2-phenyl-1,1-dimethyl)ethyl |
| 87 | hydrogen | hydrogen | 2-phenylethyl |
| 88 | hydrogen | hydrogen | 2-(2-methoxyphenyl)ethyl |
| 89 | hydrogen | hydrogen | 2-(3,4-dimethoxyphenyl)ethyl |
| 90 | hydrogen | hydrogen | [2-(4-fluorophenyl)-1,1-dimethyl]ethyl |
| 91 | hydrogen | hydrogen | [1-phenyl-2-(4-methylphenyl)]ethyl |
| 92 | hydrogen | methyl | 2-(3,4-dimethoxyphenyl)ethyl |
| 93 | hydrogen | methyl | 2-(pheny)ethyl |
| 94 | hydrogen | ethyl | 1-(4-methoxybenzyl)ethyl |
| 95 | chloro | benzyl | 1-phenylethyl |
| 96 | chloro | hydrogen | pyridin-4-ylmethyl |
| 97 | chloro | hydrogen | pyridin-3-ylmethyl |
| 98 | chloro | hydrogen | 2-pyridin-2-ylethyl |
| 99 | chloro | hydrogen | 2-(4-benzylpiperizin-1-yl)ethyl |
| 100 | chloro | pyridin-2-ylmethyl | 2-ethylhexyl |
| 101 | chloro | hydrogen | pyridin-2-ylmethyl |
| 102 | hydrogen | hydrogen | 3,3-diphenylpropyl |
| 103 | hydrogen | hydrogen | pyridin-2-ylmethyl |
| 104 | hydrogen | hydrogen | pyridin-3-ylmethyl |
| 105 | hydrogen | hydrogen | 2-pyridin-2-ylethyl |
| 106 | hydrogen | hydrogen | 2-(4-ethoxy-3-methoxyphenyl)ethyl |
| 107 | hydrogen | hydrogen | 2-phenylpropyl |
| 108 | hydrogen | hydrogen | (S)-1-phenylethyl |
| 109 | hydrogen | pyridin-2-ylmethyl | 2-ethylhexyl |
| 110 | chloro | hydrogen | 4-(piperazin-3,5-dione-1-ylsulfonyl)-phenyl |
| 111 | chloro | methyl | methyl |
| 112 | chloro | hydrogen | 2-pyrrolidin-1-ylethyl |
| 113 | hydroxy | hydrogen | 2-phenylpropyl |
| 114 | hydroxy | hydrogen | 2-phenyl-1-carboxamidoethyl |
| 115 | hydroxy | hydrogen | 2-phenyl-1,1-dimethylethyl |
| 116 | hydroxy | hydrogen | 2-phenylethyl |
| 117 | hydroxy | hydrogen | 2-(2-methoxyphenyl)ethyl |
| 118 | hydroxy | hydrogen | 2-(3,4-dimethoxyphenyl)ethyl |
| 119 | hydroxy | hydrogen | 2-(4-flurophenyl)-1,1-dimethylethyl |
| 120 | hydroxy | hydrogen | 1-phenyl-2-(methylphenyl)ethyl |
| 121 | hydroxy | hydrogen | 4-(piperazin-3,5-dione-1-ylsulfonyl)-phenyl |
| 122 | hydroxy | methyl | methyl |
| 123 | hydroxy | hydrogen | 3-imidazol-1-ylpropyl |
| 124 | hydroxy | hydrogen | 2-morpholin-4-ylethyl |
| 125 | hydroxy | hydrogen | 2-piperidin-1-ylethyl |
| 126 | hydroxy | hydrogen | 2-pyrrolidin-1-ylethyl |
| 127 | hydroxy | hydrogen | 1-ethoxycarbonylpiperidifl-4-yl |
| 128 | hydroxy | hydrogen | 2-phenoxyethyl |
| 129 | chloro | hydrogen | 3-pyrrolidin-1-ylpropyl |
| 130 | hydroxy | hydrogen | 3-pyrrolidin-1-ylpropyl |
| 131 | hydroxy | benzyl | 1-phenylethyl |

-continued

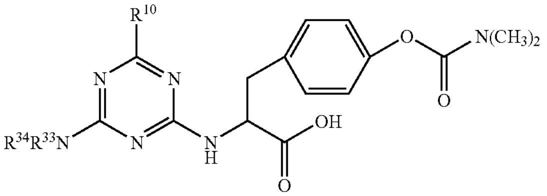

III.

| Cpd # | $R^{10}$ | $R^{33}$ | $R^{34}$ |
|---|---|---|---|
| 132 | hydroxy | hydrogen | 5-chloro-1,3-dimethylpyrazol-4-yl-sulfonyl |
| 133 | hydroxy | hydrogen | benzylsulfonyl |
| 134 | hydroxy | hydrogen | 2-carboxy-1-phenylethyl |
| 135 | hydroxy | hydrogen | 1-phenylethyl |
| 136 | hydroxy | hydrogen | 1-phenyl-1-ethoxycarbonylmethyl |
| 137 | chloro | benzyl | 1-carboxy-2-phenylethyl |
| 138 | hydroxy | benzyl | 1-carboxy-2-phenylethyl |
| 139 | hydrogen | hydrogen | 4-(piperazin-3,5-dione-1-ylsulfonyl)-phenyl |
| 140 | hydrogen | hydrogen | pyridin-4-ylmethyl |
| 141 | hydrogen | hydrogen | 2-(4-benzylpiperazin-1yl)ethyl |
| 142 | hydrogen | methyl | methyl |
| 143 | hydrogen | hydrogen | 2-morpholin-4-ylethyl |
| 144 | hydrogen | hydrogen | 2-phenoxyethyl |
| 145 | hydrogen | hydrogen | 1-phenyl-2-carboxyethyl |
| 146 | hydrogen | hydrogen | 1-phenyl-1-ethoxycarbonylmethyl |
| 147 | hydrogen | hydrogen | 1-carboxy-3-phenylpropyl |
| 148 | hydrogen | hydrogen | 1-phenylethyl |
| 149 | chloro | methyl | 2-pyridin-2-ylethyl |
| 150 | 2-methoxyethylamino | methyl | 2-pyridin-2-ylethyl |
| 151 | hydrogen | benzyl | 1-phenylethyl |
| 152 | hydrogen | hydrogen | 2-carboxy-1-phenylethyl |

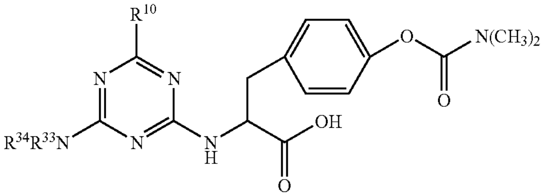

III.

| Cpd # | $R^{10}$ | $NR^{33}R^{34}$ |
|---|---|---|
| 1 | 2-methylpropylamino | 4-phenylpiperazin-1-yl |
| 2 | 2-methylpropylamino | 4-acetylpiperazin-1-yl |
| 3 | 6-nitrobenzothiazol-2-ylamino | piperidin-1-yl |
| 4 | furan-2-ylmethylamino | piperidin-1-yl |
| 5 | 1-phenylethylamino | piperidin-1-yl |
| 6 | 4-chlorobenzylamino | piperidin-1-yl |
| 7 | piperidin-1-yl | 4-acetylpiperazin-1-yl |
| 8 | 4-aminosulfonylbenzylamino | piperidin-1-yl |
| 9 | benzylamino | 4-acetylpiperazin-1-yl |
| 10 | chloro | 4-benzylpiperidin-1-yl |
| 11 | chloro | 2-methyl-5-ethylpiperidin-1-yl |
| 12 | chloro | 4-cyclohexylpiperazin-1-yl |
| 13 | chloro | 4-(3,4-methylenedioxybenzyl)piperazin-1-yl |
| 14 | chloro | 4-(diphenylmethyl)piperazin-1-yl |
| 15 | chloro | 4-acetylpiperazin-1-yl |
| 16 | chloro | 3-methylpiperidin-1-yl |
| 17 | chloro | 2,6-dimethylmorpholin-1-4-yl |
| 18 | cyclopentylamino | 2,6-dimethylmorpholin-4-yl |
| 19 | N-methyl-N-(4-methylphenysulfonyl)amino | 4-cyclohexylpiperazin-1-yl |
| 20 | N-methyl-N-(4-methylpheylsulfonyl)amino | 3-methylpiperidin-1-yl |
| 21 | 2-(4-aminosulfonylphenyl)ethylamino | piperidin-1-yl |
| 22 | chloro | 2-(4-benzylpiperazin-1-yl)ethyl |
| 23 | chloro | 4-(2-propylamidomethyl)piperazin-1-yl |
| 24 | chloro | 4-(1-phenylethyl)piperazin-1-yl |
| 25 | chloro | 4-(2-phenylethyl)piperazin-1-yl |
| 26 | chloro | 4-(furan-2-ylcarbonyl)piperazin-1-yl |
| 27 | chloro | 4-(1-phenyl-1-propen-3-yl)piperazin-1-yl |

-continued

III.

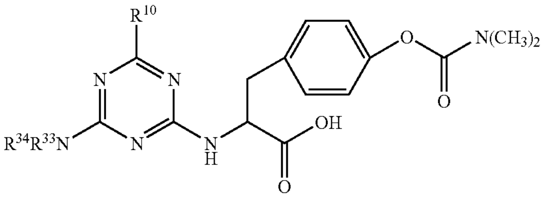

| Cpd # | $R^{10}$ | $NR^{33}R^{34}$ |
|---|---|---|
| 28 | hydrogen | 4-(2-propylamidomethyl)piperazin-1-yl |
| 29 | hydrogen | 4-(2-phenylethyl)piperazin-1-yl |
| 30 | hydrogen | 4-(furan-2-ylcarbonyl)piperazin-1-yl |
| 31 | hydrogen | 4-(2-morpholin-4-ylethyl)piperazin-1-yl |
| 32 | chloro | 1,2,3,4-tetrahydroisoquinolin-2-yl |
| 33 | hydroxy | 1,2,3,4-tetrahydroisoquinolin-2-yl |
| 34 | chloro | 4-ethoxycarbonylmethylpiperazin-1-yl |
| 35 | hydroxy | 4-ethoxycarbonylmethylpiperazin-1-yl |
| 36 | chloro | piperazin-1-yl |
| 37 | chloro | 4-(2-methoxyethyl)piperazin-1-yl |
| 38 | chloro | 2-ethoxycarbonylpiperidin-1-yl |
| 39 | chloro | 2-ethoxycarbonylmethyl-3-oxopiperazin-1-yl |
| 40 | chloro | 3-ethoxycarbonylpiperidin-1-yl |
| 41 | hydroxy | 3-(S)-ethoxycarbonyl-1,2,3,4-tetrahydro-isoquinolin-2-yl |
| 42 | chloro | 3-carboxy-1,2,3,4-tetrahydroisoquinolin-2-yl |
| 43 | hydroxy | 3-carboxy-1,2,3,4-tetrahydroisoquinolin-2-yl |
| 44 | hydrogen | 1,2,3,4-tetrahydroisoquinolin-2-yl |
| 45 | hydrogen | 4-ethoxycarbonylmethylpiperazin-1-yl |
| 46 | hydrogen | piperazin-1-yl |
| 47 | hydrogen | 2-ethoxycarbonylpiperidin-1-yl |
| 48 | hydrogen | 2-ethoxycarbonylmethyl-3-oxopiperazin-1-yl |
| 49 | cyclopentylamino | 4-acetylpiperazin-1-yl |
| 50 | hydrogen | 3-carboxy-1,2,3,4-tetrahydroisoquinolin-2-yl |

IV.

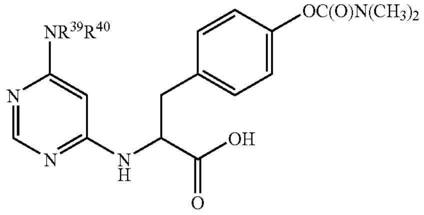

| Cpd # | $R^{39}$ | $R^{40}$ | $NR^{39}R^{40}$ |
|---|---|---|---|
| 1 | 3-methylpropyl | 4-methylphenylsulfonyl | |
| 2 | methyl | 4-methylphenylsulfonyl | |
| 3 | hydrogen | 2-phenylethyl | |
| 4 | methyl | 2-pyridin-2-ylethyl | |
| 5 | methyl | benzyl | |
| 6 | | | 4-acetylpiperazin-1-yl |
| 7 | methyl | pyridin-3-ylmethyl | |
| 8 | methyl | 2-(3,4-dimethoxyphenyl)ethyl | |
| 9 | methyl | 2-phenylethyl | |
| 10 | hydrogen | 2-phenylpropyl | |
| 11 | | | 4-(2-propylaminocarbonylmethyl)piperazin-1-yl |
| 12 | | | 4-(2-morpholin-4-ylethyl)piperazin-1-yl |
| 13 | hydrogen | 2-phenylethyl | |

Accordingly, this invention is directed to each of the following compounds:

N-(3-nitrothiophen-2-yl)-L-4-(N,N-dimethylcarbamyloxy)-phenylalanine;

N-[1-phenyltetrazol-5-yl]-L-4-(N,N-dimethylcarbamyloxy)-phenylalanine;

N-[1,3-dimethyl-4-nitropyrazol-5-yl]-L-4-(N,N-dimethylcarbamyl-oxy)phenylalanine;

N-[1-ethylpyrazol-5-yl]-L-4-(N,N-dimethylcarbamyloxy)-phenylalanine;

N-(4-phenylsulfonylthiophen-3-yl)-L-4-(N,N-dimethylcarbamyloxy)-phenylalanine;

N-(1,4-diphenyl-1,2,3-triazol-5-yl)-L-4-(N,N-dimethylcarbamyloxy)-phenylalanine;

N-(1-phenylimidazol-2-yl)-L-4-(N,N-dimethylcarbamyloxy)-phenylalanine;

N-(6-bromopyridin-2-yl)-L-4-(N,N-dimethylcarbamyloxy)-phenylalanine;

N-[6-(naphth-1-yl)pyridin-2-yl]-L-4-(N,N-dimethylcarbamyloxy)-phenylalanine;

N-{3-[N-methyl-N-(4-methylphenylsulfonyl)amino]pyridin-2-yl}-L-4-(N,N-dimethylcarbamyloxy)phenylalanine;

N-{3-[N-methyl-N-(4-methylphenylsulfonyl)amino]pyridin-4-yl}-L-4-(N,N-dimethylcarbamyloxy)phenylalanine;

N-(5-trifluoropyridin-2-yl)-L-4-(N,N-dimethylcarbamyloxy)-phenylalanine;

N-{5-[[5-phenylcarbonylmethylthio-4-(3-trifluoromethylphenyl)]-1,2,4-triazol-3-yl]pyridin-2-yl}-L-4-(N,N-dimethylcarbamyloxy)-phenylalanine;

N-(4-methyl-3-nitropyridin-2-yl)-L-4-(N,N-dimethylcarbamyloxy)-phenylalanine;

N-(3,5-dinitropyridin-2-yl)-L-4-(N,N-dimethylcarbamyloxy)-phenylalanine;

N-{3-[N-methyl-N-(4-methylphenylsulfonyl)amino]pyridin-4-yl}-L-phenylalanine;

N-[4-(3-methylisoxazol-5-ylamino)-6-(2-methylpropylamino)-1,3,5-triazin-2-yl]-L-4-(N,N-dimethylcarbamyloxy)phenylalanine;

N-[4-(phenylamino)-6-(3-methylisoxazol-5-ylamino)-1,3,5-triazin-2-yl]-L-4-(N,N-dimethylcarbamyloxy)phenylalanine;

N-[4-(benzylamino)-6-(3-methylisoxazol-5-ylamino)-1,3,5-triazin-2-yl]-L-4-(N,N-dimethylcarbamyloxy)phenylalanine;

N-{4-[2-(1-methylpyrrolidin-2-yl)ethylamino]-6-[2-(4-methylphenyl)ethylamino)]-1,3,5-triazin-2-yl}-L-4-(N,N-dimethyl-carbamyloxy)phenylalanine;

N-{4-[2-(4-methoxlphenyl)ethylamino)]-6-[2-(1-methylpyrrolidin-2-yl)ethylamino]-1,3,5-triazin-2-yl}-L-4-(N,N-dimethylcarbamyloxy)phenylalanine;

N-{4-[(4-chlorobenzyl)amino)]-6-[2-(1-methylpyrrolidin-2-yl)ethylamino]-1,3,5-triazin-2-yl}-L-4-(N,N-dimethylcarbamyloxy)phenylalanine;

N-{6-[2-(1-methylpyrrolidin-2-yl)ethylamino]-4-[1-(phenyl)ethylamino)]-1,3,5-triazin-2-yl}-L-4-(N,N-dimethylcarbamyloxy)-phenylalanine;

N-[4-(cyclohexylamino)-6-(3-methylisoxazol-5-ylamino)-1,3,5-triazin-2-yl]-L-4-(N,N-dimethylcarbamyloxy)phenylalanine;

N-{4-(2-methylpropylamino)-6-[N-methyl-N-(2-pyridin-2-ylethyl)-amino]-1,3,5-triazin-2-yl}-L-4-(N,N-dimethylcarbamyloxy)-phenylalanine;

N-{4-(2-methylpropylamino)-6-[N,N-bis(2-methoxyethyl)-amino]-1,3,5-triazin-2-yl}-L-4-(N,N-dimethylcarbamyloxy)-phenylalanine;

N-{4-(2-methylpropylamino)-6-[N-methyl-N-(2-phenylethyl)amino]-1,3,5-triazin-2-yl}L-4-(N,N-dimethylcarbamyloxy)phenylalanine;

N-{4-(benzylamino)-6-[N-methyl-N-(2-(3,4-dimethoxyphenyl)-ethyl)amino]-1,3,5-triazin-2-yl}-L-4-(N,N-dimethylcarbamyloxy)-phenylalanine;

N-{4-(cyclohexylamino)-6-[2-(4-methoxy]phenyl)ethylamino]-1,3,5-triazin-2-yl}-L-4-(N,N-dimethylcarbamyloxy)phenylalanine;

N-[4-(2-methoxyethylamino)-6-(3-methylisoxazol-5-ylamino)-1,3,5-triazin-2-yl]-L-4-(N,N-dimethylcarbamyloxy)phenylalanine;

N-[6-(furan-2-ylmethylamino)-4-(2-methoxyethylamino)-1,3,5-triazin-2-yl]-L-4-(N,N-dimethylcarbamyloxy)phenylalanine;

N-[4-(methoxyethylamino)-6-(1-phenylethylamino)-1,3,5-triazin-2-yl]-L-4-(N,N-dimethylcarbamyloxy)phenylalanine;

N-[6-(chlorobenzylamino)-4-(2-methoxyethylamino)-1,3,5-triazin-2-yl]-L-4-(N,N-dimethylcarbamyloxy)phenylalanine;

N-[4-(cyclohexylmethylamino)-6-(3-methylisoxazol-5-ylamino)-1,3,5-triazin-2-yl]-L-4-(N,N-dimethylcarbamyloxy)phenyalanine;

N-{4-(2-methylpropylamino)-6-[2-(4-methoxyphenyl)ethylamino]-1,3,5-triazin-2-yl}-L-4-(N,N-dimethylcarbamyloxy)phenylalanine;

N-[6-(furan-2-ylmethylamino)-4-(2-methylpropylamino)-1,3,5-triazin-2-yl]-L-4-(N,N-dimethylcarbamyloxy)phenylalanine;

N-{4-(2-methylpropylamino)-6-(1-phenylethylamino)-1,3,5-triazin-2-yl}-L-4-(N,N-dimethylcarbamyloxy)phenylalanine;

N-{6-(4-aminosulfonylbenzylamino)-4-(2-methylpropylamino)-1,3,5-triazin-2-yl}-L-4-(N,N-dimethylcarbamyloxy)phenylalanine;

N-{4-(benzylamino)-6-(furan-2-ylmethylamino)-1,3,5-triazin-2-yl}-L-4-(N,N-dimethylcarbamyloxy)phenylalanine;

N-{6-(4-aminosulfonylbenzylamino)-4-(benzylamino)-1,3,5-triazin-2-yl}-L-4-(N,N-dimethylcarbamyloxy)phenylalanine;

N-{4-(4-chlorobenzylamino)-6-[2-(pyrrolidin-1-yl)ethylamino]-1,3,5-triazin-2-yl}-L-4-(N,N-dimethylcarbamyloxy)phenylalanine;

N-{4-[2-(4-methoxyphenyl)ethylamino)]-6-[2-(4-methylphenyl)ethylamino]-1,3,5-triazin-2-yl}-L-4-(N,N-dimethylcarbamyloxy)-phenylalanine;

N-{4-(4-chlorobenzylamino)-6-[2-(4-methylphenyl)ethylamino]-1,3,5-triazin-2-yl}-L-4-(N,N-dimethylcarbamyloxy)phenylalanine;

N-{6-(4-aminosulfonylbenzylamino)-4-[2-(4-methylphenyl)ethylamino]-1,3,5-triazin-2-yl}-L-4-(N,N-dimethylcarbamyloxy)-phenylalanine;

N-{4-(benzylamino)-6-[2-(4-methoxybenzyl)amino)-1,3,5-triazin-2-yl}-L-4-(N,N-dimethylcarbamyloxy)phenylalanine;

N-{4-(benzylamino)-6-(1-phenylethylamino)-1,3,5-triazin-2-yl}-L-4-(N,N-dimethylcarbamyloxy)phenylalanine;

N-{4-(cyclohexylamino)-6-(1-phenylethylamino)-1,3,5-triazin-2-yl}-L-4-(N,N-dimethylcarbamyloxy)phenylalanine;

N-{6-(4-aminosulfonylbenzylamino)-4-(1-cyclhexylethylamino)-1,3,5-triazin-2-yl}-L-4-(N,N-dimethylcarbamyloxy)phenylalanine;

N-{4-[2-(4-methoxyphenyl)ethylamino]-6-(3,4-methylene-dioxy-benzylamino)-1,3,5-triazin-2-yl}-L-4-(N,N-dimethylcarbamyloxy)-phenylalanine;

N-{6-(furan-2-ylmethylamino)-4-(3,4-methylenedioxybenzylamino)-1,3,5-triazin-2-yl}-L-4-(N,N-dimethylcarbamyloxy)phenylalanine;

N-{6-(4-chlorobenzylamino)-4-(3,4-methylenedioxybenzylamino)-1,3,5-triazin-2-yl}-L-4-(N,N-dimethylcarbamyloxy)phenylalanine;

N-{6-(4-aminosulfonylbenzylamino)-4-(3,4-methylene-dioxybenzyl-amino)-1,3,5-triazin-2-yl}-L-4-(N,N-dimethylcarbamyloxy)-phenylalanine;

N-{4-(cyclohexylmethylamino)-6-(furan-2-ylmethylamino)-1,3,5-triazin-2-yl}-L-4-(N,N-dimethylcarbamyloxy)phenylalanine;

N-{4-chloro-6-[N-benzyl-N-(2-propyl)amino]-1,3,5-triazin-2-yl}-L-4-(N,N-dimethylcarbamyloxy)phenylalanine;

N-{4-chloro-6-[N-(methyl)-N-(2-phenylethyl)amino]-1,3,5-triazin-2-yl}-L-4-(N,N-dimethylcarbamyloxy)phenylalanine;

N-{4-chloro-6-[N-(methyl)-N-(2-(3,4-dimethoxyphenyl)ethyl)amino]-1,3,5-triazin-2-yl}-L-4-(N,N-dimethylcarbamyloxy)phenylalanine;

N-{4-chloro-6-[N-(ethyl)-N-(pyridin-4-ylmethyl)amino]-1,3,5-triazin-2-yl}-L-4-(N,N-dimethylcarbamyloxy)phenylalanine;

N-{4-chloro-6-[N-(benzyl)-N-(1-phenylethyl)amino]-1,3,5-triazin-2-yl}-L-4-(N,N-dimethylcarbamyloxy)phenylalanine;

N-{4-chloro-6-[N-(allyl)-N-(cyclopentyl)amino]-1,3,5-triazin-2-yl}-L-4-(N,N-dimethylcarbamyloxy)phenylalanine;

N-{4-chloro-6-[N-(ethyl)-N-(2-(4-methoxyphenyl)-1-methylethyl)-amino]-1,3,5-triazin-2-yl}-L-4-(N,N-dimethylcarbamyloxy)-phenylalanine;

N-{4-chloro-6-[N-(n-propyl)-N-(4-nitrobenzyl)amino]-1,3,5-triazin-2-yl}-L-4-(N,N-dimethylcarbamyloxy)-phenylalanine;

N-{4-chloro-6-[N-(methyl)-N-(2-pyridin-2-ylethyl)amino]-1,3',5-triazin-2-yl}-L-4-(N,N-dimethylcarbamyloxy)phenylalanine;

N-{4-chloro-6-[N,N-bis-(benzyl)amino]-1,3,5-triazin-2-yl}-L-4-(N,N-dimethylcarbamyloxy)phenylalanine;

N-{4-chloro-6-[N-(2-cyanoethyl)-N-(benzyl)amino]-1,3,5-triazin-2-yl}-L-4-(N,N-dimethylcarbamyloxy)phenylalanine;

N-{4-chloro-6-[N-(benzyl)-N-(2-dimethylaminoethyl)amino]-1,3,5-triazin-2-yl}-L-4-(N,N-dimethylcarbamyloxy)phenylalanine;

N-{6-[N-(ethyl)-N-(3,4-dichlorobenzyl)amino]-4-(2-methylpropylamino)-1,3,5-triazin-2-yl}-L-4-(N,N-dimethylcarbamyloxy)-phenylalanine;

N-{4-(benzylamino)-6-[N-(ethyl)-N-(pyridin-4-ylmethyl)amino]-1,3,5-triazin-2-yl}-L-4-(N,N-dimethylcarbamyloxy)phenylalanine;

N-{4-(benzylamino)-6-[N-(methyl)-N-(pyridin-3-ylmethyl)amino]-1,3,5-triazin-2-yl}-L-4-(N,N-dimethylcarbamyloxy)phenylalanine;

N-{4-(2-methoxyethylamino)-6-[N-(methyl)-N-(pyridin-2-ylmethyl)-amino]-1,3,5-triazin-2-yl}-L-4-(N,N-dimethylcarbamyloxy)-phenylalanine;

N-{4-(2-methoxyethylamino)-6-[N,N-bis-(pyridin-3-ylmethyl)-amino]-1,3,5-triazin-2-yl}-L-4-(N,N-dimethylcarbamyloxy)-phenylalanine;

N-{4-(2-methoxyethylamino)-6-[N,N-bis-(benzyl)amino]-1,3,5-triazin-2-yl}-L-4-(N,N-dimethylcarbamyloxy)phenylalanine;

N-{4-(cyclohexylamino)-6-[N-(phenyl)-N-(pyridin-2-yl)amino]-1,3,5-triazin-2-yl}-L-4-(N,N-dimethylcarbamyloxy)phenylalanine;

N-{6-[N,N-bis-(2-methoxyethyl)amino]-4-[N-(methyl)-N-(4-methylphenylsulfonyl)amino]-1,3,5-triazin-2-yl}-L-4-(N,N-dimethylcarbamyloxy)phenylalanine;

N-{4-[N-(benzyl)-N-(2-propyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N-(methyl)-N-(2-phenylethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N-(methyl)-N-(2-(3,4-dimethoxyphenyl)ethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N-(ethyl)-N-(pyridin-4-ylmethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N-(methyl)-N-(pyridin-3-ylmethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N-(ethyl)-N-(2-(4-methoxyphenyl)-1-methylethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-(4-aminosulfonylbenzylamino)-6-[N-(methyl)-N-(4-methyl-phenylsulfonyl)amino]-1,3,5-triazin-2-yl}-L-4-(N,N-dimethylcarbamyloxy)phenylalanine;

N-{4-[N-(methyl)-N-(3-dimethylaminopropyl)amino]-6-[N-(methyl-N-(4-methylphenylsulfonyl)amino]-1,3,5-triazin-2-yl}-L-4-(N,N-dimethylcarbamyloxy)phenylalanine;

N-{4-[N,N-bis-(benzyl)amino]-6-[N-(methyl)-N-(4-methylphenylsulfonyl)amino]-1,3,5-triazin-2-yl}-L-4-(N,N-dimethylcarbamyloxy)-phenylalanine;

N-{4-[N-(methyl)-N-(2-pyridin-2-ylethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N-(methyl)-N-(benzyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-(2-methylpropylamino]-6-[N-(methyl)-N-(4-methylphenylsulfonyl)amino]-1,3,5-triazin-2-yl}-L-4-(N,N-dimethylcarbamyloxy)-phenylalanine;

N-{4-(benzylamino)-6-[N-(methyl)-N-(4-methylphenylsulfonyl)-amino]-1,3,5-triazin-2-yl}-L-4-(N,N-dimethylcarbamyloxy)-phenylalanine;

N-{4-[2-(1-methylpyrrolidin-1yl)ethylamino]-6-[N-(methyl)-N-(4-methylphenylsulfonyl)amino]-1,3,5-triazin-2-yl}-L-4-(N,N-dimethylcarbamyloxy)phenylalanine;

N-{4-(furan-2-ylmethylamino)-6-[N-(methyl)-N-(4-methylphenylsulfonyl)amino]-1,3,5-triazin-2-yl}-L-4-(N,N-dimethylcarbamyloxy)-phenylalanine;

N-{4-[N,N-bis-(n-propyl)amino]-6-[N-(methyl)-N-(4-methylphenylsulfonyl)amino]-1,3,5-triazin-2-yl}-L-4-(N,N-dimethylcarbamyloxy)-phenylalanine;

N-{4-[N-(methyl)-N-(2-pyridin-2-ylethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N-(benzyl)-N-(2-dimethylaminoethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-(5-methylisoxazol-3-ylamino)-6-[N-(ethyl)-N-(2-(4-methoxyphenyl)-1-methylethyl)amino]-1,3,5-triazin-2-yl}-L-4-(N,N-dimethylcarbamyloxy)phenylalanine;

N-{4-chloro-6-[N-(methyl)-N-(pyridin-3-ylmethyl)amino]-1,3,5-triazin-2-yl}-L-4-(N,N-dimethylcarbamyloxy)phenylalanine;

N-{4-chloro-6-[N,N-bis-cyclohexylamino]-1,3,5-triazin-2-yl}-L-4-(N,N-dimethylcarbamyloxy)phenylalanine;

N-{4-chloro-6-[N-(methyl)-N-(4-methylphenylsulfonyl)amino]-1,3,5-triazin-2-yl}-L-4-(N,N-dimethylcarbamyloxy)phenylalanine;

N-{4-[N-(2-methylpropyl)-N-(4-methylphenylsulfonyl)amino]-1,3,5-triazin-2-yl}-L-4-(N,N-dimethylcarbamyloxy)phenylalanine;

N-{4-[N-(methyl)-N-(4-methylphenylsulfonyl)amino]-1,3,5-triazin-2-yl}-L-4-(N,N-dimethylcarbamyloxy)phenylalanine;

N-{4-[N-(2-phenyl-1-carboxamidoethyl)amino]-1,3,5-triazin-2-yl}-L-4-(N,N-dimethylcarbamyloxy)phenylalanine;

N-{4-(N-[2-phenyl-1,1-dimethylethyl)amino]-1,3,5-triazin-2-yl}-L-4-(N,N-dimethylcarbamyloxy)phenylalanine;

N-{4-[N-(2-phenylethyl)amino]-1,3,5-triazin-2-yl}-L-4-(N,N-dimethylcarbamyloxy)phenylalanine;

N-{4-[N-(2-(2-methoxyphenyl)ethyl)amino]-1,3,5-triazin-2-yl}-L-4-(N,N-dimethylcarbamyloxy)phenylalanine;

N-{4-[N-(2-(3,4-dimethoxyphenyl)ethyl)amino]-1,3,5-triazin-2-yl}-L-4-(N,N-dimethylcarbamyloxy)phenylalanine;

N-{4-[N-(2-(4-fluorophenyl)-1,1-dimethylethyl)amino]-1,3,5-triazin-2-yl}-L-4-(N,N-dimethylcarbamyloxy)phenylalanine;

N-{4-[N-(1-phenyl-2-(4-methylphenyl)ethyl)amino]-1,3,5-triazin-2-yl}-L-4-(N,N-dimethylcarbamyloxy)phenylalanine;

N-{4-[N-(methyl)-N-(2-(3,4-dimethoxyphenyl)ethyl)amino]-1,3,5-triazin-2-yl}-L-4-(N,N-dimethylcarbamyloxy)phenylalanine;

N-{4-[N-(methyl)-N-(2-phenylethyl)amino]-1,3,5-triazin-2-yl}-L-4-(N,N-dimethylcarbamyloxy)phenylalanine;

N-{4-[N-(ethyl)-N-(2-(4-methoxyphenyl)-1-methylethyl)amino]-1,3,5-triazin-2-yl}-L-4-(N,N-dimethylcarbamyloxy)phenylalanine;

N-{4-chloro-6-[N-(benzyl)-N-(1-phenylethyl)amino]-1,3,5-triazin-2-yl}-L-4-(N,N-dimethylcarbamyloxy)phenylalanine;

N-{4-[N-(benzyl)-N-(1-phenylethyl)amino]-1,3,5-triazin-2-yl}-L-4-(N,N-dimethylcarbamyloxy)phenylalanine;

N-{4-chloro-6-(N-pyridin-4-ylmethylamino]-1,3,5-triazin-2-yl}-L-4-(N,N-dimethylcarbamyloxy)phenylalanine;

N-{4-chloro-6-(N-pyridin-3-ylmethylamino]-1,3,5-triazin-2-yl}-L-4-(N,N-dimethylcarbamyloxy)phenylalanine;

N-{4-chloro-6-[N-2-(pyridin-2-yl)ethylamino]-1,3,5-triazin-2-yl}-L-4-(N,N-dimethylcarbamyloxy)phenylalanine;

N-{4-chloro-6-[N-(2-ethylhexyl)-N-(pyridin-2-ylmethyl)amino]1,3,5-triazin-2-yl}-L-4-(N,N-dimethylcarbamyloxy)phenylalanine;

N-{4-chloro-6-(N-pyridin-2-ylmethylamino)-1,3,5-triazin-2-yl}-L-4-(N,N-dimethylcarbamyloxy)phenylalanine;

N-{4-[N-(3,3-diphenylpropyl)amino]-1,3,5-triazin-2-yl}-L-4-(N,N-dimethylcarbamyloxy)phenylalanine;

N-{4-(N-pyridin-2-ylmethylamino)-1,3,5-triazin-2-yl}-L-4-(N,N-dimethylcarbamyloxy)phenylalanine;

N-{4-(N-pyridin-3-ylmethylamino)-1,3,5-triazin-2-yl}-L-4-(N,N-dimethylcarbamyloxy)phenylalanine;

N-{4-[N-2-(pyridin-2-yl)ethylamino]-1,3,5-triazin-2-yl}-L-4-(N,N-dimethylcarbamyloxy)phenylalanine;

N-{4-[N-2-(4-ethoxy-3-methoxyphenyl)ethylamino]-1,3,5-triazin-2-yl}-L-4-(N,N-dimethylcarbamyloxy)phenylalanine;

N-{4-[N-2-phenylpropylamino]-1,3,5-triazin-2-yl}-L-4-(N,N-dimethylcarbamyloxy)phenylalanine;

N-{4-[N-1 (S)-phenylethylamino]-1,3,5-triazin-2-yl}-L-4-(N,N-dimethylcarbamyloxy)phenylalanine;

N-{4-[N-(2-ethylhexyl)-N-(pyridin-2-ylmethyl)amino]-1,3,5-triazin-2-yl}-L-4-(N,N-dimethylcarbamyloxy)phenylalanine;

N-{4-chloro-6-[N-(4-(3,5-dioxopiperazin-1-ylsulfonyl)phenyl)amino]-1,3,5-triazin-2-yl}-L-4-(N,N-dimethylcarbamyloxy)phenylalanine;

N-{4-chloro-6-[N,N-dimethylamino]-1,3,5-triazin-2-yl}-L-4-(N,N-dimethylcarbamyloxy)phenylalanine;

N-{4-chloro-6-[N-(2-pyrrolidin-1-ylethyl)amino]-1,3,5-triazin-2-yl}-L-4-(N,N-dimethylcarbamyloxy)phenylalanine;

N-{4-hydroxy-6-[N-(2-phenylpropyl)amino]-1,3,5-triazin-2-yl}-L-4-(N,N-dimethylcarbamyloxy)phenylalanine;

N-{4-hydroxy-6-[N-(2-phenyl-1-carboxamidoethyl)amino]-1,3,5-triazin-2-yl}-L-4-(N,N-dimethylcarbamyloxy)phenylalanine;

N-{4-hydroxy-6-[N-(2-phenyl-1,1-dimethylethyl)amino]-1,3,5-triazin-2-yl}-L-4-(N,N-dimethylcarbamyloxy)phenylalanine;

N-{4-hydroxy-6-[N-(2-phenylethyl)amino]-1,3,5-triazin-2-yl}-L-4-(N,N-dimethylcarbamyloxy)phenylalanine;

N-{4-hydroxy-6-[N-(2-(2-methoxyphenyl)ethyl)amino]1,3,5-triazin-2-yl}-L-4-(N,N-dimethylcarbamyloxy)phenylalanine;

N-{4-hydroxy-6-[N-(2-(3,4-dimethoxyphenyl)ethyl)amino]-1,3,5-triazin-2-yl}-L-4-(N,N-dimethylcarbamyloxy)phenylalanine;

N-{4-hydroxy-6-[N-(2-(4-fluorophenyl)-1,1-dimethylethyl)amino]-1,3,5-triazin-2-yl}-L-4-(N,N-dimethylcarbamyloxy)phenylalanine;

N-{4-hydroxy-6-[N-(1-phenyl-2-(4-methylphenyl)ethyl)amino]-1,3,5-triazin-2-yl}-L-4-(N,N-dimethylcarbamyloxy)phenylalanine;

N-{4-hydroxy-6-[N-(4-(3,5-dioxopiperazin-1-ylsulfonyl)phenyl)-amino]-1,3,5-triazin-2-yl}-L-4-(N,N-dimethylcarbamyloxy)-phenylalanine;

N-{4-hydroxy-6-(N,N-dimethylamino)-1,3,5-triazin-2-yl}-L-4-(N,N-dimethylcarbamyloxy)phenylalanine;

N-{4-hydroxy-6-[N-3-(imidazol-2-yl)propylamino]-1,3,5-triazin-2-yl}-L-4-(N,N-dimethylcarbamyloxy)phenylalanine;

N-{4-hydroxy-6-[N-2-(morpholin-4-yl)ethylamino]-1,3,5-triazin-2-yl}-L-4-(N,N-dimethylcarbamyloxy)phenylalanine;

N-{4-hydroxy-6-[N-2-(piperidin-1-yl)ethylamino]-1,3,5-triazin-2-yl}-L-4-(N,N-dimethylcarbamyloxy)phenylalanine;

N-{4-hydroxy-6-[N-2-(pyrrolidin-1-yl)ethylamino]-1,3,5-triazin-2-yl}-L-4-(N,N-dimethylcarbamyloxy)phenylalanine;

N-{4-hydroxy-6-[N-(1-ethoxycarbonylpiperidin-4-yl)amino]-1,3,5-triazin-2-yl}-L-4-(N,N-dimethylcarbamyloxy)phenylalanine;

N-{4-hydroxy-6-[N-2-(phenoxy)ethylamino]-1,3,5-triazin-2-yl}-L-4-(N,N-dimethylcarbamyloxy)phenylalanine;

N-{4-hydroxy-6-[N-3-(pyrrolidin-1-yl)propylamino]-1,3,5-triazin-2-yl}-L-4-(N,N-dimethylcarbamyloxy)phenylalanine;

N-{4-chloro-6-[N-3-(pyrrolidin-1-yl)propylamino]-1,3,5-triazin-2-yl}-L-4-(N,N-dimethylcarbamyloxy)phenylalanine;

N-{4-hydroxy-6-[N-(benzyl)-N-(1-(S)-phenylethyl)amino]-1,3,5-triazin-2-yl}-L-4-(N,N-dimethylcarbamyloxy)phenylalanine;

N-{4-hydroxy-6-[N-(5-chloro-1,3-dimethylpyrazol-4-yl)amino]-1,3,5-triazin-2-yl}-L-4-(N,N-dimethylcarbamyloxy)phenylalanine;

N-{4-hydroxy-6-[N-(benzylsulfonyl)amino]-1,3,5-triazin-2-yl}-L-4-(N,N-dimethylcarbamyloxy)phenylalanine;

N-{4-hydroxy-6-[N-(1-(R)-phenyl-2-carboxyethyl)amino]-1,3,5-triazin-2-yl}-L-4-(N,N-dimethylcarbamyloxy)phenylalanine;

N-{4-hydroxy-6-[N-(1-phenylethyl)amino]-1,3,5-triazin-2-yl}-L-4-(N,N-dimethylcarbamyloxy)phenylalanine;

N-{4-hydroxy-6-[N-(1-phenyl-1-ethoxycarbonylmethyl)amino]-1,3,5-triazin-2-yl}-L-4-(N,N-dimethylcarbamyloxy)phenylalanine;

N-{4-chloro-6-[N-(benzyl)-N-(1-carboxy-2-phenylethyl)amino]-1,3,5-triazin-2-yl}-L-4-(N,N-dimethylcarbamyloxy)phenylalanine;

N-{4-[N-(4-(3,5-dioxopiperazin-1-ylsulfonyl)phenyl)amino]-1,3,5-triazin-2-yl}-L-4-(N,N-dimethylcarbamyloxy)phenylalanine;

N-{4-[N-(pyridin-4-ylmethyl)amino]-1,3,5-triazin-2-yl}-L-4-(N,N-dimethylcarbamyloxy)phenylalanine;

N-{4-[N-(2-(4-benzylpiperazin-1yl)ethyl)amino]-1,3,5-triazin-2-yl}-L-4-(N,N-dimethylcarbamyloxy)phenylalanine;

N-{4-(N,N-dimethylamino)-1,3,5-triazin-2-yl}-L-4-(N,N-dimethylcarbamyloxy)phenylalanine;

N-{4-(N-(2-morpholin-4-ylethyl)amino)-1,3,5-triazin-2-yl}-L-4-(N,N-dimethylcarbamyloxy)phenylalanine;

N-{4-(N-(2-phenoxyethyl)amino)-1,3,5-triazin-2-yl}-L-4-(N,N-dimethylcarbamyloxy)phenylalanine;

N-{4-[N-(2-carboxy-1-(R)-phenylethyl)amino]-1,3,5-triazin-2-yl}-L-4-(N,N-dimethylcarbamyloxy)phenylalanine;

N-{4-[N-(1-ethoxycarbonyl-1-phenylmethyl)amino]-1,3,5-triazin-2, yl}-L-4-(N,N-dimethylcarbamyloxy)phenylalanine;

N-{4-[N-(1-carboxy-3-phenylpropyl)amino]-1,3,5-triazin-2-yl}-L-4-(N,N-dimethylcarbamyloxy)phenylalanine;

N-{4-[N-(1-phenylethyl)amino]-1,3,5-triazin-2-yl}-L-4-(N,N-dimethylcarbamyloxy)phenylalanine;

N-{4-[N-(2-carboxy-1-phenylethyl)amino]-1,3,5-triazin-2-yl}-L-4-(N,N-dimethylcarbamyloxy)phenylalanine;

N-{4-(N-2-methylpropylamino)-6-(4-phenylpiperazin-1-yl)-1,3,5-triazin-2-yl}-L-4-(N,N-dimethylcarbamyloxy)phenylalanine;

N-{4-(N-2-methylpropylamino)-6-(4-acetylpiperazin-1-yl)-1,3,5-triazin-2-yl}-L-4-(N,N-dimethylcarbamyloxy)phenylalanine;

N-{4-(N-6-nitrobenzthiazol-2-ylamino)-6-(piperidin-1-yl)-1,3,5-triazin-2-yl}-L-4-(N,N-dimethylcarbamyloxy)phenylalanine;

N-{4-(N-furan-2-ylmethylamino)-6-(piperidin-1-yl)-1,3,5-triazin-2-yl}-L-4-(N,N-dimethylcarbamyloxy)phenylalanine;

N-{4-(N-1-phenylethylamino)-6-(piperidin-1-yl)-1,3,5-triazin-2-yl}-L-4-(N,N-dimethylcarbamyloxy)phenylalanine;

N-{4-(N-4-chlorobenzylamino)-6-(piperidin-1-yl)-1,3,5-triazin-2-yl}-L-4-(N,N-dimethylcarbamyloxy)phenylalanine;

N-{4-(piperidin-1-yl)-6-(4-acetylpiperazin-1-yl)-1,3,5-triazin-2-yl}-L-4-(N,N-dimethylcarbamyloxy)phenylalanine;

N-{4-(N-4-aminosulfonylbenzylamino)-6-(piperidin-1-yl)-1,3,5-triazin-2-yl}-L-4-(N,N-dimethylcarbamyloxy)phenylalanine;

N-{4-(N-benzylamino)-6-(4-acetylpiperazin-1-yl)-1,3,5-triazin-2-yl}-L-4-(N,N-dimethylcarbamyloxy)phenylalanine;

N-{4-(N-cyclopentylamino)-6-(4-acetylpiperazin-1-yl)-1,3,5-triazin-2-yl}-L-4-(N,N-dimethylcarbamyloxy)phenylalanine;

N-{4-chloro-6-(4-benzylpiperidin-1-yl)-1,3,5-triazin-2-yl}-L-4-(N,N-dimethylcarbamyloxy)phenylalanine;

N-{4-chloro-6-(5-ethyl-2-methylpiperidin-1-yl)-1,3,5-triazin-2-yl}-L-4-(N,N-dimethylcarbamyloxy)phenylalanine;

N-{4-chloro-6-(4-phenylpiperazin-1-yl)-1,3,5-triazin-2-yl}-L-4-(N,N-dimethylcarbamyloxy)phenylalanine;

N-{4-chloro-6-[4-(3,4-methylenedioxybenzyl)piperazin-1-yl]-1,3,5-triazin-2-yl}-L-4-(N,N-dimethylcarbamyloxy)phenylalanine;

N-{4-chloro-6-(4-diphenylmethylpiperazin-1-yl)-1,3,5-triazin-2-yl}-L-4-(N,N-dimethylcarbamyloxy)phenylalanine;

N-{4-chloro-6-(4-acetylpiperazin-1-yl)-1,3,5-triazin-2-yl}-L-4-(N,N-dimethylcarbamyloxy)phenylalanine;

N-{4-chloro-6-(3-methylpiperidin-1-yl)-1,3,5-triazin-2-yl}-L-4-(N,N-dimethylcarbamyloxy)phenylalanine;

N-{4-chloro-6-(3,5-dimethylmorpholin-4-yl)-1,3,5-triazin-2-yl}-L-4-(N,N-dimethylcarbamyloxy)phenylalanine;

N-{4-(N-cyclohexylamino-6-(3,5-dimethylmorpholin-4-yl)-1,3,5-triazin-2-yl}-L-4-(N,N-dimethylcarbamyloxy)phenylalanine;

N-{4-[N-methyl-N-(4-methylphenylsulfonyl)amino]-6-(4-cyclohexyl -piperazin-1-yl)-1,3,5-triazin-2-yl}-L-4-(N,N-dimethylcarbamyloxy)-phenylalanine;

N-{4-[N-methyl-N-(4-methylphenylsulfonyl)amino]-6-(3-methyl piperidin-1-yl)-1,3,5-triazin-2-yl}-L-4-(N,N-dimethylcarbamyloxy)-phenylalanine;

N-{4-[N-(2-(4-aminosulfonylphenyl)ethyl)amino]-6-(piperidin-1-yl)-1,3,5-triazin-2-yl}-L-4-(N,N-dimethylcarbamyloxy)phenylalanine;

N-{4-chloro-6-[2-(4-benzylpiperazin-1-yl)ethyl)amino]-1,3,5-triazin-2-yl}-L-4-(N,N-dimethylcarbamyloxy)phenylalanine;

N-{4-chloro-6-[4-(isopropylaminocarbonylmethyl)piperazin-1-yl]-1,3,5-triazin-2-yl}-L-4-(N,N-dimethylcarbamyloxy)phenylalanine;

N-{4-chloro-6-[4-(1-phenylethyl)piperazin-1-yl]-1,3,5-triazin-2-yl}-L-4-(N,N-dimethylcarbamyloxy)phenylalanine;

N-{4-chloro-6-[4-(2-phenylethyl)piperazin-1-yl]-1,3,5-triazin-2-yl}-L-4-(N,N-dimethylcarbamyloxy)phenylalanine;

N-{4-chloro-6-[4-(furan-2-ylcarbonyl)piperazin-1-yl]-1,3,5-triazin-2-yl}-L-4-(N,N-dimethylcarbamyloxy)phenylalanine;

N-{4-chloro-6-[4-(1-phenylpropen-1-yl)piperazin-1-yl]-1,3,5-triazin-2-yl}-L-4-(N,N-dimethylcarbamyloxy)phenylalanine;

N-{4-[4-(isopropylaminocarbonylmethyl)piperazin-1-yl]-1,3,5-triazin-2-yl}-L-4-(N,N-dimethylcarbamyloxy)phenylalanine;

N-{4-[4-(2-phenylethyl)piperazin-1-yl]-1,3,5-triazin-2-yl}-L-4-(N,N-dimethylcarbamyloxy)phenylalanine;

N-{4-[4-(furan-2-ylcarbonyl)piperazin-1-yl]-1,3,5-triazin-2-yl}-L-4-(N,N-dimethylcarbamyloxy)phenylalanine;

N-{4-[4-(2-morpholin-4-ylethyl)piperazin-1-yl]-1,3,5-triazin-2-yl}-L-4-(N,N-dimethylcarbamyloxy)phenylalanine;

N-{4-chloro-6-(1,2,3,4-tetrahydroisoquinolin-2-yl)-1,3,5-triazin-2-yl}-L-4-(N,N-dimethylcarbamyloxy)phenylalanine;

N-{4-hydroxy-6-(1,2,3,4-tetrahydroisoquinolin-2-yl)-1,3,5-triazin-2-yl}-L-4-(N,N-dimethylcarbamyloxy)phenylalanine;

N-{4-chloro-6-[4-(ethoxycarbonylmethyl)piperazin-1-yl]-1,3,5-triazin-2-yl}-L-4-(N,N-dimethylcarbamyloxy)phenylalanine;

N-{4-hydroxy-6-[4-(ethoxycarbonylmethyl)piperazin-1-yl]-1,3,5-triazin-2-yl}-L-4-(N,N-dimethylcarbamyloxy)phenylalanine;

N-{4-chloro-6-(piperazin-1-yl)-1,3,5-triazin-2-yl}-L-4-(N,N-dimethylcarbamyloxy)phenylalanine;

N-{4-chloro-6-[4-(2-methoxyethyl)piperazin-1-yl]-1,3,5-triazin-2-yl}-L-4-(N,N-dimethylcarbamyloxy)phenylalanine;

N-{4-chloro-6-(2-ethoxycarbonylpiperidin-1-yl]-1,3,5-triazin-2-yl}-L-4-(N,N-dimethylcarbamyloxy)phenylalanine;

N-{4-chloro-6-[2-(ethoxycarbonylmethyl)-3-oxopiperazin-1-yl]-1,3,5-triazin-2-yl}-L-4-(N,N-dimethylcarbamyloxy)phenylalanine;

N-{4-hydroxy-6-[2-(ethoxycarbonylmethyl)-3-oxopiperazin-1-yl]-1,3,5-triazin-2-yl}-L-4-(N,N-dimethylcarbamyloxy)phenylalanine;

N-{4-chloro-6-(3-ethoxycarbonylpiperidin-1-yl]-1,3,5-triazin-2-yl}-L-4-(N,N-dimethylcarbamyloxy)phenylalanine;

N-{4-hydroxy-6-(3-(R)methoxycarbonyl-1,2,3,4-tetrahydroisoquinolin-1-yl)-1,3,5-triazin-2-yl}-L-4-(N,N-dimethylcarbamyloxy)-phenylalanine;

N-{4-chloro-6-(3-methoxycarbonyl-1,2,3,4-tetrahydro isoquinolin-1-yl)-1,3,5-triazin-2-yl}-L-4-(N,N-dimethylcarbamyloxy)-phenylalanine;

N-{4-hydroxy-6-(3-methoxycarbonyl-1,2,3,4-tetrahydroisoquinolin-1-yl)-1,3,5-triazin-2-yl}-L-4-(N,N-dimethylcarbamyloxy)-phenylalanine;

N-{4-(1,2,3,4-tetrahydroisoquinolin-2-yl)-1,3,5-triazin-2-yl}-L-4-(N,N-dimethylcarbamyloxy)phenylalanine;

N-{4-[4-(ethoxycarbonylmethyl)piperazin-1-yl]-1,3,5-triazin-2-yl}-L-4-(N,N-dimethylcarbamyloxy)phenylalanine;

N-{4-(piperazin-1-yl]-1,3,5-triazin-2-yl}-L-4-(N,N-dimethylcarbamyloxy)phenylalanine;

N-{4-(2-ethoxycarbonylpiperidin-1-yl]-1,3,5-triazin-2-yl}-L-4-(N,N-dimethylcarbamyloxy)phenylalanine;

N-{4-[2-(ethoxycarbonylmethyl)-3-oxopiperazin-1-yl]-1,3,5-triazin-2-yl}-L-4-(N,N-dimethylcarbamyloxy)phenylalanine;

N-{4-(3-carboxy-1,2,3,4-tetrahydroisoquinolin-2-yl)-1,3,5-triazin-2-yl}-L-4-(N,N-dimethylcarbamyloxy)phenylalanine;

N-{6-[N-(2-methylpropyl)-N-(4-methylphenylsulfonyl)amino]-pyrimidin-4-yl}-L-4-(N,N-dimethylcarbamyloxy)phenylalanine;

N-{6-[N-(methyl)-N-(4-methylphenylsulfonyl)amino]-pyrimidin-4-yl}-L-4-(N,N-dimethylcarbamyloxy)phenylalanine;

N-{6-[N-(2-phenylethyl)amino]pyrimidin-4-yl}-L-4-(N,N-dimethylcarbamyloxy)phenylalanine;

N-{6-[N-(methyl)-N-(2-pyridin-2-ylethyl)amino]pyrimidin-4-yl}-L-4-(N,N-dimethylcarbamyloxy)phenylalanine;

N-{6-[N-(methyl)-N-(benzyl)amino]pyrimidin-4-yl}-L-4-(N,N-dimethylcarbamyloxy)phenylalanine;

N-{6-(4-acetylpiperazin-1-yl)pyrimidin-4-yl}-L-4-(N,N-dimethylcarbamyloxy)phenylalanine;

N-{6-1N-(methyl)-N-(pyridin-3-ylmethyl)amino]pyrimidin-4-yl}-L-4-(N,N-dimethylcarbamyloxy)phenylalanine;

N-{6-[N-(methyl)-N-(2-(3,4-dimethoxyphenyl)ethyl)amino]pyrimidin-4-yl}-L-4-(N,N-dimethylcarbamyloxy)phenylalanine;

N-{6-[N-(methyl)-N-(2-phenylethyl)amino]pyrimidin-4-yl}-L-4-(N,N-dimethylcarbamyloxy)phenylalanine;

N-{6-[N-(2-methyl-2-phenylethyl)amino]pyrimidin-4-yl}-L-4-(N,N-dimethylcarbamyloxy)phenylalanine;

N-{6-[4-(2-propylaminocarbonylmethyl)piperazin-1-yl]pyrimidin-4-yl}-L-4-(N,N-dimethylcarbamyloxy)phenylalanine;

N-{6-[4-(2-morpholin-4-ylethyl)piperazin-1-yl]pyrimidin-4-yl}-L-4-(N,N-dimethylcarbamyloxy)phenylalanine;

N-{6-[N-(2-phenylethyl)amino]pyrimidin-4-yl}-L-4-(N,N-dimethylcarbamyloxy)phenylalanine;

and pharmaceutically acceptable salts thereof.

DETAILED DESCRIPTION OF THE INVENTION

As above, this invention relates to compounds which inhibit leukocyte adhesion and, in particular, leukocyte adhesion mediated by VLA-4. However, prior to describing this invention in further detail, the following terms will first be defined.

Definitions

As used herein, "alkyl" refers to alkyl groups preferably having from 1 to 10 carbon atoms and more preferably 1 to 6 carbon atoms. This term is exemplified by groups such as methyl, t-butyl, n-heptyl, octyl and the like.

"Substituted alkyl" refers to an alkyl group, preferably of from 1 to 10 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, $—OS(O)_2$-alkyl, $—OS(O)_2$- substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —NRS$(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl —$SO_2$-heteroaryl, —$SO_2$-substituted heteroaryl, —$SO_2$-heterocyclic, —$SO_2$-substituted heterocyclic and —$SO_2$NRR where R is hydrogen or alkyl.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Alkenoxy" refers to the group "alkenyl-O—".

"Substituted alkenoxy" refers to the group "substituted alkenyl-O-".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)— cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1-2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —NRS$(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkenyl groups having amino groups blocked by conventional blocking groups such as Boc, Cbz, formyl, and the like or alkenyl/substituted alkenyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2NRR$ where R is hydrogen or alkyl.

"Alkynyl" refers to alkynyl group preferably having from 2 to 10 carbon atoms and more preferably 3 to 6 carbon atoms and having at least 1 and preferably from 1-2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2NRR$ where R is hydrogen or alkyl.

"Amidino" refers to the group $H_2NC$(═NH)— and the term "alkylamidino" refers to compounds having 1 to 3 alkyl groups (e.g., alkylHNC(═NH)—).

"Thioamidino" refers to the group RSC(═NH)— where R is hydrogen or alkyl.

"Amino" refers to the group —$NH_2$.

"Substituted amino" refers to the group —NRR, where each R group is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic, provided that both R groups are not hydrogen; or the R groups can be joined together with the nitrogen atom to form a heterocyclic or substituted heterocyclic ring.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the groups —$NRSO_2$alkyl, —$NRSO_2$substituted alkyl, —$NRSO_2$cycloalkyl, —$NRSO_2$substituted cycloalkyl, —$NRSO_2$alkenyl, —$NRSO_2$substituted alkenyl, —$NRSO_2$alkynyl, —$NRSO_2$substituted alkynyl, —$NRSO_2$aryl, —$NRSO_2$substituted aryl, —$NRSO_2$heteroaryl, —$NRSO_2$substituted heteroaryl, —$NRSO_2$heterocyclic, and —$NRSO_2$substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the groups —$NRSO_2O$-alkyl, —$NRSO_2O$-substituted alkyl, —$NRSO_2O$-alkenyl, —$NRSO_2O$-substituted alkenyl, —$NRSO_2O$-alkynyl, —$NRSO_2O$-substituted alkynyl, —$NRSO_2O$-cycloalkyl, —$NRSO_2O$-substituted cycloalkyl, —$NRSO_2O$-aryl, —$NRSO_2O$ -substituted aryl, —$NRSO_2O$-heteroaryl, —$NRSO_2O$-substituted heteroaryl; —$NRSO_2O$-heterocyclic, and —$NRSO_2O$-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)$NH_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxysulfonylamino" refers to the groups —$OSO_2NH_2$, —$OSO_2$NRR, —$OSO_2$NR-alkyl, —$OSO_2$NR-substituted alkyl, —$OSO_2$NR-alkenyl, —$OSO_2$NR-substituted alkenyl, —$OSO_2$NR-alkynyl, —$OSO_2$NR-substituted alkynyl, —$OSO_2$NR-cycloalkyl, —$OSO_2$NR-substituted cycloalkyl, —$OSO_2$NR-aryl, —$OSO_2$NR-substituted aryl, —$OSO_2$NR-heteroaryl, —$OSO_2$NR-substituted heteroaryl, —$OSO_2$NR-heterocyclic, and —$OSO_2$NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxysulfonyl" refers to the groups alkyl-$SO_2$O—, substituted alkyl-$SO_2$O—, alkenyl-$SO_2$O—, substituted alkenyl-$SO_2$O—, alkynyl-$SO_2$O—, substituted alkynyl-$SO_2$O—, aryl-$SO_2$O—, substituted aryl-$SO_2$O—, cycloalkyl-$SO_2$O—, substituted cycloalkyl-$SO_2$O—, heteroaryl-$SO_2$O—, substituted heteroaryl-$SO_2$O—, heterocyclic-$SO_2$O—, and substituted heterocyclic-$SO_2$O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)$NH_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted, cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the groups —$NRSO_2$NRR, —$NRSO_2$NR-alkyl, —$NRSO_2$NR-substituted alkyl, —$NRSO_2$NR-alkenyl, —$NRSO_2$NR-substituted alkenyl, —$NRSO_2$NR-alkynyl, —$NRSO_2$NR-substituted alkynyl, —$NRSO_2$NR-aryl, —$NRSO_2$NR-substituted aryl, —$NRSO_2$NR-cycloalkyl, —$NRSO_2$NR-substituted cycloalkyl, —$NRSO_2$NR-heteroaryl, and —$NRSO_2$NR-substituted heteroaryl, —$NRSO_2$NR-heterocyclic, and —$NRSO_2$NR-substituted heterocyclic, where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7yl, and the like). Preferred aryls include phenyl and naphthyl.

Substituted aryl refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$S(O)_2$-alkyl, —$S(O)_2$-substituted alkyl, —$S(O)_2$-cycloalkyl, —$S(O)_2$-substituted cycloalkyl, —$S(O)_2$-alkenyl, —$S(O)_2$-substituted alkenyl, —$S(O)_2$-aryl, —$S(O)_2$-substituted aryl, —$S(O)_2$-heteroaryl, —$S(O)_2$-substituted heteroaryl, —$S(O)_2$-heterocyclic, —$S(O)_2$-substituted heterocyclic, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —NRS(O)-alkyl, —$NRS(O)_2$-substituted alkyl, —$NRS(O)_2$- aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$ —NR-alkyl, —$NRS(O)_2$—NR-substituted alkyl, —$NRS(O)_2$ —NR-aryl, —$NRS(O)_2$—NR-substituted aryl, —$NRS(O)_2$ —NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —$SO_2$NRR where R is hydrogen or alkyl.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$S(O)_2$-alkyl, —$S(O)_2$-substituted alkyl, —$S(O)_2$-cycloalkyl, —$S(O)_2$-substituted cycloalkyl, —$S(O)_2$-alkenyl, —$S(O)_2$-substituted alkenyl, —$S(O)_2$-aryl, —$S(O)_2$-substituted aryl, —$S(O)_2$-heteroaryl, —$S(O)_2$-substituted heteroaryl, —$S(O)_2$-heterocyclic, —$S(O)_2$-substituted heterocyclic, —$OS(O)_2$-alkyl, —$OS(O)_2$- substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —NRS(O)-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$ —NR-aryl, —$NRS(O)_2$—NR-substituted aryl, —$NRS(O)_2$ —NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —$SO_2$NRR where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclooctyl and the like. Excluded from this definition are multi-ring alkyl groups such as adamantanyl, etc.

"Cycloalkenyl" refers to cyclic alkenyl groups of from 3 to 8 carbon atoms having single or multiple unsaturation but which are not aromatic.

"Substituted cycloalkyl" and "substituted cycloalkenyl" refer to a cycloalkyl and cycloalkenyl groups, preferably of from 3 to 8 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —NRS(O)-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$ —NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino; mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Cycloalkoxy" refers to —O-cycloalkyl groups.

"Substituted cycloalkoxy" refers to —O-substituted cycloalkyl groups.

"Cycloalkenoxy" refers to —O-cycloalkenyl groups.

"Substituted cycloalkenoxy" refers to —O-substituted cycloalkenyl groups.

"Guanidino" refers to the groups —NRC(═NR)NRR, —NRC(═NR)NR-alkyl, —NRC(═NR)NR-substituted alkyl, —NRC(═NR)NR-alkenyl, —NRC(═NR)NR-substituted alkenyl, —NRC(═NR)NR-alkynyl, —NRC(═NR)NR-substituted alkynyl, —NRC(═NR)NR-aryl, —NRC(═NR)NR-substituted aryl, —NRC(═NR)NR-cycloalkyl, —NRC(═NR)NR-heteroaryl, —NRC(═NR)NR-substituted heteroaryl, —NRC(═NR)NR-heterocyclic, and —NRC(═NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Guanidinosulfone" refers to the groups —NRC(═NR)NRSO$_2$-alkyl, —NRC(═NR)NRSO$_2$-substituted alkyl, —NRC(═NR)NRSO$_2$-alkenyl, —NRC(═NR)NRSO$_2$-substituted alkenyl, —NRC(═NR)NRSO$_2$-alkynyl, —NRC(═NR)NRSO$_2$-substituted alkynyl, —NRC(═NR)NRSO$_2$-aryl, —NRC(═NR)NRSO$_2$-substituted aryl, —NRC(═NR)NRSO$_2$-cycloalkyl, —NRC(═NR)NRSO$_2$-substituted cycloalkyl, —NRC(═NR)NRSO$_2$-heteroaryl, and —NRC(═NR)NRSO$_2$-substituted heteroaryl, —NRC(═NR)NRSO$_2$-heterocyclic, and —NRC(═NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from oxygen, nitrogen and sulfur within the ring or oxides thereof. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$— NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from nitrogen, sulfur or oxygen within the ring wherein, in fused ring systems, one or more of the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —NRS $(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2NRR$ where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Thiol" refers to the group —SH.

"Thioalkyl" refers to the groups —S-alkyl

"Substituted thioalkyl" refers to the group —S-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and

"substituted thioheterocyclic" refers to the group —S-substituted heterocyclic.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

In a preferred method of synthesis, the compounds of this invention are prepared by coupling an amino acid derivative of the formula:

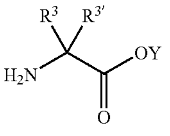

where $R^3$ and $R^{3'}$ are as defined herein and Y is an alkyl group such as methyl, ethyl and the like, with a suitably functionalized aryl, heteroaryl, cycloalkyl or cycloalkenyl intermediate. For example, such coupling reactions may be performed by displacing a leaving group, such as chloro, bromo, iodo, tosyl and the like, from the aryl, heteroaryl, cycloalkyl or cycloalkenyl intermediate with the amino group of the amino acid derivative; or by reductive alkylation of the amino group of amino acid derivative with a carbonyl-functionalized intermediate.

Such coupling reactions are well-known to those skilled in the art.

By way of illustration, the synthesis of some representative compounds of formula IIb wherein B is a substituted 1,3,5-triazine, Q is —NH—, $R^{3'}$ is hydrogen, and X is alkoxy or hydroxy is shown in Scheme 1 below.

Scheme 1

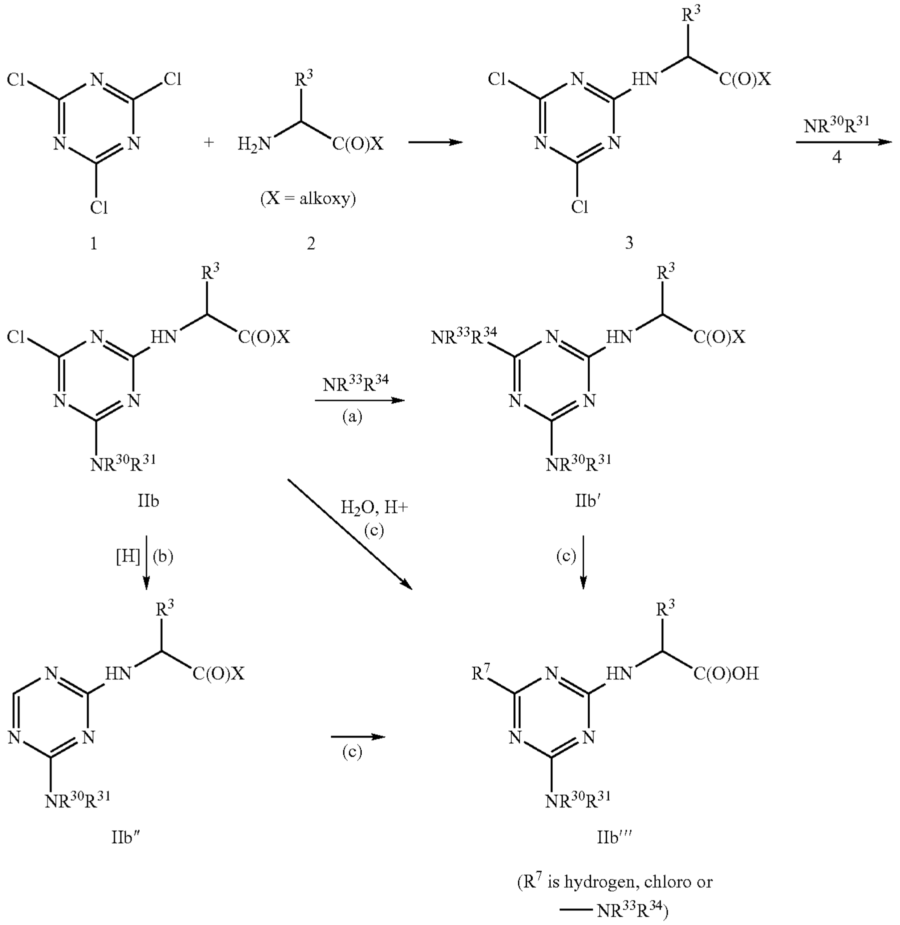

A compound of formula IIb where B is a triazine ring carrying a chloro, hydrogen, or substituted amino group at the 4-position and substituted amino group at the 6-position can prepared as shown in Scheme 1 above.

Reaction of 2,4,6-trichloro-1,3,5-triazine 1 (commercially available from Aldrich Chemical Company; Milwaukee, Wis. USA) with about one molar equivalent of an amino acid derivative of the formula:

$H_2N—CH(R^3)C(O)X$ 2 where $R^3$ is as defined in the Summary of the Invention and X is alkoxy such as methoxy, ethoxy, or tert-butyoxy and the like, in the presence of a trialkylamine, such as diisopropylethylamine (DIEA), provides a compound of formula 3. This reaction is typically conducted in an inert solvent such as tetrahydrofuran, at a temperature ranging from about 0° C. to about ambient temperature for about 5 min. to about 6 hours, preferably 2 hours.

Compound 3 is then reacted with an amine of formula 4 wherein $R^{30}$ and $R^{3'}$ are as defined above to provide a compound of formula IIb wherein the triazine ring is substituted with a chloro at the 4-position and a substituted amino at the 6-position. The reaction is carried out in the presence of a non-nucleophilic base such as N,N-diisopropylethylamine, pyridine, and the like and in an inert solvent such as N,N-dimethylformamide, tetrahydrofuran, and the like.

A compound of formula IIb can be converted to other compounds of formula IIb by methods well known in the art. For example, as shown in method (a), reaction of a compound of formula IIb with an amine of formula $NR^{33}R^{34}$ (wherein $R^{33}$ and $R^{34}$ are as defined above) provides a compound of formula II' wherein the triazine ring is substituted with a substituted amino group at the 4 and the 6-positions. As shown in method (b), a compound of formula IIb with a chloro group in the triazine ring can hydrogenated to provide a corresponding de-chlorinated compound of formula IIb". Lastly, as shown in method (c), compounds of formulae IIb, IIb', and IIb" where X is alkoxy can be converted to a corresponding compound of formula IIb'" where X is hydroxy under acidic hydrolysis reaction condition. Suitable acids are hydrochloric acid, trifluoroacetic acid, and the like.

Other heteroaryls may also be employed in the above described reactions including, but not limited to, 2-chloro-4-methyl-3-nitropyridine, 2-chloro-3-nitropyridine (Aldrich Chemical Co.); 4-chloro-3-nitropyridine (*J. Med. Chem.* 1989, 32, 2474-2485); 4-chloro-5-nitroimidazole (*J. Chem. Soc.* 1930, 268); and the like, to provide compounds of this invention.

The amino acid derivatives employed in the above reactions are either known compounds or compounds that can be prepared from known compounds by conventional synthetic procedures. For example, amino acid derivatives can be prepared by C-alkylating commercially available diethyl 2-acetamidomalonate (Aldrich, Milwaukee, Wis., USA) with an alkyl or substituted alkyl halide. This reaction is typically conducted by treating the diethyl 2-acetamidomalonate with at least one equivalent of sodium ethoxide and at least one equivalent of an alkyl or substituted alkyl halide in refluxing ethanol for about 6 to about 12 hours. The resulting C-alkylated malonate is then deacetylated, hydrolyzed and decarboxylated by heating in aqueous hydrochloric acid at reflux for about 6 to about 12 hours to provide the amino acid, typically as the hydrochloride salt.

Examples of amino acid derivatives suitable for use in the above reactions include, but are not limited to, L-alanine methyl ester, L-isoleucine methyl ester, L-leucine methyl ester, L-valine methyl ester, β-tert-butyl-L-aspartic acid methyl ester, L-asparagine tert-butyl ester, ε-Boc-L-lysine methyl ester, ε-Cbz-L-lysine methyl ester, γ-tert-butyl-L-glutamic acid methyl ester, L-glutamine tert-butyl ester, L-(N-methyl)histidine methyl ester, L-(N-benzyl)histidine methyl ester, L-methionine methyl ester, L-(O-benzyl)serine methyl ester, L-tryptophan methyl ester, L-phenylalanine methyl ester, L-phenylalanine isopropyl ester, L-phenylalanine benzyl ester, L-phenylalaninamide, N-methyl-L-phenylalanine benzyl ester, 3-carboxy-D,L-phenylalanine methyl ester, 4-carboxy-D,L-phenylalanine methyl ester, L-4-chlorophenylalanine methyl ester, L-4-(3-dimethylaminopropyloxy)-phenylalanine methyl ester, L-4-iodophenylalanine methyl ester, L-3,4-methylenedioxyphenylalanine methyl ester, L-3,4-ethylenedioxy-phenylalanine methyl ester, L-4-nitrophenylalanine methyl ester, t-tyrosine methyl ester, D,L-homophenylalanine methyl ester, L-(O-methyl)tyrosine methyl ester, L-(O-tert-butyl)tyrosine methyl ester, L-(O-benzyl)tyrosine methyl ester, L-3,5-diiodotyrosine methyl ester, L-3-iodotyrosine methyl ester, β-(1-naphthyl)-L-alanine methyl ester, β-(2-naphthyl)-L-alanine methyl ester, β-(2-thienyl)-L-alanine methyl ester, β-cyclohexyl-L-alanine methyl ester, β-(2-pyridyl)-L-alanine methyl ester, β-(3-pyridyl)-L-alanine methyl ester, β-(4-pyridyl)-L-alanine methyl ester, β-(2-thiazolyl)-D,L-alanine methyl ester, β-(1,2,4-triazol-3-yl)-D,L-alanine methyl ester, and the like.

If desired, of course, other esters or amides of the above-described compounds may also be employed.

Additionally, α-hydroxy and α-thio carboxylic acids may also be employed in the above-described reactions. Such compounds are well-known in the art and are either commercially available or may be prepared from commercially available starting materials using conventional reagents and reaction conditions.

In another preferred embodiment, compounds of this invention may be prepared by displacement of a leaving group as shown in Scheme 2:

Scheme 2

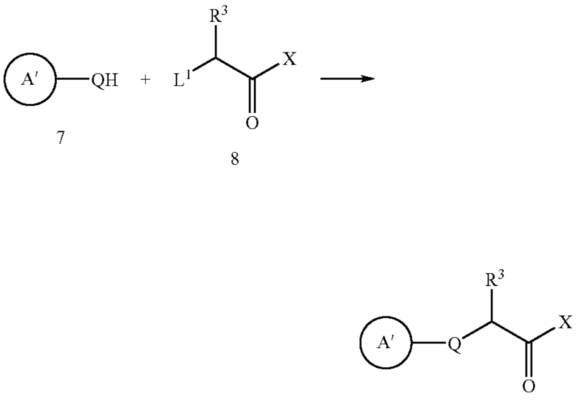

7 8 9 where $R^3$, Q and X are as defined herein; A' is cycloalkyl, substituted cycloalkyl, cycloalkenyl, substituted cycloalkenyl, aryl, substituted aryl, heterocyclic and substituted heterocyclic; and $L^1$ is a leaving group, such as chloro, bromo, iodo, sulfonate ester and the like.

Typically, this reaction is conducted by combining approximately stoichiometric equivalents of 7 and 8 in a suitable inert diluent such as water, dimethylsulfoxide (DMSO) and the like, with an excess of a suitable base such as sodium bicarbonate, sodium hydroxide, etc. to scavenge the acid generated by the reaction. The reaction is preferably conducted at from about 25° C. to about 100° C. until reaction completion which typically occurs within 1 to about 24 hours. This reaction is further described in U.S. Pat. No. 3,598,859, which is incorporated herein by reference in its entirety. Upon reaction completion, the product 9 is recovered by conventional methods including precipitation, chromatography, filtration and the like.

In still another alternative embodiment, compounds of this invention in which Q is $NR^4$ can be prepared by reductive amination of a suitable 2-oxocarboxylic acid ester, 10, such as a pyruvate ester, as shown in Scheme 3:

Scheme 3

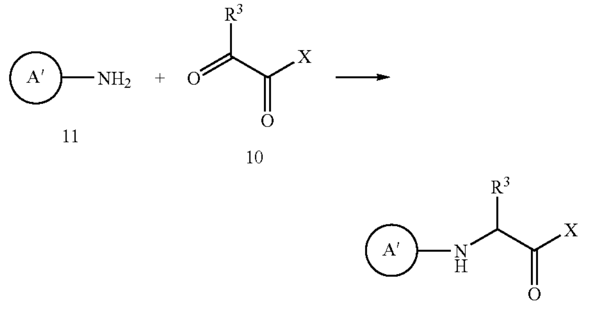

11 10 12 where A', $R^3$ and X are as defined herein.

Generally, this reaction is conducted by combining equamolar amounts of 10 and 11 in an inert diluent such as methanol, ethanol and the like under conditions which provide for imine formation (not shown). The imine formed is then reduced under conventional conditions by a suitable reducing agent such as sodium cyanoborohydride, $H_2$/palladium on carbon and the like to form the product 12. In a particularly preferred embodiment, the reducing agent is $H_2$/palladium on carbon which is incorporated into the initial reaction medium thereby permitting imine reduction in Situ in a one pot procedure to provide 12. The reaction is preferably conducted at from about 20° C. to about 80° C. at a pressure of from 1 to 10 atmospheres until reaction completion which typically occurs within 1 to about 24 hours. Upon reaction completion, the product 12 is recovered by conventional methods including chromatography, filtration and the like.

Alternatively, certain compounds of this invention can be prepared via a rhodium-catalyzed insertion reaction as shown in Scheme 4:

Scheme 4

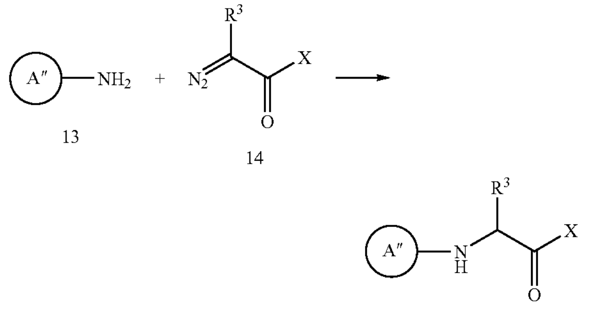

13 14 15 where A" is aryl, substituted aryl, heteroaryl and substituted heteroaryl, and $R^3$ and X (preferably alkoxy) are as defined herein. Typically, this reaction is conducted using rhodium acetate dimer, $Rh_2(OAc)_4$, in an inert diluent such as toluene at a temperature ranging from about 25° C. to about 80° C. for about 1 to 12 hours to afford 15. This reaction is described further in B. R. Henke et. al., *J. Med. Chem.* 1998, 41, 5020-5036 and references cited therein.

Similarly, certain compounds of this invention can be prepared by the copper-catalyzed coupling reaction shown in Scheme 5:

Scheme 5

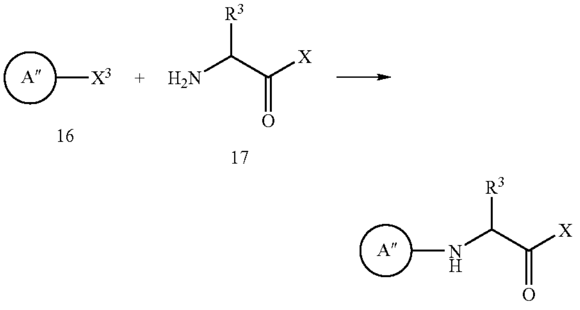

16 17 15 where A" is aryl, substituted aryl, heteroaryl and substituted heteroaryl, $X^3$ is halogen, such as chloro, bromo or iodo (preferably iodo), and $R^3$ and X (preferably alkoxy) are as defined herein. Typically, this reaction is conducted using copper iodide (CuI) and potassium carbonate in an inert diluent such as N,N-dimethyl acetamide (DMA) at a temperature ranging from about 60° C. to about 120° C. for about 12 to 36 hours to afford 15. This reaction is described further in D. Ma et. al., *J. Am. Chem. Soc.* 1998, 120, 12459-12467 and references cited therein.

For ease of synthesis, the compounds of this invention are typically prepared as an ester, i.e., where X is an alkoxy or substituted alkoxy group and the like. If desired, the ester group can be hydrolysed using conventional conditions and reagents to provide the corresponding carboxylic acid. Typically, this reaction is conducted by treating the ester with at least one equivalent of an alkali metal hydroxide, such as lithium, sodium or potassium hydroxide, in an inert diluent, such as methanol or mixtures of methanol and water, at a temperature ranging about 0° C. to about 24° C. for about 1 to about 12 hours. Alternatively, benzyl esters may be removed by hydrogenolysis using a palladium catalyst, such as palladium on carbon, and tert-butyl esters can be removed using formic acid to afford the corresponding carboxylic acid.

As will be apparent to those skilled in the art, other functional groups present on any of the substituents of the compounds of formulas I-VII can be readily modified or derivatized either before or after the above-described synthetic reactions using well-known synthetic procedures. For example, a nitro group present on a substituent of a compound of formula I-VII or an intermediate thereof may be readily reduced by hydrogenation in the presence of a palladium catalyst, such as palladium on carbon, to provide the corresponding amino group. This reaction is typically conducted at a temperature of from about 20° C. to about 50° C. for about 6 to about 24 hours in an inert diluent, such as methanol. Compounds having a nitro group on the $R^3$ and/or $R^{3'}$ substituent can be prepared, for example, by using a 4-nitrophenylalanine derivative and the like in the above-described coupling reactions.

Similarly, a pyridyl group can be hydrogenated in the presence of a platinum catalyst, such as platinum oxide, in an acidic diluent to provide the corresponding piperidinyl analogue. Generally, this reaction is conducted by treating the pyridine compound with hydrogen at a pressure ranging from about 20 psi to about 60 psi, preferably about 40 psi, in the presence of the catalyst at a temperature of about 20° C. to about 50° C. for about 2 to about 24 hours in an acidic diluent, such as a mixture of methanol and aqueous hydrochloric acid.

Additionally, when the $R^3$ and/or $R^3$ substituent of a compound of formula I-VII or an intermediate thereof contains a primary or secondary amino group, such amino groups can be further derivatized either before or after the above coupling reactions to provide, by way of example, amides, sulfonamides, ureas, thioureas, carbamates, secondary or tertiary amines and the like. Compounds having a primary amino group on the $R^3$ and/or $R^3$ substituent may be prepared, for example, by reduction of the corresponding nitro compound as described above.

By way of illustration, a compound of formula I-VII or an intermediate thereof having a substituent containing a primary or secondary amino group, such as where $R^3$ is a (4-aminophenyl)methyl group, can be readily N-acylated using conventional acylating reagents and conditions to provide the corresponding amide. This acylation reaction is typically conducted by treating the amino compound with at least one equivalent, preferably about 1.1 to about 1.2 equivalents, of a carboxylic acid in the presence of a coupling reagent such as a carbodiimide, BOP reagent (benzotriazol-1-yloxy-tris (dimethylamino)phosphonium hexafluorophosphonate) and the like, in an inert diluent, such as dichloromethane, chloroform, acetonitrile, tetrahydrofuran, N,N-dimethylformamide and the like, at a temperature ranging from about 0° C. to about 37° C. for about 4 to about 24 hours. Preferably, a promoter, such as N-hydroxysuccinimide, 1-hydroxy-benzotriazole and the like, is used to facilitate the acylation reaction. Examples of carboxylic acids suitable for use in this reaction include, but are not limited to, N-tert-butyloxycarbonylglycine, N-tert-butyloxycarbonyl-L-phenylalanine, N-tert-butyloxycarbonyl-L-aspartic acid benzyl ester, benzoic acid, N-tert-butyloxycarbonylisonipecotic acid, N-methylisonipecotic acid, N-tert-butyloxycarbonylnipecotic acid, N-tert-butyloxycarbonyl-L-tetrahydroisoquinoline-3-carboxylic acid, N-(toluene-4-sulfonyl)-L-proline and the like.

Alternatively, a compound of formula I-VII or an intermediate thereof containing a primary or secondary amino group can be N-acylated using an acyl halide or a carboxylic acid anhydride to form the corresponding amide. This reaction is typically conducted by contacting the amino compound with at least one equivalent, preferably about 1.1 to about 1.2 equivalents, of the acyl halide or carboxylic acid anhydride in an inert diluent, such as dichloromethane, at a temperature ranging from about −70° C. to about 40° C. for about 1 to about 24 hours. If desired, an acylation catalyst such as 4-(N, N-dimethylamino)pyridine may be used to promote the acylation reaction. The acylation reaction is preferably conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like.

Examples of acyl halides and carboxylic acid anhydrides suitable for use in this reaction include, but are not limited to, 2-methylpropionyl chloride, trimethylacetyl chloride, phenylacetyl chloride, benzoyl chloride, 2-bromobenzoyl chloride, 2-methylbenzoyl chloride, 2-trifluoro-methylbenzoyl chloride, isonicotinoyl chloride, nicotinoyl chloride, picolinoyl chloride, acetic anhydride, succinic anhydride, and the like. Carbamyl chlorides, such as N,N-dimethylcarbamyl chloride, N,N-diethylcarbamyl chloride and the like, can also be used in this reaction to provide ureas. Similarly, dicarbonates, such as di-tert-butyl dicarbonate, may be employed to provide carbamates.

In a similar manner, a compound of formula I-VII or an intermediate thereof containing a primary or secondary amino group may be N-sulfonated to form a sulfonamide using a sulfonyl halide or a sulfonic acid anhydride. Sulfonyl halides and sulfonic acid anhydrides suitable for use in this reaction include, but are not limited to, methanesulfonyl chloride, chloromethanesulfonyl chloride, p-toluenesulfonyl chloride, trifluoromethanesulfonic anhydride, and the like. Similarly, sulfamoyl chlorides, such as dimethylsulfamoyl chloride, can be used to provide sulfamides (e.g., $>N-SO_2-N<$).

Additionally, a primary and secondary amino group present on a substituent of a compound of formula I-VII or an intermediate thereof can be reacted with an isocyanate or a thioisocyanate to give a urea or thiourea, respectively. This reaction is typically conducted by contacting the amino compound with at least one equivalent, preferably about 1.1 to about 1.2 equivalents, of the isocyanate or thioisocyanate in an inert diluent, such as toluene and the like, at a temperature ranging from about 24° C. to about 37° C. for about 12 to about 24 hours. The isocyanates and thioisocyanates used in this reaction are commercially available or can be prepared from commercially available compounds using well-known synthetic procedures. For example, isocyanates and thioisocyanates are readily prepared by reacting the appropriate amine with phosgene or thiophosgene. Examples of isocyanates and thioisocyanates suitable for use in this reaction include, but are not limited to, ethyl isocyanate, n-propyl isocyanate, 4-cyanophenyl isocyanate, 3-methoxyphenyl isocyanate, 2-phenylethyl isocyanate, methyl thioisocyanate, ethyl thioisocyanate, 2-phenylethyl thioisocyanate, 3-phenylpropyl thioisocyanate, 3-(N,N-diethylamino)propyl thioisocyanate, phenyl thioisocyanate, benzyl thioisocyanate, 3-pyridyl thioisocyanate, fluorescein isothiocyanate (isomer 1) and the like.

Furthermore, when a compound of formula I-VII or an intermediate thereof contains a primary or secondary amino group, the amino group can be reductively alkylated using aldehydes or ketones to form a secondary or tertiary amino group. This reaction is typically conducted by contacting the amino compound with at least one equivalent, preferably about 1.1 to about 1.5 equivalents, of an aldehyde or ketone and at least one equivalent based on the amino compound of a metal hydride reducing agent, such as sodium cyanoborohydride, in an inert diluent, such as methanol, tetrahydrofuran, mixtures thereof and the like, at a temperature ranging from about 0° C. to about 50° C. for about 1 to about 72 hours. Aldehydes and ketones suitable for use in this reaction include, by way of example, benzaldehyde, 4-chlorobenzaldehyde, valeraldehyde and the like.

In a similar manner, when a compound of formula I-VII or an intermediate thereof has a substituent containing a hydroxyl group, the hydroxyl group can be further modified or derivatized either before or after the above coupling reactions to provide, by way of example, ethers, carbamates and the like. Compounds having a hydroxyl group on the $R^3$ substituent, for example, can be prepared using an amino acid derivative derived from tyrosine and the like in the above-described reactions.

By way of example, a compound of formula I-VII or an intermediate thereof having a substituent containing a hydroxyl group, such as where $R^3$ is a (4-hydroxyphenyl)

methyl group, can be readily O-alkylated to form ethers. This O-alkylation reaction is typically conducted by contacting the hydroxy compound with a suitable alkali or alkaline earth metal base, such as potassium carbonate, in an inert diluent, such as acetone, 2-butanone and the like, to form the alkali or alkaline earth metal salt of the hydroxyl group. This salt is generally not isolated, but is reacted in situ with at least one equivalent of an alkyl or substituted alkyl halide or sulfonate, such as an alkyl chloride, bromide, iodide, mesylate or tosylate, to afford the ether. Generally, this reaction is conducted at a temperature ranging from about 60° C. to about 150° C. for about 24 to about 72 hours. Preferably, a catalytic amount of sodium or potassium iodide is added to the reaction mixture when an alkyl chloride or bromide is employed in the reaction.

Examples of alkyl or substituted alkyl halides and sulfonates suitable for use in this reaction include, but are not limited to, tert-butyl bromoacetate, N-tert-butyl chloroacetamide, 1-bromoethylbenzene, ethyl α-bromophenylacetate, 2-(N-ethyl-N-phenylamino)ethyl chloride, 2-(N,N-ethylamino)ethyl chloride, 2-(N,N-diisopropylamino)ethyl chloride, 2-(N,N-dibenzylamino)ethyl chloride, 3-(N,N-ethylamino)propyl chloride, 3-(N-benzyl-N-methylamino) propyl chloride, N-(2-chloroethyl)morpholine, 2-(hexamethyleneimino)ethyl chloride, 3-(N-methylpiperazine)propyl chloride, 1-(3-chlorophenyl)-4-(3-chloropropyl) piperazine, 2-(4-hydroxy-4-phenylpiperidine)ethyl chloride, N-tert-butyloxycarbonyl-3-piperidinemethyl tosylate, and the like.

Alternatively, a hydroxyl group present on a substituent of a compound of formula I-VII or an intermediate thereof can be O-alkylating using the Mitsunobu reaction. In this reaction, an alcohol, such as 3-(N,N-dimethylamino)-1-propanol and the like, is reacted with about 1.0 to about 1.3 equivalents of triphenylphosphine and about 1.0 to about 1.3 equivalents of diethyl azodicarboxylate in an inert diluent, such as tetrahydrofuran, at a temperature ranging from about −10° C. to about 5° C. for about 0.25 to about 1 hour. About 1.0 to about 1.3 equivalents of a hydroxy compound, such as N-tert-butyltyrosine methyl ester, is then added and the reaction mixture is stirred at a temperature of about 0° C. to about 30° C. for about 2 to about 48 hours to provide the O-alkylated product.

In a similar manner, a compound of formula I-VII or an intermediate thereof containing an aryl hydroxy group can be reacted with an aryl iodide to provide a diaryl ether. Generally, this reaction is conducted by forming the alkali metal salt of the hydroxyl group using a suitable base, such as sodium hydride, in an inert diluent such as xylenes at a temperature of about −25° C. to about 10° C. The salt is then treated with about 1.1 to about 1.5 equivalents of cuprous bromide dimethyl sulfide complex at a temperature ranging from about 10° C. to about 30° C. for about 0.5 to about 2.0 hours, followed by about 1.1 to about 1.5 equivalents of an aryl iodide, such as sodium 2-iodobenzoate and the like. The reaction is then heated to about 70° C. to about 150° C. for about 2 to about 24 hours to provide the diaryl ether.

Additionally, a hydroxy-containing compound can also be readily derivatized to form a carbamate. In one method for preparing such carbamates; a hydroxy compound of formula I-VII or an intermediate thereof is contacted with about 1.0 to about 1.2 equivalents of 4-nitrophenyl chloroformate in an inert diluent, such as dichloromethane, at a temperature ranging from about −25° C. to about 0° C. for about 0.5 to about 2.0 hours. Treatment of the resulting carbonate with an excess, preferably about 2 to about 5 equivalents, of a trialkylamine, such as triethylamine, for about 0.5 to 2 hours, followed by about 1.0 to about 1.5 equivalents of a primary or secondary amine provides the carbamate. Examples of amines suitable for using in this reaction include, but are not limited to, piperazine, 1-methylpiperazine, 1-acetylpiperazine, morpholine, thiomorpholine, pyrrolidine, piperidine and the like.

Alternatively, in another method for preparing carbamates, a hydroxy-containing compound is contacted with about 1.0 to about 1.5 equivalents of a carbamyl chloride in an inert diluent, such as dichloromethane, at a temperature ranging from about 25° C. to about 70° C. for about 2 to about 72 hours. Typically, this reaction is conducted in the presence of a suitable base to scavenge the acid generated during the reaction. Suitable bases include, by way of example, tertiary amines, such as triethylamine, diisopropylethylamine, N-methylmorpholine and the like. Additionally, at least one equivalent (based on the hydroxy compound) of 4-(N,N-dimethylamino)pyridine is preferably added to the reaction mixture to facilitate the reaction. Examples of carbamyl chlorides suitable for use in this reaction include, by way of example, dimethylcarbamyl chloride, diethylcarbamyl chloride and the like.

Likewise, when a compound of formula I-VII or an intermediate thereof contains a primary or secondary hydroxyl group, such hydroxyl groups can be readily converted into a leaving group and displaced to form, for example, amines, sulfides and fluorides. Generally, when a chiral compound is employed in these reactions, the stereochemistry at the carbon atom attached to the derivatized hydroxyl group is typically inverted.

These reactions are typically conducted by first converting the hydroxyl group into a leaving group, such as a tosylate, by treatment of the hydroxy compound with at least one equivalent of a sulfonyl halide, such as p-toluenesulfonyl chloride and the like, in pyridine. This reaction is generally conducted at a temperature of from about 0° C. to about 70° C. for about 1 to about 48 hours. The resulting tosylate can then be readily displaced with sodium azide, for example, by contacting the tosylate with at least one equivalent of sodium azide in an inert diluent, such as a mixture of N,N-dimethylformamide and water, at a temperature ranging from about 0° C. to about 37° C. for about 1 to about 12 hours to provide the corresponding azido compound. The azido group can then be reduced by, for example, hydrogenation using a palladium on carbon catalyst to provide the amino ($—NH_2$) compound.

Similarly, a tosylate group can be readily displaced by a thiol to form a sulfide. This reaction is typically conducted by contacting the tosylate with at least one equivalent of a thiol, such as thiophenol, in the presence of a suitable base, such as 1,8-diazabicyclo[5.4.0]undec-7-ene (DBU), in an inert diluent, such as N,N-dimethylformamide, at a temperature of from about 0° C. to about 37° C. for about 1 to about 12 hours to provide the sulfide. Additionally, treatment of a tosylate with morpholinosulfur trifluoride in an inert diluent, such as dichloromethane, at a temperature ranging from about 0° C. to about 37° C. for about 12 to about 24 hours affords the corresponding fluoro compound.

Furthermore, a compound of formula I-VII or an intermediate thereof having a substituent containing an iodoaryl group, for example, when $R^3$ is a (4-iodophenyl)methyl group, can be readily converted either before or after the above coupling reactions into a biaryl compound. Typically, this reaction is conducted by treating the iodoaryl compound with about 1.1 to about 2 equivalents of an arylzinc iodide, such as 2-(methoxycarbonyl)-phenylzinc iodide, in the presence of a palladium catalyst, such as palladium tetra(triphenylphosphine), in an inert diluent, such as tetrahydrofuran, at a temperature ranging from about 24° C. to about 30° C. until reaction completion. This reaction is further described, for example, in Rieke, *J. Org. Chem.* 1991, 56, 1445. Additional methods for preparing biaryl derivatives are disclosed in International Publication No. WO 98/53817, published Dec. 3, 1998, the disclosure of which is incorporated herein by reference in its entirety.

In some cases, the compounds of formula I-VII or intermediates thereof may contain substituents having one or more sulfur atoms. When present, such sulfur atoms can be oxidized either before or after the above coupling reactions to provide a sulfoxide or sulfone compound using conventional reagents and reaction conditions. Suitable reagents for oxidizing a sulfide compound to a sulfoxide include, by way of example, hydrogen peroxide, 3-chloroperoxybenzoic acid (MCPBA), sodium periodate and the like. The oxidation reaction is typically conducted by contacting the sulfide compound with about 0.95 to about 1.1 equivalents of the oxidizing reagent in an inert diluent, such as dichloromethane, at a temperature ranging from about −50° C. to about 75° C. for about 1 to about 24 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent. Such reactions are described further in March, "*Advanced Organic Chemistry*", 4th Ed., pp. 1201-1202, Wiley Publisher, 1992.

Other procedures and reaction conditions for preparing the compounds of this invention are described in the examples set forth below.

Pharmaceutical Formulations

When employed as pharmaceuticals, the compounds of this invention are usually administered in the form of pharmaceutical compositions. These compounds can be administered by a variety of routes including oral, rectal, transdermal; subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I-VII above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders.

The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 40 mg of medicament are made as follows:

| Ineredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

FORMULATION EXAMPLE 9

An intravenous formulation may be prepared as follows:

| Ingredient | Quantity |
|---|---|
| Active Ingredient | 250.0 mg |
| Isotonic saline | 1000 ml |

FORMULATION EXAMPLE 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Utility

The compounds of this invention can be employed to bind VLA-4 ($\alpha_4\beta_1$ integrin) in biological samples and, accordingly have utility in, for example, assaying such samples for VLA-4. In such assays, the compounds can be bound to a solid support and the VLA-4 sample added thereto. The amount of VLA-4 in the sample can be determined by conventional methods such as use of a sandwich ELISA assay. Alternatively, labeled VLA-4 can be used in a competitive assay to measure for the presence of VLA-4 in the sample. Other suitable assays are well known in the art.

In addition, certain of the compounds of this invention inhibit, in vivo, adhesion of leukocytes to endothelial cells mediated by VLA-4 and, accordingly, can be used in the treatment of diseases mediated by VLA-4. Such diseases include inflammatory diseases in mammalian patients such as asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

The biological activity of the compounds identified above may be assayed in a variety of systems. For example, a compound can be immobilized on a solid surface and adhesion of cells expressing VLA-4 can be measured. Using such formats, large numbers of compounds can be screened. Cells suitable for this assay include any leukocytes known to express VLA-4 such as T cells, B cells, monocytes, eosinophils, and basophils. A number of leukocyte cell lines can also be used, examples include Jurkat and U937.

The test compounds can also be tested for the ability to competitively inhibit binding between VLA-4 and VCAM-1, or between VLA-4 and a labeled compound known to bind VLA-4 such as a compound of this invention or antibodies to VLA-4. In these assays, the VCAM-1 can be immobilized on a solid surface. VCAM-1 may also be expressed as a recombinant fusion protein having an Ig tail (e.g., IgG) so that binding to VLA-4 may be detected in an immunoassay. Alternatively, VCAM-1 expressing cells, such as activated endothelial cells or VCAM-1 transfected fibroblasts can be used. For assays to measure the ability to block adhesion to brain endothelial cells, the assays described in International Patent Application Publication No. WO 91/05038 are particularly preferred. This application is incorporated herein by reference in its entirety.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3H$, $^{125}I$, $^{35}S$, $^{14}C$, or $^{32}P$ labelled compounds or the like. Non-radioactive labels include ligands which bind to labelled antibodies, fluorophores, chemiluminescent agents, enzymes and antibodies which can serve as specific binding pair members for a labelled ligand. The choice of label depends on sensitivity required, ease of conjugation with the compound, stability requirements, and available instrumentation.

Appropriate in vivo models for demonstrating efficacy in treating inflammatory responses include EAE (experimental autoimmune encephalomyelitis) in mice, rats, guinea pigs or primates, as well as other inflammatory models dependent upon $\alpha 4$ integrins.

Compounds having the desired biological activity may be modified as necessary to provide desired properties such as improved pharmacological properties (e.g., in vivo stability, bio-availability), or the ability to be detected in diagnostic applications. For instance, inclusion of one or more D-amino acids in the sulfonamides of this invention typically increases in vivo stability. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83-93).

For diagnostic purposes, a wide variety of labels may be linked to the compounds, which may provide, directly or indirectly, a detectable signal. Thus, the compounds of the subject invention may be modified in a variety of ways for a variety of end purposes while still retaining biological activity. In addition, various reactive sites may be introduced at the terminus for linking to particles, solid substrates, macromolecules, or the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

In vitro uses include diagnostic applications such as monitoring inflammatory responses by detecting the presence of leukocytes expressing VLA-4. The compounds of this invention can also be used for isolating or labeling such cells. In addition, as mentioned above, the compounds of the invention can be used to assay for potential inhibitors of VLA-4/VCAM-1 interactions.

For in vivo diagnostic imaging to identify, e.g., sites of inflammation, radioisotopes are typically used in accordance with well known techniques. The radioisotopes may be bound to the peptide either directly or indirectly using intermediate functional groups. For instance, chelating agents such as diethylenetriaminepentacetic acid (DTPA) and ethylenediaminetetraacetic acid (EDTA) and similar molecules have been used to bind proteins to metallic ion radioisotopes.

The complexes can also be labeled with a paramagnetic isotope for purposes of in vivo diagnosis, as in magnetic resonance imaging (MRI) or electron spin resonance (ESR), both of which are well known. In general, any conventional method for visualizing diagnostic imaging can be used. Usually gamma- and positron-emitting radioisotopes are used for camera imaging and paramagnetic isotopes are used for MRI. Thus, the compounds can be used to monitor the course of amelioration of an inflammatory response in an individual. By measuring the increase or decrease in lymphocytes expressing VLA-4 it is possible to determine whether a particular therapeutic regimen aimed at ameliorating the disease is effective.

The pharmaceutical compositions of the present invention can be used to block or inhibit cellular adhesion associated with a number of diseases and disorders. For instance, a number of inflammatory disorders are associated with integrins or leukocytes. Treatable disorders include, e.g., transplantation rejection (e.g., allograft rejection), Alzheimer's disease, atherosclerosis, AIDS dementia, diabetes (including acute juvenile onset diabetes), retinitis, cancer metastases, rheumatoid arthritis, acute leukocyte-mediated lung injury (e.g., adult respiratory distress syndrome), asthma, nephritis, and acute and chronic inflammation, including atopic dermatitis, psoriasis, myocardial ischemia, and inflammatory bowel disease (including Crohn's disease and ulcerative colitis). In preferred embodiments the pharmaceutical compositions are used to treat inflammatory brain disorders, such as multiple sclerosis (MS), viral meningitis and encephalitis.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, *Immunology* (3d ed., Raven Press, 1993).

Another indication for the compounds of this invention is in treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. $CD8^+$ cells, CD4 cells and monocytes are all involved in the rejection of transplant tissues. Compounds of this invention which bind to alpha-4 integrin are useful, inter alia, to block alloantigen-induced immune responses in the donee thereby preventing such cells from participating in the destruction of the transplanted tissue or organ. See, e.g., Paul et al., *Transplant International* 9, 420-425 (1996); Georczynski et al., *Immunology* 87, 573-580 (1996); Georcyznski et al., *Transplant. Immunol.* 3, 55-61 (1995); Yang et al., *Transplantation* 60, 71-76 (1995); Anderson et al., *APMIS* 102, 23-27 (1994).

A related use for compounds of this invention which bind to VLA-4 is in modulating the immune response involved in "graft versus host" disease (GVHD). See e.g., Schlegel et al., *J. Immunol.* 155, 3856-3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

A further use of the compounds of this invention is inhibiting tumor metastasis. Several tumor cells have been reported to express VLA-4 and compounds which bind VLA-4 block adhesion of such cells to endothelial cells. Steinback et al., *Urol. Res.* 23, 175-83 (1995); Orosz et al., *Int. J. Cancer* 60, 867-71 (1995); Freedman et al., *Leuk. Lymphoma* 13, 47-52 (1994); Okahara et al., *Cancer Res.* 54, 3233-6 (1994).

A further use of the compounds of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals[16].

Pharmaceutical compositions of the invention are suitable for use in a variety of drug delivery systems. Suitable formulations for use in the present invention are found in *Remington's Pharmaceutical Sciences*, Mace Publishing. Company, Philadelphia, Pa., 17th ed. (1985).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871; 4,501,728 and 4,837,028 each of which is incorporated herein by reference.

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 μg to about 500 μg per kilogram body weight, preferably about 100 μg to about 300 μg per kilogram body weight. Suitable dosage ranges for intranasal administration are generally about 0.1 μg to 1 mg per kilogram body weight. Effective doses can be extrapolated from dose-response curves derived from in vitro or animal model test systems.

Compounds of this invention are also capable of binding or antagonizing the actions of $\alpha_6\beta_1$, $\alpha_9\beta_1$, $\alpha_4\beta_7$, $\alpha_d\beta_2$, $\alpha_e\beta_7$ integrins (although $\alpha_4\beta_1$, and $\alpha_9\beta_1$, are preferred in this invention). Accordingly, compounds of this invention are also useful for preventing or reversing the symptoms, disorders or diseases induced by the binding of these integrins to their respective ligands.

For example, International Publication No. WO 98/53817, published Dec. 3, 1998 (the disclosure of which is incorporated herein by reference in its entirety) and references cited therein describe disorders mediated by $\alpha_4\beta_7$. This reference also describes an assay for determining antagonism of $\alpha_4\beta_7$ dependent binding to VCAM-Ig fusion protein.

Additionally, compounds that bind $\alpha_d\beta_2$ and $\alpha_e\beta_7$ integrins are particularly useful for the treatment of asthma and related lung diseases. See, for example, M. H. Grayson et al., *J. Exp. Med.* 1998, 188(11) 2187-2191. Compounds that bind $\alpha_e\beta_7$ integrin are also useful for the treatment of systemic lupus erythematosus (see, for example, M. Pang et al., *Arthritis Rheum.* 1998, 41(8), 1456-1463); Crohn's disease, ulcerative colitis and infammatory bowel disease (IBD) (see, for example, D. Elewaut et al., *Scand J. Gastroenterol* 1998, 33(7) 743-748); Sjogren's syndrome (see, for example, U. Kroneld et al., *Scand J. Gastroenterol* 1998, 27(3), 215-218); and rheumatoid arthritis (see, for example, *Scand J. Gastroenterol* 1996, 44(3), 293-298). And compounds that bind $\alpha_6\beta_1$ may be useful in preventing fertilization (see, for example, H. Chen et al., *Chem. Biol.* 1999, 6, 1-10).

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| aq or aq. = | aqueous |
| AcOH = | acetic acid |
| bd = | broad doublet |
| bm = | broad multiplet |
| bs = | broad singlet |
| Bn = | benzyl |
| Boc = | N-tert-butoxylcarbonyl |
| $Boc_2O$ = | di-tert-butyl dicarbonate |
| BOP = | benzotriazol-1-yloxy-tris(dimethylamino)phosphonium hexafluorophosphate |
| Cbz = | carbobenzyloxy |
| $CHCl_3$ = | chloroform |
| $CH_2Cl_2$ = | dichloromethane |
| $(COCl)_2$ = | oxalyl chloride |
| d = | doublet |
| dd = | doublet of doublets |
| dt = | doublet of triplets |
| DBU = | 1,8-diazabicyclo[5.4.0]undec-7-ene |
| DCC = | 1,3-dicyclohexylcarbodiimide |
| DMAP = | 4-N,N-dimethylaminopyridine |
| DME = | ethylene glycol dimethyl ether |
| DMF = | N,N-dimethylformamide |
| DMSO = | dimethylsulfoxide |
| EDC = | 1-(3-dimethylaminopropyl)-3-ethylcarbodiimide hydrochloride |
| $Et_3N$ = | triethylamine |
| $Et_2O$ = | diethyl ether |
| EtOAc = | ethyl acetate |
| EtOH = | ethanol |
| eq or eq. = | equivalent |
| Fmoc = | N-(9-fluorenylmethoxycarbonyl) |
| FmocONSu = | N-(9-fluorenylmethoxycarbonyl)-succinimide |
| g = | grams |
| h = | hour |

-continued

| | |
|---|---|
| $H_2O$ = | water |
| HBr = | hydrobromic acid |
| HCl = | hydrochloric acid |
| HOBT = | 1-hydroxybenzotriazole hydrate |
| hr = | hour |
| $K_2CO_3$ = | potassium carbonate |
| L = | liter |
| m = | multiplet |
| MeOH = | methanol |
| mg = | milligram |
| $MgSO_4$ = | magnesium sulfate |
| mL = | milliliter |
| mm = | millimeter |
| mM = | millimolar |
| mmol = | millimol |
| mp = | melting point |
| N = | normal |
| NaCl = | sodium chloride |
| $Na_2CO_3$ = | sodium carbonate |
| $NaHCO_3$ = | sodium bicarbonate |
| NaOEt = | sodium ethoxide |
| NaOH = | sodium hydroxide |
| $NH_4Cl$ = | ammonium chloride |
| NMM = | N-methylmorpholine |
| Phe = | L-phenylalanine |
| Pro = | L-proline |
| psi = | pounds per square inch |
| $PtO_2$ = | platinum oxide |
| q = | quartet |
| quint. = | quintet |
| rt = | room temperature |
| s = | singlet |
| sat = | saturated |
| t = | triplet |
| t-BuOH = | tert-butanol |
| TFA = | trifluoroacetic acid |
| THF = | tetrahydrofuran |
| TLC or tlc = | thin layer chromatography |
| Ts = | tosyl |
| TsCl = | tosyl chloride |
| TsOH = | tosylate |
| μL = | microliter |

The following Methods may be used to prepare the compounds of this invention.

Method A

Methyl Ester Preparation Procedure

Amino acid methyl esters can be prepared using the method of Brenner and Huber *Helv. Chim. Acta* 1953, 36, 1109.

Method B

BOP Coupling Procedure

The desired dipeptide ester was prepared by the reaction of a carboxylic acid (1 equivalent) with the appropriate amino acid ester or amino acid ester hydrochloride (1 equivalent), benzotriazol-1-yloxy-tris(dimethylamino)-phosphonium hexafluorophosphate [BOP] (2.0 equivalent), triethylamine (1.1 equivalent), and DMF. The reaction mixture was stirred at room temperature overnight. The crude product is purified flash chromatography to afford the dipeptide ester.

Method C

Hydrogenation Procedure I

Hydrogenation was performed using 10% palladium on carbon (10% by weight) in methanol at 30 psi overnight. The mixture was filtered through a pad of Celite and the filtrate concentrated to yield the desired compound.

Method D

Hydrolysis Procedure I

To a chilled (0° C.) THF/$H_2O$ solution (2:1, 5-10 mL) of the appropriate ester was added LiOH (or NaOH) (0.95 equivalents). The temperature was maintained at 0° C. and the reaction was complete in 1-3 hours. The reaction mixture was extracted with ethyl acetate and the aqueous phase was lyophilized resulting in the desired carboxylate salt.

Method E

Ester Hydrolysis Procedure II

To a chilled (0° C.) THF/$H_2O$ solution (2:1, 5-10 mL) of the appropriate ester was added LiOH (1.1 equivalents). The temperature was maintained at 0° C. and the reaction was complete in 1-3 hours. The reaction mixture was concentrated and the residue was taken up into $H_2O$ and the pH adjusted to 2-3 with aqueous HCl. The product was extracted with ethyl acetate and the combined organic phase was washed with brine, dried over $MgSO_4$, filtered and concentrated to yield the desired acid.

Method F

Ester Hydrolysis Procedure III

The appropriate ester was dissolved in dioxane/$H_2O$ (1:1) and 0.9 equivalents of 0.5 N NaOH was added. The reaction was stirred for 3-16 hours and then concentrated. The resulting residue was dissolved in $H_2O$ and extracted with ethyl acetate. The aqueous phase was lyophilized to yield the desired carboxylate sodium salt.

Method G

BOC Removal Procedure

Anhydrous hydrochloride (HCl) gas was bubbled through a methanolic solution of the appropriate Boc-amino acid ester at 0° C. for 15 minutes and the reaction mixture was stirred for three hours. The solution was concentrated to a syrup and dissolved in $Et_2O$ and reconcentrated. This procedure was repeated and the resulting solid was placed under high vacuum overnight.

Method H tert-Butyl Ester Hydrolysis Procedure I

The tert-butyl ester was dissolved in $CH_2Cl_2$ and treated with TFA. The reaction was complete in 1-3 hr at which time the reaction mixture was concentrated and the residue dissolved in $H_2O$ and lyophilized to yield the desired acid.

Method I

EDC Coupling Procedure I

To a $CH_2Cl_2$ solution (5-20 mL) of a carboxylic acid (1 equivalent), the appropriate amino acid ester hydrochloride (1 equivalent), N-methylmorpholine (1.1-2.2 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was poured into $H_2O$ and the organic phase was washed with sat. $NaHCO_3$, brine, dried ($MgSO_4$ or $Na_2SO_4$), filtered and concentrated. The crude product was purified by column chromatography.

Method J

EDC Coupling Procedure II

To a DMF solution (5-20 mL) of a carboxylic acid (1 equivalent), the appropriated amino acid ester hydrochloride (1 equivalent), $Et_3N$ (1.1 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was partitioned between EtOAc and $H_2O$ and the organic phase washed with 0.2 N citric acid, $H_2O$, sat. $NaHCO_3$, brine, dried ($MgSO_4$ or $Na_2SO_4$), filtered and concentrated. The crude product was purified by column chromatography or preparative TLC.

Method K tert-Butyl Ester Hydrolysis Procedure II

The tert-butyl ester was dissolved in $CH_2Cl_2$ (5 mL) and treated with TFA (5 mL). The reaction was complete in 1-3 hours at which time the reaction mixture was concentrated and the residue dissolved in $H_2O$ and concentrated. The residue was redissolved in $H_2O$ and lyophilized to yield the desired product.

Method L

Carbamate Formation Procedure I

Into a reaction vial were combined 15.2 mmol, 1.0 eq of the starting hydroxy compound (typically a tyrosine derivative) and 1.86 g (15.2 mmol, 1.0 eq) DMAP. Methylene chloride (50 mL), triethylamine (2.12 mL, 1.54 g, 15.2 mmol, 1.0 eq), and dimethylcarbamyl chloride (1.68 mL, 1.96 g, 18.2 mmol, 1.2 eq) were then added. The vial was capped tightly, and the reaction solution swirled to obtain a homogeneous solution. The reaction solution was then heated to 40° C. After 48 h, TLC of the resulting colorless solution indicated complete conversion. The work-up of the reaction solution was as follows: 50 mL EtOAc and 50 mL hexanes was added to the reaction mixture, and the resulting mixture was washed with 0.5 M citric acid (3×50 mL), water (2×50 mL), 10% $K_2CO_3$ (2×50 mL), and sat. NaCl (1×50 mL); dried with $MgSO_4$, filtered and evaporated to afford the desired compound.

Method M

Carbamate Formation Procedure II

Into a reaction vial were combined 84.34 mmol (1.0 eq) of the starting hydroxy compound (typically a tyrosine derivative) and 17.0 g (84.34 mmol, 1.0 eq) 4-nitrophenyl chloroformate. Methylene chloride (700 mL) was added and the vial was capped with a septum. A nitrogen line was attached and the vial was immersed in a 4:1 water/ethanol dry ice slurry with stirring to cool to −15° C. Triethylamine (29.38 mL, 21.33 g, 210.81 mmol, 2.5 eq) was added over five minutes with stirring and the stirring was continued at −10 to −15° C. for 1 h. N-Methyl piperazine (9.35 mL, 8.45 g, 84.34 mmol, 1.0 eq) was added over three minutes with stirring and stirring was continued overnight while warming to room temperature. The reaction mixture was diluted with 700 mL hexanes' and the resulting mixture was washed repeatedly with 10% $K_2CO_3$, until no yellow color (from 4-nitrophenol) is observed in the aqueous layer. The mixture was then washed with sat. NaCl, dried over anhydrous $MgSO_4$, filtered and evaporated. The residue was dissolved in 500 mL of ethanol and evaporated to remove triethylamine. The residue was again dissolved in 500 mL of ethanol and evaporated to remove triethylamine. The residue was then dissolved in 400 mL of ethanol and 600 mL of water was added with stirring to precipitate a solid or oil. If an oil if formed, the oil is stirred vigorously to induce it to solidify. The solid is then isolated by filtration. Dissolution, precipitation, and filtration are repeated once and the resulting solid is rinsed with water to remove traces of yellow color. The solid is then subjected to high vacuum until the mass remains constant thereby affording the desired carbamyloxy compound.

Method N

Purification Method

Unless otherwise stated, the compounds of this method were purified by LC/MS using 10% to 90% acetonitrile/water gradient with 0.1% trifluoroacetic acid (12 min. run time).

Method O

Analytical Method

Unless otherwise stated, the compounds of this method were analyzed by LC/MS using 10% to 90% acetonitrile/water gradient with 0.1% trifluoroacetic acid (5.5 min run time).

Example 1

Synthesis of N-{6-[N-(benzyl)-N-(1-phenylethyl)amino]-4-chloro-1,3,5-triazin-2-yl}-L-4-(N,N-dimethylcarbamyloxy)phenylalanine

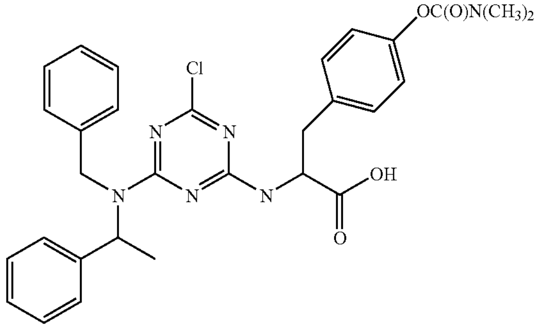

Step A

Cyanuric chloride (0.045 mmol), t-butyl tyrosine O—(N,N-dimethyl)carbamate (0.0545 mmol), and diisopropylethylamine (0.18 mmol) were dissolved in tetrahydrofuran (4.0 mL) and shaken at room temperature. After two hours, the solvent was removed under reduced pressure providing N-(4,6-dichloro-1,3,5-triazin-2-yl)-L-4-(N,N-dimethylcarbamyloxy)-phenylalanine tert-butyl ester without purification. (m/e 456).

Step B

N-(4,6-Dichloro-1,3,5-triazin-2-yl)-L-4-(N,N-dimethylcarbamyloxy)-phenylalanine tert-butyl ester (0.045 mmol), N-benzyl-N-phenethylamine (0.045 mmol) and diisopropylethylamine (0.18 mmol) were dissolved in THF and heated to 60° C. overnight. The solvent was removed under reduced pressure providing N-{6-[N-(benzyl)-N-(1-phenylethyl)amino]-4-chloro-1,3,5-triazin-2-yl}-L-4-(N,N-dimethylcarbamyloxy)phenylalanine tert-butyl ester, which was used without purification. (m/e 631)

Step 3

The N-{6-[N-(benzyl)-N-(1-phenylethyl)amino]-4-chloro-1,3,5-triazin-2-yl}-L-4-(N,N-dimethylcarbamyloxy)phenylalanine tert-butyl ester (0.022 mmol) was dissolved in a 1/1 solution of TFA/$CH_2Cl_2$ (1.0 mL) and shaken for 1 hour. The solvent was removed and the crude product was dissolved in a 1/1 solution of DMSO/$CH_3CN$ and purified by preparative LC/MS described above providing N-{6-[N-(benzyl)-N-(1-phenylethyl)amino]-4-chloro-1,3,5-triazin-2-yl}-L-4-(N,N-dimethylcarbamyloxy)phenylalanine. (m/e 575)

Example 2

Synthesis of N-{4-[N-(Benzyl)-N-(1-phenylethyl)amino]-1,3,5-triazin-2-yl}-L-4-(N,N-dimethylcarbamyloxy)phenylalanine

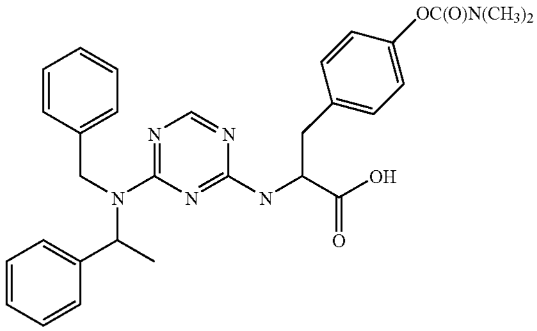

N-{6-[N-(Benzyl)-N-(1-phenylethyl)amino]-4-chloro-1,3,5-triazin-2-yl}-L-4-(N,N-dimethylcarbamyloxy)phenylalanine tert-butyl ester (0.022 mmol) was dissolved in methanol. Sodium Bicarbonate (0.18 mmol), 10% Pd/C (0.0022 mmol) was added. The reaction mixture was degassed twice and purged with $H_2$ twice. The suspension was stirred under $H_2$ for 4 hours, filtered through celite and the solvent removed. The resulting oil was dissolved in EtOAc and extracted with water (2×0.5 mL). The organic layer was dried over $MgSO_4$, filtered and the solvent removed. The resulting oil was dissolved in a 1/1 solution of TFA/$CH_2Cl$ and shaken for 2 hours, then the solvent was removed. The crude material was dissolved in a 1/1 solution of DMSO/$CH_3CN$ and purified by preparative LC/MS providing N-{4-[N-(benzyl)-N-

(1-phenylethyl)amino]-1,3,5-triazin-2-yl}-L-4-(N,N-dimethylcarbamyloxy)-phenylalanine. (m/e 541).

Example 3

Synthesis of N-{4-Chloro-6-[N-(methyl)-N-(p-toluenesulfonyl)amino]-1,3,5-triazin-2-yl}-L-4-(N,N-dimethylcarbamyloxy)phenylalanine

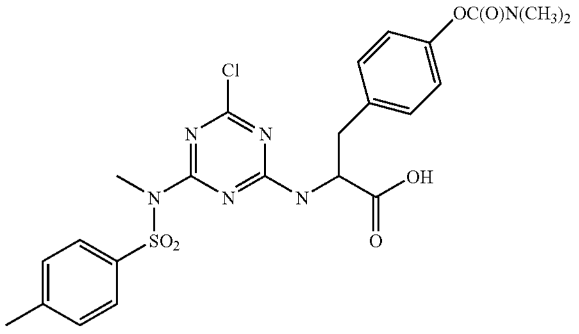

Step 1

N-Methyl-p-toluenesulfonamide (0.98 mmol) was added to a solution of N-(4,6-dichloro-1,3,5-triazin-2-yl)-L-4-(N,N-dimethylcarbamyloxy)-phenylalanine tert-butyl ester (0.89 mmol) in THF (50 mL) and stirred for 5 min. Cesium carbonate (2.7 mmol) was added and the mixture was heated at 60° C. overnight. The solid was filtered and the solvent removed under reduced pressure. The crude product N-{4-chloro-6-[N-(methyl)-N-(p-toluenesulfonyl)amino]-1,3,5-triazin-2-yl}-L-4-(N,N-dimethylcarbamyloxy)-phenylalanine tert-butyl ester was used without purification. (m/e 605)

Step 2

N-{4-Chloro-6-[N-(methyl)-N-(p-toluenesulfonyl)amino]-1,3,5-triazin-2-yl}-L-4-(N,N-dimethylcarbamyloxy)-phenylalanine tert-butyl ester (0.017 mmol) was dissolved in a 1/1 solution of $TFA/CH_2Cl_2$ and shaken for 2 hours, then the solvent was removed. The crude material was dissolved in a 1/1 solution of $DMSO/CH_3CN$ and purified by preparative LC/MS providing N-{4-chloro-6-[N-(methyl)-N-(p-toluenesulfonyl)amino]-1,3,5-triazin-2-yl}-L-4-(N,N-dimethylcarbamyloxy)phenylalanine. (m/e 549)

Example 4

Synthesis of N-{4-Chloro-6-(N,N-dihexylamino)-1,3,5-triazin-2-yl}phenylalanine ethyl ester

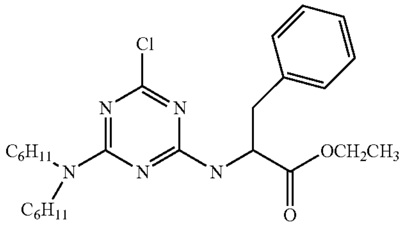

Step 1

Dihexylamine (6.3 mL, 27 mmol) was added to a mixture of cyanuric chloride (5.0 g, 27 mmol) and sodium carbonate (2.9 g, 27 mmol) in acetonitrile (50 mL). The reaction mixture was heated to reflux for 16 h and then allowed to col to ambient temperature. The mixture was diluted with ethyl acetate and water. The phases were separated and the organic phase was washed with brine, dried over magnesium sulfate, and concentrated under reduced pressure. The crude material was purified by flash column chromatography through silica gel (elution with 3:1 hexanes:chloroform) to afford 2,4-dichloro-6-dihexylamino-1,3,5-triazine.

Step 2

L-phenylalanine ethyl ester hydrochloride (1.0 g, 4.4 mmol) was added to a mixture of 2,4-dichloro-6-dihexylamino-1,3,5-triazine (1.5 g, 4.5 mmol) and sodium carbonate (0.92 g, 8.7 mmol) in acetonitrile (40 mL). The reaction mixture was heated to reflux for 16 h and then allowed to col to ambient temperature. The mixture was diluted with ethyl acetate and water. The phases were separated and the organic phase was washed with brine, dried over magnesium sulfate, and concentrated under reduced pressure. The crude material was purified by flash column chromatography through silica gel (elution with chloroform) to afford N-{4-chloro-6-(N,N-dihexylamino)-1,3,5-triazin-2-yl}phenylalanine ethyl ester. Anal. Calcd. for $C_{26}H_{40}ClN_5O_2$: C, 63.72; H, 8.23; N 14.29. Found: C, 63.67; H, 8.06; N, 14.24.

Example 5

Synthesis of N-(4-(N,N-Di-n-hexylamino)-1,1-dioxo-1,2,5-thiadiazol-3-yl)-L-tyrosine

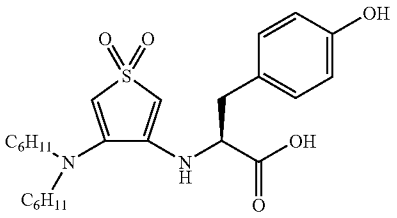

Step 1

3,4-Diethyloxy-1-oxo-1,2,5-thiadiazole and 3,4-Diethyloxy-1,1-dioxo-1,2,5-thiadiazole were prepared according to the procedures described in R. Y. Wen et al, *J Org Chem.*, (1975) 40, 2743; and R. Y. Wen et al, *Org Prep Proceed.*, (1969) 1, 255.

Step 2

Dihexylamine (90 mg, 0.48 mmol) was added to a solution of 3,4-diethyloxy-1,1-dioxo-1,2,5-thiadiazole (100 mg, 0.48 mmol) in ethanol (5 mL) and the reaction stirred overnight at room temperature. The solvent was removed under reduced pressure and the residue absorbed onto silica gel, and purified by flash column chromatography (silica, hexane:EtOAc 3:1) to yield 4-(N,N-di-n-hexylamino)-3-ethoxy-1,1-dioxo-1,2,5-thiadiazole (120 mg, 72%). MS (EI, m/e 345).

Step 3

A solution of 4-(N,N-di-n-hexylamino)-3-ethoxy-1,1-dioxo-1,2,5-thiadiazole (400 mg, 1.02 mmol) and L-tyrosine t-butyl ester (261 mg, 1.1 mmol) in EtOH (10 mL) was stirred at room temperature for 36 hrs. The solvent was removed under reduced pressure residue purified by flash column chromatography (silica, hexane:EtOAc 3:1 then 1:1) to give N-(4-(N,N-di-n-hexylamino)-1,1-dioxo-1,2,5-thiadiazol-3-yl)-L-tyrosine tert-butyl ester as a white waxy solid (400 mg, 73%). Anal. Calc'd for $C_{27}H_{44}N_4O_5S.0.55EtOAc$: C, 59.93; H, 8.34; N, 9.57. Found: C, 59.84; H, 8.44; N, 9.62.

Step 4

N-(4-(N,N-Di-n-hexylamino)-1,1-dioxo-1,2,5-thiadiazol-3-yl)-L-tyrosine tert-butyl ester (100 mg, 0.19 mmol) was dissolved in formic acid and the mixture stirred at room temperature for 36 hrs. Excess formic acid was removed under reduced pressure to yield N-(4-(N,N-Di-n-hexylamino)-1,1-dioxo-1,2,5-thiadiazol-3-yl)-L-tyrosine as a white solid (90 mg, 98%). Anal. Calc'd for $C_{23}H_{36}N_4O_5S$: C, 57.48; H, 7.55; N, 11.66. Found: C, 57.04; H, 7.23; N, 11.38.

Example 6

Synthesis of N-(4-(N,N-Di-n-hexylamino)-1,1-dioxo-1,2,5-thiadiazol-3-yl)-L-4-(N,N-dimethylcarbamyloxy)phenylalanine

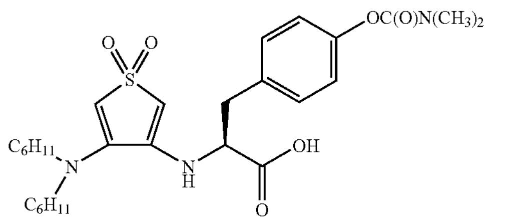

Step 1

N-(4-(N,N-Di-n-hexylamino)-1,1-dioxo-1,2,5-thiadiazol-3-yl)-L-tyrosine tert-butyl ester (180 mg, 0.34 mmoL) was dissolved in pyridine (5 ml). Dimethylcarbamoyl chloride (108 mg, 1 mmol) was added dropwise and the mixture stirred at room temperature overnight. Pyridine was removed under high vacuum (low water bath temperature), the residue absorbed onto silica gel and purified by flash column chromatography (silica, hexane:EtOAc 2:1) to yield N-(4-(N,N-di-n-hexylamino)-1,1-dioxo-1,2,5-thiadiazol-3-yl)-L-4-(N,N-dimethylcarbamyloxy)phenylalanine tert-butyl ester (140 mg, 68%).

Step 2

N-(4-(N,N-Di-n-hexylamino)-1,1-dioxo-1,2,5-thiadiazol-3-yl)-L-4-(N,N-dimethylcarbamyloxy)-phenylalanine tert-butyl ester (140 mg, 0.23 mmol) was dissolved in formic acid and the mixture stirred at room temperature overnight. Excess formic acid was removed under reduced pressure to yield N-(4-(N,N-di-n-hexylamino)-1,1-dioxo-1,2,5-thiadiazol-3-yl)-L-4-(N,N-dimethylcarbamyloxy)phenylalanine as a white solid (110 mg, 87%). Anal. Calc'd for $C_{26}H_{41}N_5O_6S$: C, 56.6; H, 7.49; N, 12.69. Found: C, 56.67; H, 7.4; N, 12.46.

Example 7

Synthesis of N-(4-(N,N-Di-n-hexylamino)-1,1-dioxo-1,2,5-thiadiazol-3-yl)-L-4-(4-methylpiperazin-1-ylcarbonyloxy)phenylalanine

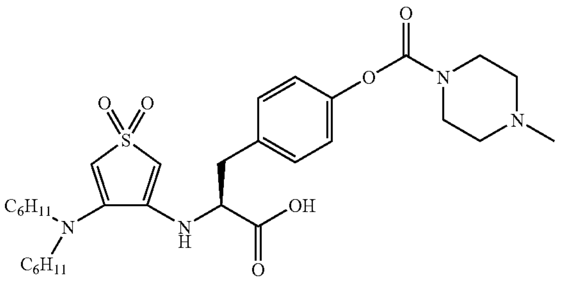

Step 1

A solution of N-(4-(N,N-di-n-hexylamino)-1,1-dioxo-1,2,5-thiadiazol-3-yl)-L-tyrosine tert-butyl ester (500 mg, 0.93 mmol), and p-nitrophenyl chloroformate (179 mg, 0.89 mmol) in dichloromethane (20 mL) was cooled to 0° C. under an argon atmosphere. Triethylamine (235 mg, 2.32 mmol) was added dropwise and the mixture stirred at 0° C. for 30 mins, then allowed to warm to room temperature for a further 40 mins. The mixture was re-cooled to 0° C. and N-methylpiperazine (90 mg, 0.89 mmol) added. The mixture was allowed to warm to room temperature and stirred for three hours. The mixture was diluted with diethyl ether (150 mL) and the organic solution washed with 10% potassium carbonate solution until no further yellow color was produced in the aqueous phase. The organic layer was separated, dried ($MgSO_4$) and the solvent removed under reduced pressure. The residue was purified by flash column chromatography (silica, EtOAc:MeOH:$Et_3N$ 94:5:1) to give N-(4-(N,N-di-n-hexylamino)-1,1-dioxo-1,2,5-thiadiazol-3-yl)-L-4-(4-methylpiperazin-1-ylcarbonyloxy)phenylalanine tert-butyl ester as a pale yellow foam (310 mg, 50%). Anal. Calc'd for $C_{33}H_{54}N_6O_6S$: C, 59.79; H, 8.21; N, 12.68. Found: C, 59.47; H, 8.25; N, 12.49

Step 2

N-(4-(N,N-Di-n-hexylamino)-1,1-dioxo-1,2,5-thiadiazol-3-yl)-L-4-(4-methylpiperazin-1-ylcarbonyloxy)phenylalanine tert-butyl ester (200 mg, 0.3 mmol) was dissolved in formic acid (5 mL) and the mixture stirred at room temperature for 48 hrs. Excess formic acid was removed under reduced pressure and the residue recrystallized from EtOAc/MeOH to yield N-(4-(N,N-di-n-hexylamino)-1,1-dioxo-1,2,5-thiadiazol-3-yl)-L-4-(4-methylpiperazin-1-ylcarbonyloxy)phenylalanine as an off-white solid (120 mg, 67%). Anal. Calc'd for $C_{29}H_{46}N_6O_6S.0.75H_2O$: C, 56.15; H, 7.72; N, 13.55. Found: C, 56.1; H, 7.44; N, 13.46.

Example 8

Synthesis of N-[4-(2-(3-Methylphenylaminocarbonylamino)eth-1-lamino)-1,1-dioxo-1,2,5-thiadiazol-3-yl]-L-4-(N,N-dimethylcarbamyloxy)phenylalanine

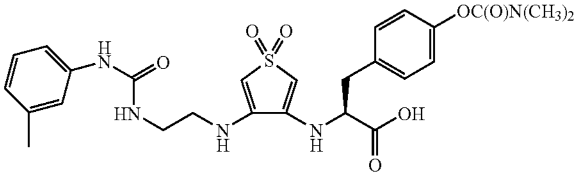

Step 1

A solution of 3,4-diethyloxy-1,1-dioxo-1,2,5-thiadiazole (400 mg, 1.94 mmol) and L-tyrosine t-butyl ester (1.25 g, 5.2 mmol) in ethanol (25 mL) was stirred at room temperature overnight. Solvent was removed under reduced pressure and the product N-(4-ethoxy-1,1-dioxo-1,2,5-thiadiazol-3-yl)-L-tyrosine tert-butyl ester was used in further transformations without further purification (790 mg).

Step 2

N-Boc-Ethylene diamine (800 mg, 5 mmol) and m-tolyl isocyanate (665 mg, 5 mmol) were dissolved in acetonitrile and the mixture stirred at room temperature for 4 hrs. Solvent was removed under reduced pressure and the residue absorbed onto silica gel; prior to purification by flash column chromatography (silica, hexane:EtOAc 1:1) to yield the desired compound as a white solid (300 mg, 21%) (MS (+ESI, m/e) 294 $(M+H)^+$). The N-Boc protected compound (300 mg, 1.02 mmol) was dissolved in formic acid (10 ml) and the mixture stirred at room temperature overnight. Excess acid was removed to yield the formate salt of 2-(3-methylphenylaminocarbonylamino)-eth-1-ylamine as a white foam (210 mg).

Step 3

To a solution of N-(4-ethoxy-1,1-dioxo-1,2,5-thiadiazol-3-yl)-L-tyrosine tert-butyl ester from Step A (150 mg, 0.38 mmol) and the formate salt of 2-(3-methylphenylaminocarbonylamino)eth-1-ylamine from Step B (210 mg, 0.89 mmol) in ethanol (10 mL) was added triethylamine (133 mg, 1.44 mmol). The reaction was stirred at room temperature overnight. Solvent was removed under reduced pressure and the residue purified by flash column chromatography (silica, 5% MeOH in EtOAc) to give N-[4-(2-(3-methylphenylamino-carbonylamino)eth-1-ylamino)-1,1-dioxo-1,2,5-thiadiazol-3-yl]-L-tyrosine tert-butyl ester (130 mg, 91%). MS (+ESI, m/e) 545 $(M+H)^+$.

Step 4

N-[4-(2-(3-Methylphenylamino-carbonylamino)eth-1-ylamino)-1,1-dioxo-1,2,5-thiadiazol-3-yl]-L-tyrosine tert-butyl ester (130 mg, 0.24 mmol) was dissolved in pyridine (5 mL). Dimethylcarbamoyl chloride (77 mg, 0.72 mmol) was added dropwise and the mixture heated at 50° C. under an argon atmosphere overnight. Pyridine was removed under reduced pressure, the residue absorbed onto silica gel and purified by flash column chromatography (silica, hexane: EtOAc 1:2, then 5% MeOH in EtOAc) to yield N-[4-(2-(3-methylphenylamino-carbonylamino)eth-1-ylamino)-1,1-dioxo-1,2,5-thiadiazol-3-yl]-L-4-(N,N-dimethylcarbamyloxy) phenylalanine tert-butyl ester (140 mg, 93%). MS (+ESI, m/e) 616 $(M+H)^+$.

Step 5

N-[4-(2-(3-Methylphenylamino-carbonylamino)eth-1-ylamino)-1,1-dioxo-1,2,5-thiadiazol-3-yl]-L-4-(N,N-dimethylcarbamyloxy)phenylalanine tert-butyl ester (120 mg, 0.19 mmol) was dissolved in formic acid (10 mL) and the mixture stirred at room temperature for 36 hrs. Excess acid was removed to yield N-[4-(2-(3-methylphenylamino-carbonylamino)eth-1-ylamino)-1,1-dioxo-1,2,5-thiadiazol-3-yl]-L-4-(N,N-dimethylcarbamyloxy)phenylalanine as a pale yellow foam (100 mg, 93%). MS (+ESI, m/e) 560 $(M+H)^+$.

Example 9

Synthesis of N-(4-(N,N-Dimethylamino)-1-oxo-1,2,5-thiadiazol-3-yl)-L-4-(N,N-dimethylcarbamyloxy) phenylalanine tert-Butyl Ester

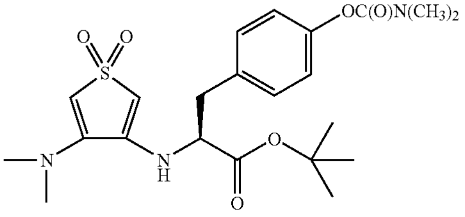

Step 1

A solution of 3,4-diethoxy-1-oxo-1,2,5-thiadiazole (1 g, 0.52 mmol) and L-tyrosine t-butyl ester (1.25 g, 0.52 mmol) in ethanol (25 mL) was stirred at room temperature for 60 hr. Solvent was removed under reduced pressure and the residue purified by flash column chromatography (silica, hexane: EtOAc 1:1 to give N-(4-ethoxy-1-oxo-1,2,5-thiadiazol-3'-yl)-L-tyrosine tert-butyl ester (1.75 g, 88%). MS (+ESI, m/e) 382 $(M+H)^+$.

Step 2

N-(4-Ethoxy-1-oxo-1,2,5-thiadiazol-3-yl)-L-tyrosine tert-butyl ester (400 mg, 1.05 mmol) was dissolved in pyridine (10 mL) and dimethylcarbamoyl chloride (338 mg, 3.15 mmol) was added. The reaction was stirred at room temperature under an inert atmosphere overnight. TLC indicated large amounts of unreacted starting material so the mixture was heated at 50° C. for a further 48 hrs. Excess pyridine was removed under reduced pressure and the residue purified by flash column chromatography (silica, hexane: EtOAc 1:1 to give N-(4-ethoxy-1-oxo-1,2,5-thiadiazol-3-yl)-L-4-(N,N-dimethylcarbamyloxy)-phenylalanine tert-butyl ester (280 mg, 59%). MS (+ESI, m/e) 453 (M+H).

Step 3

A 2M solution of dimethylamine in THF (5 mL, 10 mmol) was added to a solution of the compound from Step B (180 mg, 0.35 mmol) in ethanol (10 mL). The reaction was stirred at room temperature overnight and solvent removed under reduced pressure. Residue was purified by flash column chromatography (silica, EtOAc:MeOH:$Et_3N$ 90:10:1) to give N-(4-(N,N-dimethylamino)-1-oxo-1,2,5-thiadiazol-3-yl)-L-4-(N,N-dimethylcarbamyloxy)phenylalanine tert-butyl ester as a white foam (140 mg, 88%). Anal. Calc'd for $C_{22}H_{29}N_5O_5S$: C, 53.2; H, 6.47; N, 15.51. Found: C, 52.94; H, 6.18; N, 15.34.

Example 10

N-[1-Toluene-4-sulfonyl)piperidin-4-yl]-L-phenylalanine

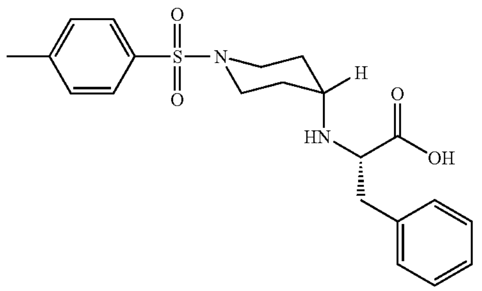

Step 1

To a solution of 1-[(4-methylphenyl)sulfonyl]-4-piperidone (1.0 g, 3.95 mmol) and L-phenylalanine methyl ester (0.64 g, 3.58 mmol) in methylene chloride (20 mL) was added acetic acid (0.62 mL, 10.78 mmol) followed by sodium triacetoxyborohydride (1.9 g, 8.96 mmol). After 24 h, the solvent was removed and the residue was taken up in ethyl acetate (50 mL), washed with saturated sodium bicarbonate solution, saturated brine, dried over potassium carbonate and evaporated to an amber oil which was purified by flash chromatography (eluting with 98:1 methylene chloride/methanol) to give N-[1-toluene-4-sulfonyl)piperidin-4-yl]-L-phenylalanine methyl ester.

Step 2

To a solution of N-[1-toluene-4-sulfonyl)piperidin-4-yl]-L-phenyl-alanine methyl ester (0.2 g, 0.48 mmol) in THF (1 mL) was added 1N LiOH solution (0.46 mL, 0.46 mmol). After 24 h, the reaction mixture was diluted with water (50 mL), extracted with diethyl ether and lyophilized to afford N-[1-Toluene-4-sulfonyl)piperidin-4-yl]-L-phenylalanine as the lithium salt. Anal. Calc'd for $C_{21}N_{26}N_2O_4SLi$. $5H_2O$: C, 57.79; H, 6.70; N, 6.42. Found: C, 57.7; H, 6.30; N, 6.23.

Example 11

General Library Synthesis

A solution of N-(4,6-dichloro-1,3,5-triazin-2-yl)-L-4-(N,N-dimethylcarbamyloxy)-phenylalanine tert-butyl ester (0.018 mmol) in THF (1.0 mL) was added to a solution of methylphenethylamine (0.018 mmol), DIEA (0.036 mmol) in THF (1.0 mL) and shaken at 60° C. overnight. The solvent was removed and the resulting oil was dissolved in DMF (0.5 mL). To this solution was added a solution of isobutylamine (0.0213 mmol) and DIEA (0.071 mmol) in DMF (0.5 mL). The resulting mixture was shaken at 110° C. for 16 hrs. The solvent was removed under reduced pressure. The oil was dissolved in a 1/1 solution of $TFA/CH_2Cl_2$ and shaken for 2 hours, then the solvent was removed. The crude material was dissolved in a 1/1 solution of $DMSO/CH_3CN$ and purified by preparative LC/MS (preparative method 2) and analyzed by LC/MS (analytical method 2) unless otherwise noted.

Using the appropriate starting materials and reagents, the following additional compounds were prepared:

N-(3-nitrothiophen-2-yl)-L-4-(N,N-dimethylcarbamyloxy)-phenylalanine;

N-[1-phenyltetrazol-5-yl]-L-4-(N,N-dimethylcarbamyloxy)-phenylalanine;

N-[1,3-dimethyl-4-nitropyrazol-5-yl]-L-4-(N,N-dimethylcarbamyl-oxy)phenylalanine;

N-[1-ethylpyrazol-5-yl]-L-4-(N,N-dimethylcarbamyloxy)-phenylalanine;

N-(4-phenylsulfonylthiophen-3-yl)-L-4-(N,N-dimethylcarbamyloxy)-phenylalanine;

N-(1,4-diphenyl-1,2,3-triazol-5-yl)-L-4-(N,N-dimethylcarbamyloxy)-phenylalanine;

N-(1-phenylimidazol-2-yl)-L-4-(N,N-dimethylcarbamyloxy)-phenylalanine;

N-(6-bromopyridin-2-yl)-L-4-(N,N-dimethylcarbamyloxy)-phenylalanine;

N-[6-(naphth-1-yl)pyridin-2-yl]-L-4-(N,N-dimethylcarbamyloxy)-phenylalanine;

N-{3-[N-methyl-N-(4-methylphenylsulfonyl)amino]pyridin-2-yl}-L-4-(N,N-dimethylcarbamyloxy)phenylalanine;

N-{3-[N-methyl-N-(4-methylphenylsulfonyl)amino]pyridin-4-yl}-L-4-(N,N-dimethylcarbamyloxy)phenylalanine;

N-(5-trifluoropyridin-2-yl)-L-4-(N,N-dimethylcarbamyloxy)-phenylalanine;

N-{5-[[5-phenylcarbonylmethylthio-4-(3-trifluoromethylphenyl)]-1,2,4-triazol-3-yl]pyridin-2-yl}-L-4-(N,N-dimethylcarbamyloxy)-phenylalanine;

N-(4-methyl-3-nitropyridin-2-yl)-L-4-(N,N-dimethylcarbamyloxy)-phenylalanine;

N-(3,5-dinitropyridin-2-yl)-L-4-(N,N-dimethylcarbamyloxy)-phenylalanine;

N-{3-[N-methyl-N-(4-methylphenylsulfonyl)amino]pyridin-4-yl}-L-phenylalanine;

N-[4-(3-methylisoxazol-5-ylamino)-6-(2-methylpropylamino)-1,3,5-triazin-2-yl]-L-4-(N,N-dimethylcarbamyloxy)phenylalanine;

N-[4-(phenylamino)-6-(3-methylisoxazol-5-ylamino)-1,3,5-triazin-2-yl]-L-4-(N,N-dimethylcarbamyloxy)phenylalanine;

N-[4-(benzylamino)-6-(3-methylisoxazol-5-ylamino)-1,3,5-triazin-2-yl]-L-4-(N,N-dimethylcarbamyloxy)phenylalanine;

N-{4-[2-(1-methylpyrrolidin-2-yl)ethylamino]-6-[2-(4-methylphenyl)ethylamino)]-1,3,5-triazin-2-yl}-L-4-(N,N-dimethylcarbamyloxy)phenylalanine;

N-{4-[2-(4-methoxlphenyl)ethylamino)]-6-[2-(1-methylpyrrolidin-2-yl)ethylamino]-1,3,5-triazin-2-yl}-L-4-(N,N-dimethylcarbamyloxy)phenylalanine;

N-{4-[(4-chlorobenzyl)amino)]-6-[2-(1-methylpyrrolidin-2-yl)ethylamino]-1,3,5-triazin-2-yl}-L-4-(N,N-dimethylcarbamyloxy)phenylalanine;

N-{6-[2-(1-methylpyrrolidin-2-yl)ethylamino]-4-[1-(phenyl)ethylamino)]-1,3,5-triazin-2-yl}-L-4-(N,N-dimethylcarbamyloxy)-phenylalanine;

N-[4-(cyclohexylamino)-6-(3-methylisoxazol-5-ylamino)-1,3,5-triazin-2-yl]-L-4-(N,N-dimethylcarbamyloxy)phenylalanine;

N-{4-(2-methylpropylamino)-6-[N-methyl-N-(2-pyridin-2-ylethyl)-amino]-1,3,5-triazin-2-yl}-L-4-(N,N-dimethylcarbamyloxy)-phenylalanine;

N-{4-(2-methylpropylamino)-6-[N,N-bis(2-methoxyethyl)-amino]-1,3,5-triazin-2-yl}-L-4-(N,N-dimethylcarbamyloxy)-phenylalanine;

N-{4-(2-methylpropylamino)-6-[N-methyl-N-(2-phenylethyl)amino]-1,3,5-triazin-2-yl}-L-4-(N,N-dimethylcarbamyloxy)phenylalanine;

N-{4-(benzylamino)-6-[N-methyl-N-(2-(3,4-dimethoxyphenyl)-ethyl)amino]-1,3,5-triazin-2-yl}-L-4-(N,N-dimethylcarbamyloxy)-phenylalanine;

N-{4-(cyclohexylamino)-6-[2-(4-methoxylphenyl)ethylamino]-1,3,5-triazin-2-yl}-L-4-(N,N-dimethylcarbamyloxy)phenylalanine;

N-[4-(2-methoxyethylamino)-6-(3-methylisoxazol-5-ylamino)-1,3,5-triazin-2-yl]-L-4-(N,N-dimethylcarbamyloxy)phenylalanine;

N-[6-(furan-2-ylmethylamino)-4-(2-methoxyethylamino)-1,3,5-triazin-2-yl]-L-4-(N,N-dimethylcarbamyloxy)phenylalanine;

N-[4-(methoxyethylamino)-6-(1-phenylethylamino)-1,3,5-triazin-2-yl]-L-4-(N,N-dimethylcarbamyloxy)phenylalanine;

N-[6-(chlorobenzylamino)-4-(2-methoxyethylamino)-1,3,5-triazin-2-yl]-L-4-(N,N-dimethylcarbamyloxy)phenylalanine;

N-[4-(cyclohexylmethylamino)-6-(3-methylisoxazol-5-ylamino)-1,3,5-triazin-2-yl]-L-4-(N,N-dimethylcarbamyloxy)phenylalanine;

N-{4-(2-methylpropylamino)-6-[2-(4-methoxyphenyl)ethylamino]-1,3,5-triazin-2-yl}-L-4-(N,N-dimethylcarbamyloxy)phenylalanine;

N-[6-(furan-2-ylmethylamino)-4-(2-methylpropylamino)-1,3,5-triazin-2-yl]-L-4-(N,N-dimethylcarbamyloxy)phenylalanine;

N-{4-(2-methylpropylamino)-6-(1-phenylethylamino)-1,3,5-triazin-2-yl}-L-4-(N,N-dimethylcarbamyloxy)phenylalanine;

N-{6-(4-aminosulfonylbenzylamino)-4-(2-methylpropylamino)-1,3,5-triazin-2-yl}-L-4-(N,N-dimethylcarbamyloxy)phenylalanine;

N-{4-(benzylamino)-6-(furan-2-ylmethylamino)-1,3,5-triazin-2-yl}-L-4-(N,N-dimethylcarbamyloxy)phenylalanine;

N-{6-(4-aminosulfonylbenzylamino)-4-(benzylamino)-1,3,5-triazin-2-yl}-L-4-(N,N-dimethylcarbamyloxy)phenylalanine;

N-{4-(4-chlorobenzylamino)-6-[2-(pyrrolidin-1-yl)ethylamino]-1,3,5-triazin-2-yl}-L-4-(N,N-dimethylcarbamyloxy)phenylalanine;

N-{4-[2-(4-methoxyphenyl)ethylamino)]-6-[2-(4-methylphenyl)ethylamino]-1,3,5-triazin-2-yl}-L-4-(N,N-dimethylcarbamyloxy)-phenylalanine;

N-{4-(4-chlorobenzylamino)-6-[2-(4-methylphenyl)ethylamino]-1,3,5-triazin-2-yl}-L-4-(N,N-dimethylcarbamyloxy)phenylalanine;

N-{6-(4-aminosulfonylbenzylamino)-4-[2-(4-methylphenyl)ethylamino]-1,3,5-triazin-2-yl}-L-4-(N,N-dimethylcarbamyloxy)-phenylalanine;

N-{4-(benzylamino)-6-[2-(4-methoxybenzyl)amino)-1,3,5-triazin-2-yl}-L-4-(N,N-dimethylcarbamyloxy)phenylalanine;

N-{4-(benzylamino)-6-(1-phenylethylamino)-1,3,5-triazin-2-yl}-L-4-(N,N-dimethylcarbamyloxy)phenylalanine;

N-{4-(cyclohexylamino)-6-(1-phenylethylamino)-1,3,5-triazin-2-yl}-L-4-(N,N-dimethylcarbamyloxy)phenylalanine;

N-{6-(4-aminosulfonylbenzylamino)-4-(1-cyclhexylethylamino)-1,3,5-triazin-2-yl}-L-4-(N,N-dimethylcarbamyloxy)phenylalanine;

N-{4-[2-(4-methoxyphenyl)ethylamino]-6-(3,4-methylenedioxybenzylamino)-1; 3,5-triazin-2-yl}-L-4-(N,N-dimethylcarbamyloxy)-phenylalanine;

N-{6-(furan-2-ylmethylamino)-4-(3,4-methylenedioxybenzylamino)-1,3,5-triazin-2-yl}-L-4-(N,N-dimethylcarbamyloxy)phenylalanine;

N-{6-(4-chlorobenzylamino)-4-(3,4-methylenedioxybenzylamino)-1,3,5-triazin-2-yl}-L-4-(N,N-dimethylcarbamyloxy)phenylalanine;

N-{6-(4-aminosulfonylbenzylamino)-4-(3,4-methylenedioxybenzylamino)-1,3,5-triazin-2-yl}-L-4-(N,N-dimethylcarbamyloxy)-phenylalanine;

N-{4-(cyclohexylmethylamino)-6-(furan-2-ylmethylamino)-1,3,5-triazin-2-yl}-L-4-(N,N-dimethylcarbamyloxy)phenylalanine;

N-{4-chloro-6-[N-benzyl-N-(2-propyl)amino-1,3,5-triazin-2-yl}-L-4-(N,N-dimethylcarbamyloxy)phenylalanine;

N-{4-chloro-6-[N-(methyl)-N-(2-phenylethyl)amino]-1,3,5-triazin-2-yl}-L-4-(N,N-dimethylcarbamyloxy)phenylalanine;

N-{4-chloro-6-[N-(methyl)-N-(2-(3,4-dimethoxyphenyl)ethyl)amino]-1,3,5-triazin-2-yl}-L-4-(N,N-dimethylcarbamyloxy)phenylalanine;

N-{4-chloro-6-[N-(ethyl)-N-(pyridin-4-ylmethyl)amino]-1,3,5-triazin-2-yl}-L-4-(N,N-dimethylcarbamyloxy)phenylalanine;

N-{4-chloro-6-[N-(benzyl)-N-(1-phenylethyl)amino]-1,3,5-triazin-2-yl}-L-4-(N,N-dimethylcarbamyloxy)phenylalanine;

N-{4-chloro-6-[N-(allyl)-N-(cyclopentyl)amino]-1,3,5-triazin-2-yl}-L-4-(N,N-dimethylcarbamyloxy)phenylalanine;

N-{4-chloro-6-[N-(ethyl)-N-(2-(4-methoxyphenyl)-1-methylethyl)-amino]-1,3,5-triazin-2-yl}-L-4-(N,N-dimethylcarbamyloxy)-phenylalanine;

N-{4-chloro-6-[N-(n-propyl)-N-(4-nitrobenzyl)amino]-1,3,5-triazin-2-yl}-L-4-(N,N-dimethylcarbamyloxy)-phenylalanine;

N-{4-chloro-6-[N-(methyl)-N-(2-pyridin-2-ylethyl)amino]-1,3,5-triazin-2-yl}-L-4-(N,N-dimethylcarbamyloxy)phenylalanine;

N-{4-chloro-6-[N,N-bis-(benzyl)amino]-1,3,5-triazin-2-yl}-L-4-(N,N-dimethylcarbamyloxy)phenylalanine;

N-{4-chloro-6-[N-(2-cyanoethyl)-N-(benzyl)amino]-1,3,5-triazin-2-yl}-L-4-(N,N-dimethylcarbamyloxy)phenylalanine;

N-{4-chloro-6-[N-(benzyl)-N-(2-dimethylaminoethyl)amino]-1,3,5-triazin-2-yl}-L-4-(N,N-dimethylcarbamyloxy)phenylalanine;

N-{6-[N-(ethyl)-N-(3,4-dichlorobenzyl)amino]-4-(2-methylpropylamino)-1,3,5-triazin-2-yl}-L-4-(N,N-dimethylcarbamyloxy)-phenylalanine;

N-{4-(benzylamino)-6-[N-(ethyl)-N-(pyridin-4-ylmethyl)amino]-1,3,5-triazin-2-yl}-L-4-(N,N-dimethylcarbamyloxy)phenylalanine;

N-{4-(benzylamino)-6-[N-(methyl)-N-(pyridin-3-ylmethyl)amino]-1,3,5-triazin-2-yl}-L-4-(N,N-dimethylcarbamyloxy)phenylalanine;

N-{4-(2-methoxyethylamino)-6-[N-(methyl)-N-(pyridin-2-ylmethyl)-amino]-1,3,5-triazin-2-yl}-L-4-(N,N-dimethylcarbamyloxy)-phenylalanine;

N-{4-(2-methoxyethylamino)-6-[N,N-bis-(pyridin-3-ylmethyl)-amino]-1,3,5-triazin-2-yl}-L-4-(N,N-dimethylcarbamyloxy)-phenylalanine;

N-{4-(2-methoxyethylamino)-6-[N,N-bis-(benzyl)amino]-1,3,5-triazin-2-yl}-L-4-(N,N-dimethylcarbamyloxy)phenylalanine;

N-{4-(cyclohexylamino)-6-[N-(phenyl)-N-(pyridin-2-yl) amino]-1,3,5-triazin-2-yl}-L-4-(N,N-dimethylcarbamyloxy)phenylalanine;

N-{6-[N,N-bis-(2-methoxyethyl)amino]-4-[N-(methyl)-N-(4-methylphenylsulfonyl)amino]-1,3,5-triazin-2-yl}-L-4-(N,N-dimethylcarbamyloxy)phenylalanine;

N-{4-[N-(benzyl)-N-(2-propyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N-(methyl)-N-(2-phenylethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N-(methyl)-N-(2-(3,4-dimethoxyphenyl)ethyl) amino]-6-[N-(methyl)-N-(4-methylphenylsulfonyl) amino]-1,3,5-triazin-2-yl}-L-4-(N,N-dimethylcarbamyloxy)phenylalanine;

N-{4-[N-(ethyl)-N-(pyridin-4-ylmethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N-(methyl)-N-(pyridin-3-ylmethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N-(ethyl)-N-(2-(4-methoxyphenyl)-1-methylethyl) amino]-6-[N-(methyl)-N-(4-methylphenylsulfonyl) amino]-1,3,5-triazin-2-yl}-L-4-(N,N-dimethylcarbamyloxy)phenylalanine;

N-{4-(4-aminosulfonylbenzylamino)-6-[N-(methyl)-N-(4-methylphenylsulfonyl)amino]-1,3,5-triazin-2-yl}-L-4-(N,N-dimethylcarbamyloxy)phenylalanine;

N-{4-[N-(methyl)-N-(3-dimethylaminopropyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N,N-bis-(benzyl)amino]-6-[N-(methyl)-N-(4-methylphenylsulfonyl)amino]-1,3,5-triazin-2-yl}-L-4-(N,N-dimethylcarbamyloxy)-phenylalanine;

N-{4-[N-(methyl)-N-(2-pyridin-2-ylethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N-(methyl)-N-(benzyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-(2-methylpropylamino]-6-[N-(methyl)-N-(4-methylphenylsulfonyl)amino]-1,3,5-triazin-2-yl}-L-4-(N,N-dimethylcarbamyloxy)-phenylalanine;

N-{4-(benzylamino)-6-[N-(methyl)-N-(4-methylphenylsulfonyl)-amino]-1,3,5-triazin-2-yl}-L-4-(N,N-dimethylcarbamyloxy)-phenylalanine;

N-{4-[2-(1-methylpyrrolidin-1yl)ethylamino]-6-[N-(methyl)-N-(4-methylphenylsulfonyl)amino]-1,3,5-triazin-2-yl}-L-4-(N,N-dimethylcarbamyloxy)phenylalanine;

N-{4-(furan-2-ylmethylamino)-6-[N-(methyl)-N-(4-methylphenylsulfonyl)amino]-1,3,5-triazin-2-yl}-L-4-(N,N-dimethylcarbamyloxy)-phenylalanine;

N-{4-[N,N-bis-(n-propyl)amino]-6-[N-(methyl)-N-(4-methylphenylsulfonyl)amino]-1,3,5-triazin-2-yl}-L-4-(N,N-dimethylcarbamyloxy)-phenylalanine;

N-{4-[N-(methyl)-N-(2-pyridin-2-ylethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-[N-(benzyl)-N-(2-dimethylaminoethyl)amino]-6-[N-(methyl)-N-(4-methylphenylsulfonyl)amino]-1,3,5-triazin-2-yl}-L-4-(N,N-dimethylcarbamyloxy)phenylalanine;

N-{4-(5-methylisoxazol-3-ylamino)-6-[N-(ethyl)-N-(2-(4-methoxyphenyl)-1-methylethyl)amino]-1,3,5-triazin-2-yl}-L-4-(N,N-dimethylcarbamyloxy)phenylalanine;

N-{4-chloro-6-[N-(methyl)-N-(pyridin-3-ylmethyl)amino]-1,3,5-triazin-2-yl}-L-4-(N,N-dimethylcarbamyloxy)phenylalanine;

N-{4-chloro-6[N,N-bis-cyclohexylamino]-1,3,5-triazin-2-yl}-L-4-(N,N-dimethylcarbamyloxy)phenylalanine;

N-{4-chloro-6-[N-(methyl)-N-(4-methylphenylsulfonyl) amino]-1,3,5-triazin-2-yl}-L-4-(N,N-dimethylcarbamyloxy)phenylalanine;

N-{4-[N-(2-methylpropyl)-N-(4-methylphenylsulfonyl) amino]-1,3,5-triazin-2-yl}-L-4-(N,N-dimethylcarbamyloxy)phenylalanine;

N-{4-[N-(methyl)-N-(4-methylphenylsulfonyl)amino]-1,3,5-triazin-2-yl}-L-4-(N,N-dimethylcarbamyloxy)phenylalanine;

N-{4-[N-(2-phenyl-1-carboxamidoethyl)amino]-1,3,5-triazin-2-yl}1-L-4-(N,N-dimethylcarbamyloxy)phenylalanine;

N-{4-(N-[2-phenyl-1,1-dimethylethyl)amino]-1,3,5-triazin-2-yl}-L-4-(N,N-dimethylcarbamyloxy)phenylalanine;

N-{4-[N-(2-phenylethyl)amino]-1,3,5-triazin-2-yl}-L-4-(N,N-dimethylcarbamyloxy)phenylalanine;

N-{4-[[N-(2-(2-methoxyphenyl)ethyl)amino]-1,3,5-triazin-2-yl}-L-4-(N,N-dimethylcarbamyloxy)phenylalanine;

N-{4-[N-(2-(3,4-dimethoxyphenyl)ethyl)amino]-1,3,5-triazin-2-yl}-L-4-(N,N-dimethylcarbamyloxy)phenylalanine;

N-{4-[N-(2-(4-fluorophenyl)-1,1-dimethylethyl)amino]-1,3,5-triazin-2-yl}-L-4-(N,N-dimethylcarbamyloxy)phenylalanine;

N-{4-[N-(1-phenyl-2-(4-methylphenyl)ethyl)amino]-1,3,5-triazin-2-yl}-L-4-(N,N-dimethylcarbamyloxy)phenylalanine;

N-{4-[N-(methyl)-N-(2-(3,4-dimethoxyphenyl)ethyl) amino]-1,3,5-triazin-2-yl}-L-4-(N,N-dimethylcarbamyloxy)phenylalanine;

N-{4-[N-(methyl)-N-(2-phenylethyl)amino]-1,3,5-triazin-2-yl}-L-4-(N,N-dimethylcarbamyloxy)phenylalanine;

N-{4-[N-(ethyl)-N-(2-(4-methoxyphenyl)-1-methylethyl) amino]-1,3,5-triazin-2-yl}-L-4-(N,N-dimethylcarbamyloxy)phenylalanine;

N-{4-chloro-6-[N-(benzyl)-N-(1-phenylethyl)amino]-1,3,5-triazin-2-yl}-L-4-(N,N-dimethylcarbamyloxy)phenylalanine;

N-{4-[N-(benzyl)-N-(1-phenylethyl)amino]-1,3,5-triazin-2-yl}-L-4-(N,N-dimethylcarbamyloxy)phenylalanine;

N-{4-chloro-6-(N-pyridin-4-ylmethylamino]-1,3,5-triazin-2-yl}-L-4-(N,N-dimethylcarbamyloxy)phenylalanine;

N-{4-chloro-6-(N-pyridin-3-ylmethylamino]-1,3,5-triazin-2-yl}-L-4-(N,N-dimethylcarbamyloxy)phenylalanine;

N-{4-chloro-6-[N-2-(pyridin-2-yl)ethylamino]-1,3,5-triazin-2-yl}-L-4-(N,N-dimethylcarbamyloxy)phenylalanine;

N-{4-chloro-6-[N-(2-ethylhexyl)-N-(pyridin-2-ylmethyl) amino]-1,3,5-triazin-2-yl}-L-4-(N,N-dimethylcarbamyloxy)phenylalanine;

N-{4-chloro-6-(N-pyridin-2-ylmethylamino)-1,3,5-triazin-2-yl}-L-4-(N,N-dimethylcarbamyloxy)phenylalanine;

N-{4-[N-(3,3-diphenylpropyl)amino]-1,3,5-triazin-2-yl}-L-4-(N,N-dimethylcarbamyloxy)phenylalanine;

N-{4-(N-pyridin-2-ylmethylamino)-1,3,5-triazin-2-yl}-L-4-(N,N-dimethylcarbamyloxy)phenylalanine;

N-{4-(N-pyridin-3-ylmethylamino)-1,3,5-triazin-2-yl}-L-4-(N,N-dimethylcarbamyloxy)phenylalanine;

N-{4-[N-2-(pyridin-2-yl)ethylamino]-1,3,5-triazin-2-yl}-L-4-(N,N-dimethylcarbamyloxy)phenylalanine;

N-{4-[N-2-(4-ethoxy-3-methoxyphenyl)ethylamino]-1,3,5-triazin-2-yl}-L-4-(N,N-dimethylcarbamyloxy)phenylalanine;

N-{4-[N-2-phenylpropylamino]-1,3,5-triazin-2-yl}-L-4-(N,N-dimethylcarbamyloxy)phenylalanine;

N-{4-[N-1 (S)-phenylethylamino]-1,3,5-triazin-2-yl}-L-4-(N,N-dimethylcarbamyloxy)phenylalanine;

N-{4-[N-(2-ethylhexyl)-N-(pyridin-2-ylmethyl)amino]-1,3,5-triazin-2-yl}-L-4-(N,N-dimethylcarbamyloxy)phenylalanine;

N-{4-chloro-6-[N-(4-(3,5-dioxopiperazin-1-ylsulfonyl)phenyl)amino]-1,3,5-triazin-2-yl}-L-4-(N,N-dimethylcarbamyloxy)phenylalanine;

N-{4-chloro-6-[N,N-dimethylamino]-1,3,5-triazin-2-yl}-L-4-(N,N-dimethylcarbamyloxy)phenylalanine;

N-{4-chloro-6-[N-(2-pyrrolidin-1-ylethyl)amino]-1,3,5-triazin-2-yl}-L-4-(N,N-dimethylcarbamyloxy)phenylalanine;

N-{4-hydroxy-6-[N-(2-phenylpropyl)amino]-1,3,5-triazin-2-yl}-L-4-(N,N-dimethylcarbamyloxy)phenylalanine;

N-{4-hydroxy-6-[N-(2-phenyl-1-carboxamidoethyl)amino]-1,3,5-triazin-2-yl}-L-4-(N,N-dimethylcarbamyloxy)phenylalanine;

N-{4-hydroxy-6-[N-(2-phenyl-1,1-dimethylethyl)amino]-1,3,5-triazin-2-yl}-L-4-(N,N-dimethylcarbamyloxy)phenylalanine;

N-{4-hydroxy-6-[N-(2-phenylethyl)amino]-1,3,5-triazin-2-yl}-L-4-(N,N-dimethylcarbamyloxy)phenylalanine;

N-{4-hydroxy-6-[N-(2-(2-methoxyphenyl)ethyl)amino]-1,3,5-triazin-2-yl}-L-4-(N,N-dimethylcarbamyloxy)phenylalanine;

N-{4-hydroxy-6-[N-(2-(3,4-dimethoxyphenyl)ethyl)amino]-1,3,5-triazin-2-yl}-L-4-(N,N-dimethylcarbamyloxy)phenylalanine;

N-{4-hydroxy-6-[N-(2-(4-fluorophenyl)-1,1-dimethylethyl)amino]-1,3,5-triazin-2-yl}-L-4-(N,N-dimethylcarbamyloxy)phenylalanine;

N-{4-hydroxy-6-[N-(1-phenyl-2-(4-methylphenyl)ethyl)amino]-1,3,5-triazin-2-yl}-L-4-(N,N-dimethylcarbamyloxy)phenylalanine;

N-{4-hydroxy-6-[N-(4-(3,5-dioxopiperazin-1-ylsulfonyl)phenyl)-amino]-1,3,5-triazin-2-yl}-L-4-(N,N-dimethylcarbamyloxy)-phenylalanine;

N-{4-hydroxy-6-(N,N-dimethylamino)-1,3,5-triazin-2-yl}-L-4-(N,N-dimethylcarbamyloxy)phenylalanine;

N-{4-hydroxy-6-[N-3-(imidazol-2-yl)propylamino]-1,3,5-triazin-2-yl}-L-4-(N,N-dimethylcarbamyloxy)phenylalanine;

N-{4-hydroxy-6-[N-2-(morpholin-4-yl)ethylamino]-1,3,5-triazin-2-yl}-L-4-(N,N-dimethylcarbamyloxy)phenylalanine;

N-{4-hydroxy-6-[N-2-(piperidin-1-yl)ethylamino]-1,3,5-triazin-2-yl}-L-4-(N,N-dimethylcarbamyloxy)phenylalanine;

N-{4-hydroxy-6-[N-2-(pyrrolidin-1-yl)ethylamino]-1,3,5-triazin-2-yl}-L-4-(N,N-dimethylcarbamyloxy)phenylalanine;

N-{4-hydroxy-6-[N-(1-ethoxycarbonylpiperidin-4-yl)amino]-1,3,5-triazin-2-yl}-L-4-(N,N-dimethylcarbamyloxy)phenylalanine;

N-{4-hydroxy-6-[N-2-(phenoxy)ethylamino]-1,3,5-triazin-2-yl}-L-4-(N,N-dimethylcarbamyloxy)phenylalanine;

N-{4-hydroxy-6-[N-3-(pyrrolidin-1-yl)propylamino]-1,3,5-triazin-2-yl}-L-4-(N,N-dimethylcarbamyloxy)phenylalanine;

N-{4-chloro-6-[N-3-(pyrrolidin-1-yl)propylamino]-1,3,5-triazin-2-yl}-L-4-(N,N-dimethylcarbamyloxy)phenylalanine;

N-{4-hydroxy-6-[N-(benzyl)-N-(1-(S)-phenylethyl)amino]-1,3,5-triazin-2-yl}-L-4-(N,N-dimethylcarbamyloxy)phenylalanine;

N-{4-hydroxy-6-[N-(5-chloro-1,3-dimethylpyrazol-4-yl)amino]-1,3,5-triazin-2-yl}-L-4-(N,N-dimethylcarbamyloxy)phenylalanine;

N-{4-hydroxy-6-[N-(benzylsulfonyl)amino]-1,3,5-triazin-2-yl}-L-4-(N,N-dimethylcarbamyloxy)phenylalanine;

N-{4-hydroxy-6-[N-(1-(R)-phenyl-2-carboxyethyl)amino]-1,3,5-triazin-2-yl}-L-4-(N,N-dimethylcarbamyloxy)phenylalanine;

N-{4-hydroxy-6-[N-(1-phenylethyl)amino]-1,3,5-triazin-2-yl}-L-4-(N,N-dimethylcarbamyloxy)phenylalanine;

N-{4-hydroxy-6-[N-(1-phenyl-1-ethoxycarbonylmethyl)amino]-1,3,5-triazin-2-yl}-L-4-(N,N-dimethylcarbamyloxy)phenylalanine;

N-{4-chloro-6-[N-(benzyl)-N-(1-carboxy-2-phenylethyl)amino]-1,3,5-triazin-2-yl}-L-4-(N,N-dimethylcarbamyloxy)phenylalanine;

N-{4-[N-(4-(3,5-dioxopiperazin-1-ylsulfonyl)phenyl)amino]-1,3,5-triazin-2-yl}-L-4-(N,N-dimethylcarbamyloxy)phenylalanine;

N-{4-[N-(pyridin-4-ylmethyl)amino]-1,3,5-triazin-2-yl}-L-4-(N,N-dimethylcarbamyloxy)phenylalanine;

N-{4-[N-(2-(4-benzylpiperazin-1yl)ethyl)amino]-1,3,5-triazin-2-yl}-L-4-(N,N-dimethylcarbamyloxy)phenylalanine;

N-{4-(N,N-dimethylamino)-1,3,5-triazin-2-yl}-L-4-(N,N-dimethylcarbamyloxy)phenylalanine;

N-{4-(N-(2-morpholin-4-ylethyl)amino)-1,3,5-triazin-2-yl}-L-4-(N,N-dimethylcarbamyloxy)phenylalanine;

N-{4-(N-(2-phenoxyethyl)amino)-1,3,5-triazin-2-yl}-L-4-(N,N-dimethylcarbamyloxy)phenylalanine;

N-{4-[N-(2-carboxy-1-(R)-phenylethyl)amino]-1,3,5-triazin-2-yl}-L-4-(N,N-dimethylcarbamyloxy)phenylalanine;

N-{4-[N-(1-ethoxycarbonyl-1-phenylmethyl)amino]-1,3,5-triazin-2-yl}-L-4-(N,N-dimethylcarbamyloxy)phenylalanine;

N-{4-[N-(1-carboxy-3-phenylpropyl)amino]-1,3,5-triazin-2-yl}-L-4-(N,N-dimethylcarbamyloxy)phenylalanine;

N-{4-[N-(1-phenylethyl)amino]-1,3,5-triazin-2-yl}-L-4-(N,N-dimethylcarbamyloxy)phenylalanine;

N-{4-[N-(2-carboxy-1-phenylethyl)amino]-1,3,5-triazin-2-yl}-L-4-(N,N-dimethylcarbamyloxy)phenylalanine;

N-{4-(N-2-methylpropylamino)-6-(4-phenylpiperazin-1-yl)-1,3,5-triazin-2-yl}-L-4-(N,N-dimethylcarbamyloxy)phenylalanine;

N-{4-(N-2-methylpropylamino)-6-(4-acetylpiperazin-1-yl)-1,3,5-triazin-2-yl}-L-4-(N,N-dimethylcarbamyloxy)phenylalanine;

N-{4-(N-6-nitrobenzthiazol-2-ylamino)-6-(piperidin-1-yl)-1,3,5-triazin-2-yl}-L-4-(N,N-dimethylcarbamyloxy)phenylalanine;

N-{4-(N-furan-2-ylmethylamino)-6-(piperidin-1-yl)-1,3,5-triazin-2-yl}-L-4-(N,N-dimethylcarbamyloxy)phenylalanine;

N-{4-(N-1-phenylethylamino)-6-(piperidin-1-yl)-1,3,5-triazin-2-yl}-L-4-(N,N-dimethylcarbamyloxy)phenylalanine;

N-{4-(N-4-chlorobenzylamino)-6-(piperidin-1-yl)-1,3,5-triazin-2-yl}-L-4-(N,N-dimethylcarbamyloxy)phenylalanine;

N-{4-(piperidin-1-yl)-6-(4-acetylpiperazin-1-yl)-1,3,5-triazin-2-yl}-L-4-(N,N-dimethylcarbamyloxy)phenylalanine;

N-{4-(N-4-aminosulfonylbenzylamino)-6-(piperidin-1-yl)-1,3,5-triazin-2-yl}-L-4-(N,N-dimethylcarbamyloxy)phenylalanine;

N-{4-(N-benzylamino)-6-(4-acetylpiperazin-1-yl)-1,3,5-triazin-2-yl}-L-4-(N,N-dimethylcarbamyloxy)phenylalanine;

N-{4-(N-cyclopentylamino)-6-(4-acetylpiperazin-1-yl)-1,3,5-triazin-2-yl}-L-4-(N,N-dimethylcarbamyloxy)phenylalanine;

N-{4-chloro-6-(4-benzylpiperidin-1-yl)-1,3,5-triazin-2-yl}-L-4-(N,N-dimethylcarbamyloxy)phenylalanine;

N-{4-chloro-6-(5-ethyl-2-methylpiperidin-1-yl)-1,3,5-triazin-2-yl}-L-4-(N,N-dimethylcarbamyloxy)phenylalanine;

N-{4-chloro-6-(4-phenylpiperazin-1-yl)-1,3,5-triazin-2-yl}-L-4-(N,N-dimethylcarbamyloxy)phenylalanine;

N-{4-chloro-6-[4-(3,4-methylenedioxybenzyl)piperazin-1-yl]-1,3,5-triazin-2-yl}-L-4-(N,N-dimethylcarbamyloxy) phenylalanine;

N-{4-chloro-6-(4-diphenylmethylpiperazin-1-yl)-1,3,5-triazin-2-yl}-L-4-(N,N-dimethylcarbamyloxy)phenylalanine;

N-{4-chloro-6-(4-acetylpiperazin-1-yl)-1,3,5-triazin-2-yl}-L-4-(N,N-dimethylcarbamyloxy)phenylalanine;

N-{4-chloro-6-(3-methylpiperidin-1-yl)-1,3,5-triazin-2-yl}-L-4-(N,N-dimethylcarbamyloxy)phenylalanine;

N-{4-chloro-6-(3,5-dimethylmorpholin-4-yl)-1,3,5-triazin-2-yl}-L-4-(N,N-dimethylcarbamyloxy)phenylalanine;

N-{4-(N-cyclohexylamino-6-(3,5-dimethylmorpholin-4-yl)-1,3,5-triazin-2-yl}-L-4-(N,N-dimethylcarbamyloxy) phenylalanine;

N-{4-[N-methyl-N-(4-methylphenylsulfonyl)amino]-6-(4-cyclohexyl-piperazin-1-yl)-1,3,5-triazin-2-yl}-L-4-(N,N-dimethylcarbamyloxy)-phenylalanine;

N-{4-[N-methyl-N-(4-methylphenylsulfonyl)amino]-6-(3-methyl piperidin-1-yl)-1,3,5-triazin-2-yl}-L-4-(N,N-dimethylcarbamyloxy)-phenylalanine;

N-{4-[N-(2-(4-aminosulfonylphenyl)ethyl)amino]-6-(piperidin-1-yl)-1,3,5-triazin-2-yl}-L-4-(N,N-dimethylcarbamyloxy)phenylalanine;

N-{4-chloro-6-[2-(4-benzylpiperazin-1-yl)ethyl)amino]-1,3,5-triazin-2-yl}-L-4-(N,N-dimethylcarbamyloxy)phenylalanine;

N-{4-chloro-6-[4-(isopropylaminocarbonylmethyl)piperazin-1-yl]-1,3,5-triazin-2-yl}-L-4-(N,N-dimethylcarbamyloxy)phenylalanine;

N-{4-chloro-6-[4-(1-phenylethyl)piperazin-1-yl]-1,3,5-triazin-2-yl}-L-4-(N,N-dimethylcarbamyloxy)phenylalanine;

N-{4-chloro-6-[4-(2-phenylethyl)piperazin-1-yl]-1,3,5-triazin-2-yl}-L-4-(N,N-dimethylcarbamyloxy)phenylalanine;

N-{4-chloro-6-[4-(furan-2-ylcarbonyl)piperazin-1-yl]-1,3,5-triazin-2-yl}-L-4-(N,N-dimethylcarbamyloxy)phenylalanine;

N-{4-chloro-6-[4-(1-phenylpropen-1-yl)piperazin-1-yl]-1,3,5-triazin-2-yl}-L-4-(N,N-dimethylcarbamyloxy)phenylalanine;

N-{4-[4-(isopropylaminocarbonylmethyl)piperazin-1-yl]-1,3,5-triazin-2-yl}-L-4-(N,N-dimethylcarbamyloxy)phenylalanine;

N-{4-[4-(2-phenylethyl)piperazin-1-yl]-1,3,5-triazin-2-yl}-L-4-(N,N-dimethylcarbamyloxy)phenylalanine;

N-{4-[4-(furan-2-ylcarbonyl)piperazin-1-yl]-1,3,5-triazin-2-yl}-L-4-(N,N-dimethylcarbamyloxy)phenylalanine;

N-{4-[4-(2-morpholin-4-ylethyl)piperazin-1-yl]-1,3,5-triazin-2-yl}-L-4-(N,N-dimethylcarbamyloxy)phenylalanine;

N-{4-chloro-6-(1,2,3,4-tetrahydroisoquinolin-2-yl)-1,3,5-triazin-2-yl}-L-4-(N,N-dimethylcarbamyloxy)phenylalanine;

N-{4-hydroxy-6-(1,2,3,4-tetrahydroisoquinolin-2-yl)-1,3,5-triazin-2-yl}-L-4-(N,N-dimethylcarbamyloxy)phenylalanine;

N-{4-chloro-6-[4-(ethoxycarbonylmethyl)piperazin-1-yl]-1,3,5-triazin-2-yl}-L-4-(N,N-dimethylcarbamyloxy)phenylalanine;

N-{4-hydroxy-6-[4-(ethoxycarbonylmethyl)piperazin-1-yl]-1,3,5-triazin-2-yl}-L-4-(N,N-dimethylcarbamyloxy)phenylalanine;

N-{4-chloro-6-(piperazin-1-yl)-1,3,5-triazin-2-yl}-L-4-(N,N-dimethylcarbamyloxy)phenylalanine;

N-{4-chloro-6-[4-(2-methoxyethyl)piperazin-1-yl]-1,3,5-triazin-2-yl}-L-4-(N,N-dimethylcarbamyloxy)phenylalanine;

N-{4-chloro-6-(2-ethoxycarbonylpiperidin-1-yl]-1,3,5-triazin-2-yl}-L-4-(N,N-dimethylcarbamyloxy)phenylalanine;

N-{4-chloro-6-[2-(ethoxycarbonylmethyl)-3-oxopiperazin-1-yl]-1,3,5-triazin-2-yl}-L-4-(N,N-dimethylcarbamyloxy)phenylalanine;

N-{4-hydroxy-6-[2-(ethoxycarbonylmethyl)-3-oxopiperazin-1-yl]-1,3,5-triazin-2-yl}-L-4-(N,N-dimethylcarbamyloxy)phenylalanine;

N-{4-chloro-6-(3-ethoxycarbonylpiperidin-1-yl]-1,3,5-triazin-2-yl}-L-4-(N,N-dimethylcarbamyloxy)phenylalanine;

N-{4-hydroxy-6-(3-(R)methoxycarbonyl-1,2,3,4-tetrahydroisoquinolin-1-yl)-1,3,5-triazin-2-yl}-L-4-(N,N-dimethylcarbamyloxy)-phenylalanine;

N-{4-chloro-6-(3-methoxycarbonyl-1,2,3,4-tetrahydroisoquinolin-1-yl)-1,3,5-triazin-2-yl}-L-4-(N,N-dimethylcarbamyloxy)-phenylalanine;

N-{4-hydroxy-6-(3-methoxycarbonyl-1,2,3,4-tetrahydroisoquinolin-1-yl)-1,3,5-triazin-2-yl}-L-4-(N,N-dimethylcarbamyloxy)-phenylalanine;

N-{4-(1,2,3,4-tetrahydroisoquinolin-2-yl)-1,3,5-triazin-2-yl}-L-4-(N,N-dimethylcarbamyloxy)phenylalanine;

N-{4-[4-(ethoxycarbonylmethyl)piperazin-1-yl]-1,3,5-triazin-2-yl}-L-4-(N,N-dimethylcarbamyloxy)phenylalanine;

N-{4-(piperazin-1-yl]-1,3,5-triazin-2-yl}-L-4-(N,N-dimethylcarbamyloxy)phenylalanine;

N-{4-(2-ethoxycarbonylpiperidin-1-yl]-1,3,5-triazin-2-yl}-L-4-(N,N-dimethylcarbamyloxy)phenylalanine;

N-{4-[2-(ethoxycarbonylmethyl)-3-oxopiperazin-1-yl]1,3,5-triazin-2-yl}-L-4-(N,N-dimethylcarbamyloxy)phenylalanine;

N-{4-(3-carboxy-1,2,3,4-tetrahydroisoquinolin-2-yl)-1,3,5-triazin-2-yl}-L-4-(N,N-dimethylcarbamyloxy)phenylalanine;

N-{6-[N-(2-methylpropyl)-N-(4-methylphenylsulfonyl) amino]-pyrimidin-4-yl)}-L-4-(N,N-dimethylcarbamyloxy)phenylalanine;

N-{6-[N-(methyl)-N-(4-methylphenylsulfonyl)amino]-pyrimidin-4-yl}-L-4-(N,N-dimethylcarbamyloxy)phenylalanine;

N-{6-[N-(2-phenylethyl)amino]pyrimidin-4-yl}-L-4-(N,N-dimethylcarbamyloxy)phenylalanine;

N-{6-[N-(methyl)-N-(2-pyridin-2-ylethyl)amino]pyrimidin-4-yl}-L-4-(N,N-dimethylcarbamyloxy)phenylalanine;
N-{6-[N-(methyl)-N-(benzyl)amino]pyrimidin-4-yl}-L-4-(N,N-dimethylcarbamyloxy)phenylalanine;
N-{6-(4-acetylpiperazin-1-yl)pyrimidin-4-yl}-L-4-(N,N-dimethylcarbamyloxy)phenylalanine;
N-{6-[N-(methyl)-N-(pyridin-3-ylmethyl)amino]pyrimidin-4-yl}-L-4-(N,N-dimethylcarbamyloxy)phenylalanine;
N-{6-[N-(methyl)-N-(2-(3,4-dimethoxyphenyl)ethyl)amino]pyrimidin-4-yl}-L-4-(N,N-dimethylcarbamyloxy)phenylalanine;
N-{6-[N-(methyl)-N-(2-phenylethyl)amino]pyrimidin-4-yl}-L-4-(N,N-dimethylcarbamyloxy)phenylalanine;
N-{6-[N-(2-methyl-2-phenylethyl)amino]pyrimidin-4-yl}-L-4-(N,N-dimethylcarbamyloxy)phenylalanine;
N-{6-[4-(2-propylaminocarbonylmethyl)piperazin-1-yl]pyrimidin-4-yl}-L-4-(N,N-dimethylcarbamyloxy)phenylalanine;
N-{6-[4-(2-morpholin-4-ylethyl)piperazin-1-yl]pyrimidin-4-yl}-L-4-(N,N-dimethylcarbamyloxy)phenylalanine;
N-{6-[N-(2-phenylethyl)amino]pyrimidin-4-yl}-L-4-(N,N-dimethylcarbamyloxy)phenylalanine.

Example A

In vitro Assay For Determining Binding of Candidate Compounds to VLA-4

An in vitro assay was used to assess binding of candidate compounds to $\alpha_4\beta_1$ integrin. Compounds which bind in this assay can be used to assess VCAM-1 levels in biological samples by conventional assays (e.g., competitive assays). This assay is sensitive to $IC_{50}$ values as low as about 1 nM.

The activity of $\alpha_4\beta_1$ integrin was measured by the interaction of soluble VCAM-1 with Jurkat cells (e.g., American Type Culture Collection Nos. TIB 152, TIB 153, and CRL 8163), a human T-cell line which expresses high levels of $\alpha_4\beta_1$ integrin. VCAM-1 interacts with the cell surface in an $\alpha_4\beta_1$ integrin-dependent fashion (Yednock, et al. J. Biol. Chem., 1995, 270:28740).

Recombinant soluble VCAM-1 was expressed as a chimeric fusion protein containing the seven extracellular domains of VCAM-1 on the N-terminus and the human $IgG_1$ heavy chain constant region on the C-terminus. The VCAM-1 fusion protein was made and purified by the manner described by Yednock, supra.

Jurkat cells were grown in RPMI 1640 supplemented with 10% fetal bovine serum, penicillin, streptomycin and glutamine as described by Yednock, supra.

Jurkat cells were incubated with 1.5 mM MnCl and 5 μg/mL 15/7 antibody for 30 minutes on ice. $Mn^{+2}$ activates the receptor to enhance ligand binding, and 15/7 is a monoclonal antibody that recognizes an activated/ligand occupied conformation of $\alpha_4\beta_1$ integrin and locks the molecule into this conformation thereby stabilizing the VCAM-1/$\alpha_4\beta_1$ integrin interaction. Yednock, et al., supra. Antibodies similar to the 15/7 antibody have been prepared by other investigators (Luque, et al, 1996, J. Biol. Chem. 271:11067) and may be used in this assay.

Cells were then incubated for 30 minutes at room temperature with candidate compounds, in various concentrations ranging from 66 μM to 0.01 μM using a standard 5-point serial dilution. 15 μL soluble recombinant VCAM-1 fusion protein was then added to Jurkat cells and incubated for 30 minutes on ice. (Yednock et al., supra.).

Cells were then washed two times and resuspended in PE-conjugated goat $F(ab')_2$ anti-mouse IgG Fc (Immunotech, Westbrook, Me.) at 1:200 and incubated on ice, in the dark, for 30 minutes. Cells were washed twice and analyzed with a standard fluorescence activated cell sorter ("FACS") analysis as described in Yednock, et al., supra.

Compounds having an $IC_{50}$ of less than about 15 μM possess binding affinity to $\alpha_4\beta_1$.

When tested in this assay, each of the compound prepared in the above examples has or is expected to have an $IC_{50}$ of 15 μM or less (or is expected to be active in vivo).

Example B

In Vitro Saturation Assay for Determining Binding of Candidate Compounds to $\alpha_4\beta_1$ The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 μg/ml of the 15/7 antibody (described in the above example).

The Jurkat cells are diluted two-fold into either normal plasma samples containing known candidate compound amounts in various concentrations ranging from 66 μM to 0.01 μM, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat $F(ab')_2$ anti-mouse IgG Fc (Immunotech, Westbrook, Me.), which has been adsorbed for any non-specific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter ("FACS") analysis as described in Yednock et al. J. Biol. Chem., 1995, 270:28740.

The data is then graphed as fluorescence versus dose, e.g., in a normal dose-response fashion. The dose levels that result in the upper plateau of the curve represent the levels needed to obtain efficacy in an in vivo model.

This assay may also be used to determine the plasma levels needed to saturate the binding sites of other integrins, such as the $\alpha_9\beta_1$ integrin, which is the integrin most closely related $\alpha_4\beta_1$ (Palmer et al, 1993, J. Cell Bio., 123:1289). Such binding is predictive of in vivo utility for inflammatory conditions mediated by $\alpha_9\beta_1$ integrin, including by way of example, airway hyper-responsiveness and occlusion that occurs with chronic asthma, smooth muscle cell proliferation in atherosclerosis, vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis and Crohn's disease.

Accordingly, the above-described assay may be performed with a human colon carcinoma cell line, SW 480 (ATTC #CCL228) transfected with cDNA encoding $\alpha_9$ integrin (Yokosaki et al., 1994, J. Biol. Chem., 269:26691), in place of the Jurkat cells, to measure the binding of the $\alpha_9\beta_1$ integrin. As a control, SW 480 cells which express other α and $\beta_1$ subunits may be used.

Accordingly, another aspect of this invention is directed to a method for treating a disease in a mammalian patient, which disease is mediated by $\alpha_{9\beta1}$, and which method comprises administering to said patient a therapeutically effective amount of a compound of this invention. Such compounds are preferably administered in a pharmaceutical composition described herein above. Effective daily dosing will depend upon the age, weight, condition of the patient which factors can be readily ascertained by the attending clinician. However, in a preferred embodiment, the compounds are administered from about 20 to 500 μg/kg per day.

Example C

In Vivo Evaluation

The standard multiple sclerosis model, Experimental Autoimmune (or Allergic) Encephalomyelitis ("EAE"), was used to determine the effect of candidate compounds to reduce motor impairment in rats or guinea pigs. Reduction in motor impairment is based on blocking adhesion between leukocytes and the endothelium and correlates with anti-inflammatory activity in the candidate compound. This model has been previously described by Keszthelyi et al., Neurology, 1996, 47:1053-1059, and measures the delay of onset of disease.

Brains and spinal cords of adult Hartley guinea pigs were homogenized in an equal volume of phosphate-buffered saline. An equal volume of Freund's complete adjuvant (100 mg *mycobacterium tuberculosis* plus 10 ml Freund's incomplete adjuvant) was added to the homogenate; The mixture was emulsified by circulating it repeatedly through a 20 ml syringe with a peristaltic pump for about 20 minutes.

Female Lewis rats (2-3 months old, 170-220 g) or Hartley guinea pigs (20 day old, 180-200 g) were anesthetized with isoflurane and three injections of the emulsion, 0.1 ml each, were made in each flank. Motor impairment onset is seen in approximately 9 days.

Candidate compound treatment began on Day 8, just before onset of symptoms. Compounds were administered subcutaneously ("SC"), orally ("PO") or intraperitoneally ("IP"). Doses were given in a range of 10 mg/kg to 200 mg/kg, bid, for five days, with typical dosing of 10 to 100 mg/kg SC, 10 to 50 mg/kg PO, and 10 to 100 mg/kg IP.

Antibody GG5/3 against $\alpha_4\beta_1$ integrin (Keszthelyi et al., Neurology, 1996, 47:1053-1059), which delays the onset of symptoms, was used as a positive control and was injected subcutaneously at 3 mg/kg on Day 8 and 11.

Body weight and motor impairment were measured daily. Motor impairment was rated with the following clinical score:

| | |
|---|---|
| 0 | no change |
| 1 | tail weakness or paralysis |
| 2 | hindlimb weakness |
| 3 | hindlimb paralysis |
| 4 | moribund or dead |

A candidate compound was considered active if it delayed the onset of symptoms, e.g., produced clinical scores no greater than 2 or slowed body weight loss as compared to the control.

Example D

Asthma Model

Inflammatory conditions mediated by $\alpha_4\beta_1$ integrin include, for example, airway hyper-responsiveness and occlusion that occurs with chronic asthma. The following describes an asthma model which can be used to study the in vivo effects of the compounds of this invention for use in treating asthma.

Following the procedures described by Abraham et al, J. Clin. Invest, 93:776-787 (1994) and Abraham et al, Am J. Respir Crit Care Med, 156:696-703 (1997), both of which are incorporated by reference in their entirety. Compounds of this invention are formulated into an aerosol and administered to sheep which are hypersensitive to *Ascaris suum* antigen. Compounds which decrease the early antigen-induced bronchial response and/or block the late-phase airway response, e.g., have a protective effect against antigen-induced late responses and airway hyper-responsiveness ("AHR"), are considered to be active in this model.

Allergic sheep which are shown to develop both early and late bronchial responses to inhaled *Ascaris suum* antigen are used to study the airway effects of the candidate compounds. Following topical anesthesia of the nasal passages with 2% lidocaine, a balloon catheter is advanced through one nostril into the lower esophagus. The animals are then intubated with a cuffed endotracheal tube through the other nostril with a flexible fiberoptic bronchoscope as a guide.

Pleural pressure is estimated according to Abraham (1994). Aerosols (see formulation below) are generated using a disposable medical nebulizer that provides an aerosol with a mass median aerodynamic diameter of 3.2 μm as determined with an Andersen cascade impactor. The nebulizer is connected to a dosimeter system consisting of a solenoid valve and a source of compressed air (20 psi). The output of the nebulizer is directed into a plastic T-piece, one end of which is connected to the inspiratory port of a piston respirator. The solenoid valve is activated for 1 second at the beginning of the inspiratory cycle of the respirator. Aerosols are delivered at VT of 500 ml and a rate of 20 breaths/minute. A 0.5% sodium bicarbonate solution only is used as a control.

To assess bronchial responsiveness, cumulative concentration-response curves to carbachol can be generated according to Abraham (1994). Bronchial biopsies can be taken prior to and following the initiation of treatment and 24 hours after antigen challenge. Bronchial biopsies can be preformed according to Abraham (1994).

An in vitro adhesion study of alveolar macrophages can also be performed according to Abraham (1994), and a percentage of adherent cells is calculated.

Aerosol Formulation

A solution of the candidate compound in 0.5% sodium bicarbonate/saline (w/v) at a concentration of 30.0 mg/mL is prepared using the following procedure:

A. Preparation of 0.5% Sodium Bicarbonate/Saline Stock Solution: 100.0 mL

| Ingredient | Gram/100.0 mL | Final Concentration |
|---|---|---|
| Sodium Bicarbonate | 0.5 g | 0.5% |
| Saline | q.s. ad 100.0 mL | q.s. ad 100% |

Procedure:

1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

B. Preparation of 30.0 mg/mL Candidate Compound: 10.0 mL

| Ingredient | Gram/10.0 mL | Final Concentration |
|---|---|---|
| Candidate Compound | 0.300 g | 30.0 mg/mL |
| 0.5% Sodium Bicarbonate/Saline Stock Solution | q.s. ad 10.0 mL | q.s ad 100% |

Procedure:

1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.
4. Q.S. to 10.0 mL with 0.5% sodium bicarbonate/saline stock solution and mix thoroughly.

Using a conventional oral formulation, compounds of this invention would be active in this model.

Example E

Allograft Model

Allograft rejection, associated with infiltration of inflammatory cells, is the leading obstacle to long-term allograft survival. Cell surface adhesion molecules facilitate alloantigen recognition in vitro and may be critical for lymphocyte traffic in vivo. The following describes a model which can be used to study the in vivo effects of the compounds of this invention in the control of allograft rejection.

The following procedures are described in Coito et al., *Transplantation* (1998) 65(6):699-706 and in Korom et al., *Transplantation* (1998) 65(6):854-859, both of which are incorporated by reference in their entirety.

Following the procedures described in Coito and Korom, male adult rats weighing approximately 200-250 g are used in this model. Lewis rats are used as the recipients of cardiac allografts from Lewis X Brown Norway rats. Hearts are transplanted into the abdominal great vessels using standard microvascular techniques.

A candidate compound is administered to the transplant recipient in a suitable pharmaceutical carrier for a 7-day course of treatment starting the day of the engraftment. Doses range from 0.3 to 30 mg/kg/day. Control recipients receive the pharmaceutical carrier only.

The rats are euthanized and their cardiac allografts are analyzed as described in Coito and Korom.

Using conventional formulations, compounds of this invention would be active in this model.

What is claimed is:

1. A compound of formula:

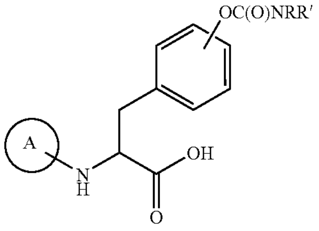

wherein:

ring A is selected from the group consisting of pyridyl, pyrrole, pyrazole, imidazole, 1,2,3-triazole, 1,2,4-triazole, tetrazole, and thiophene wherein said pyridyl is substituted with 1 to 4 substituents, each of said pyrrole, pyrazole, imidazole, and thiophene is substituted with 1 to 3 substituents, and each of said 1,2,3-triazole, 1,2,4-triazole, and tetrazole is substituted with 1 to 2 substituents independently selected from the group consisting of alkyl, alkoxy, halogen, amino, substituted amino, aryl, substituted aryl, heteroaryl, substituted heteroaryl, heterocycle, substituted heterocycle and $-SO_2R^a$ wherein $R^a$ is alkyl, aryl or substituted aryl; and R and R' are independently selected from the group consisting of hydrogen, alkyl, substituted alkyl, cycloalkyl, substituted cycloalkyl, cylcoalkenyl, substituted cycloatkenyl, heterocyclic, substituted heterocyclic and where R and R' are joined together with the nitrogen atom bound thereto to form a heterocycle or substituted heterocycle; or a pharmaceutically acceptable salt thereof.

2. A compound of formula:

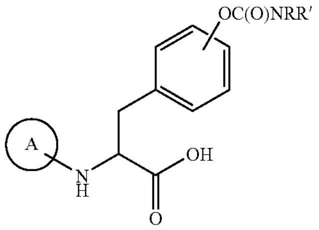

wherein:

ring A is selected from the group consisting of pyridyl, 3-nitrothienyl, 1-phenyltetrazol-5-yl, 1,5-dimethyl-4-nitropyrazol-3-yl, 1-ethylpyrazol-yl, 4-phenylsulfonylthien-3-yl, 1,4-diphenylpyrazol-5-yl, 1-phenylimidazol-2-yl, and 5-benzoylmethylsulfinyl-4-(3-trifluoromethylphenyl)-1,2,4-triazol-3-yl and R and R' are independently selected from the group consisting of hydrogen, alkyl, substituted alkyl, cycloalkyl, substituted cycloalkyl, cylcoalkenyl, substituted cycloalkenyl, heterocyclic, substituted heterocyclic and where R and R' are joined together with the nitrogen atom bound thereto to form a heterocycle or substituted heterocycle; or a pharmaceutically acceptable salt thereof.

3. A compound selected from the group consisting of:

N-(3-nitrothien-2-yl)-L-4-(N,N-dimethylcarbamyloxy)phenylalanine;

N-(1-phenyltetrazol-5-yl)-L-4-(N,N-dimethylcarbamyloxy)phenylalanine;

N-(1,3-dimethyl-4-nitropyrazol-5-yl)-L-4-(N,N-dimethylcarbamyloxy)phenylalanine;

N-(1-ethylpyrazol-5-yl)-L-4-(N,N-dimethylcarbamyloxy)phenylalanine;

N-(4-phenylsulfonylthien-3-yl)-L-4-{N,N-dimethylcarbamyloxy)phenylalanine;

N-(1,4-diphenyl-1,2-3-triazol-5-yl)-L-4-(N,N-dimethylcarbamyloxy)phenylalanine;

N-(1-phenylimidazol-2-yl)-L-4-(N,N-dimethylcarbamyloxy)phenylalanine; N-(6-bromopyridin-2-yl)-L-4-(N,N-dimethylcarbamyloxy)phenylalanine;

N-(6-naphth-1-ylpyridin-2-yl)-L-4-(N,N-dimethylcarbamyloxy)phenylalanine; N-(3 -[N-methyl-N-(4-methylphenylsulfonyl)amino]pyridin-2-yl)-L-4-(N,N-dimethylcarbamyloxy)phenylalanine;

N-(3-[N-methyl-N-(4-methylphenylsulfonyl)amino]pyridin-4-yl)-L-4-(N,N-dimethylcarbamyloxy)phenylalanine;

N-(5-trifluoromethylpyridin-2-yl)-L-4-(N,N-dimethylcarbamyloxy)phenylalanine;

N-(4-methyl-3-nitropyridin-2-yl)-L-4-(N,N-dimethylcarbamyloxy)phenylalanine;

N-(3,5-di-nitropyridin-2-yl)-L-4-(N,N-dimethylcarbamyloxy)phenylalanine; and

N-(3-[N-methyl-N-(4-methylphenylsulfonyl)amino]-4-methylpyridin-4-yl)-L-4-(N,N-dimethylcarbamyloxy) phenylalanine;

or a pharmaceutically acceptable salt thereof.

4. A pharmaceutical composition comprising a pharmaceutically acceptable excipient and a pharmaceutically effective amount of a compound according to any one of claims 1, 2 and 3.

* * * * *